(12) United States Patent
Masel et al.

(10) Patent No.: US 9,566,574 B2
(45) Date of Patent: Feb. 14, 2017

(54) CATALYST MIXTURES

(75) Inventors: Richard I. Masel, Champaign, IL (US); Brian A. Rosen, Wilmington, DE (US)

(73) Assignee: Dioxide Materials, Inc., Boca Raton, FL (US)

( * ) Notice: Subject to any disclaimer, the term of this patent is extended or adjusted under 35 U.S.C. 154(b) by 416 days.

(21) Appl. No.: 13/174,365

(22) Filed: Jun. 30, 2011

(65) Prior Publication Data

US 2012/0308903 A1   Dec. 6, 2012

Related U.S. Application Data

(60) Provisional application No. 61/484,072, filed on May 9, 2011.

(30) Foreign Application Priority Data

Mar. 25, 2011   (WO) ................ PCT/US2011/030098

(51) Int. Cl.
*H01M 4/92* (2006.01)
*H01M 4/90* (2006.01)
(Continued)

(52) U.S. Cl.
CPC ......... *B01J 31/0239* (2013.01); *B01J 31/0204* (2013.01); *B01J 31/0209* (2013.01);
(Continued)

(58) Field of Classification Search
None
See application file for complete search history.

(56) References Cited

U.S. PATENT DOCUMENTS

| | | |
|---|---|---|
| 1,919,850 A | 7/1933 | Luscher |
| 2,511,198 A | 6/1950 | Engel |

(Continued)

FOREIGN PATENT DOCUMENTS

| | | |
|---|---|---|
| CA | 1272180 A | 7/1990 |
| CA | 2821642 A1 | 6/2012 |

(Continued)

OTHER PUBLICATIONS

Magdesieva, T.V. et al., "Lutetium monophthalocyanine and diphthalocyanine complexes and lithium naphthalocyanine as catalysts for electrochemical CO2 reduction", Journal of the Electrochemical Society 150 (2003), pp. E608-E612.

(Continued)

*Primary Examiner* — Barbara Gilliam
*Assistant Examiner* — Angela Martin
(74) *Attorney, Agent, or Firm* — Corridor Law Group, P.C.

(57) ABSTRACT

Catalysts that include at least one catalytically active element and one helper catalyst can be used to increase the rate or lower the overpotential of chemical reactions. The helper catalyst can simultaneously act as a director molecule, suppressing undesired reactions and thus increasing selectivity toward the desired reaction. These catalysts can be useful for a variety of chemical reactions including, in particular, the electrochemical conversion of $CO_2$ or formic acid. The catalysts can also suppress $H_2$ evolution, permitting electrochemical cell operation at potentials below RHE. Chemical processes and devices using the catalysts are also disclosed, including processes to produce CO, $OH^-$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, or $(COO^-)_2$, and a specific device, namely, a $CO_2$ sensor.

8 Claims, 26 Drawing Sheets

(51) Int. Cl.

| | | |
|---|---|---|
| *H01M 8/04186* | (2016.01) | |
| *H01M 8/1009* | (2016.01) | |
| *B01J 31/02* | (2006.01) | |
| *H01M 4/86* | (2006.01) | |
| *C25B 3/04* | (2006.01) | |
| *C25B 9/08* | (2006.01) | |
| *C25B 1/00* | (2006.01) | |
| *C25B 3/00* | (2006.01) | |
| *H01M 8/10* | (2016.01) | |
| *H01M 8/04* | (2016.01) | |
| *G01N 33/00* | (2006.01) | |
| *H01M 10/42* | (2006.01) | |

(52) U.S. Cl.
CPC ....... *B01J 31/0278* (2013.01); *B01J 31/0281* (2013.01); *B01J 31/0284* (2013.01); *B01J 31/0288* (2013.01); *B01J 31/0291* (2013.01); *C25B 1/00* (2013.01); *C25B 3/00* (2013.01); *C25B 3/04* (2013.01); *C25B 9/08* (2013.01); *H01M 4/8652* (2013.01); *H01M 4/8663* (2013.01); *H01M 4/90* (2013.01); *H01M 4/92* (2013.01); *H01M 4/921* (2013.01); *B01J 31/0268* (2013.01); *B01J 2231/62* (2013.01); *G01N 33/004* (2013.01); *H01M 8/04186* (2013.01); *H01M 8/1009* (2013.01); *H01M 10/4235* (2013.01); *Y02E 60/50* (2013.01)

(56) References Cited

U.S. PATENT DOCUMENTS

| | | | |
|---|---|---|---|
| 2,996,359 A | | 8/1961 | Mossman et al. |
| 3,959,094 A | | 5/1976 | Steinberg |
| 4,207,151 A | | 6/1980 | Franke et al. |
| 4,240,882 A | | 12/1980 | Ang et al. |
| 4,315,753 A | | 2/1982 | Bruckenstein et al. |
| 4,474,652 A | | 10/1984 | Brown et al. |
| 4,523,981 A | * | 6/1985 | Ang ................ C25B 1/003 204/157.15 |
| 4,545,872 A | | 10/1985 | Sammells et al. |
| 4,595,465 A | | 6/1986 | Ang et al. |
| 4,608,132 A | | 8/1986 | Sammells |
| 4,608,133 A | | 8/1986 | Morduchowitz et al. |
| 4,609,440 A | | 9/1986 | Frese, Jr. et al. |
| 4,609,441 A | | 9/1986 | Frese, Jr. et al. |
| 4,620,906 A | | 11/1986 | Ang |
| 4,668,349 A | | 5/1987 | Cueller et al. |
| 4,673,473 A | | 6/1987 | Ang et al. |
| 4,756,807 A | | 7/1988 | Meyer et al. |
| 4,771,708 A | | 9/1988 | Douglas, Jr. |
| 4,789,442 A | | 12/1988 | Nakagawa et al. |
| 4,818,353 A | | 4/1989 | Langer et al. |
| 4,879,070 A | | 11/1989 | Kent |
| 4,968,393 A | * | 11/1990 | Mazur et al. ................ 205/352 |
| 5,064,733 A | | 11/1991 | Krist et al. |
| 5,071,526 A | | 12/1991 | Pletcher et al. |
| 5,089,661 A | | 2/1992 | Maspero et al. |
| 5,206,433 A | | 4/1993 | Hohenschutz et al. |
| 5,284,563 A | | 2/1994 | Fujihira et al. |
| 5,294,740 A | | 3/1994 | Kiefer et al. |
| 5,334,759 A | | 8/1994 | Lippert et al. |
| 5,362,367 A | * | 11/1994 | Dapperheld ............. C25B 3/04 205/440 |
| 5,382,332 A | | 1/1995 | Fujihira et al. |
| 5,639,910 A | | 6/1997 | Ikariya et al. |
| 5,709,789 A | | 1/1998 | Shay et al. |
| 5,763,622 A | | 6/1998 | Podszun et al. |
| 5,804,045 A | | 9/1998 | Orillon et al. |
| 5,879,915 A | | 3/1999 | Loubiere et al. |
| 5,928,806 A | | 7/1999 | Olah et al. |
| 5,952,540 A | | 9/1999 | Lee et al. |
| 6,024,855 A | | 2/2000 | Sharifan et al. |
| 6,099,990 A | * | 8/2000 | Denton et al. ............. 429/231.8 |
| 6,391,818 B1 | * | 5/2002 | Bonsel ................ B01J 35/0013 502/159 |
| 6,429,333 B1 | | 8/2002 | Saari et al. |
| 6,660,680 B1 | | 12/2003 | Hampden-Smith et al. |
| 6,706,657 B2 | | 3/2004 | Commereuc et al. |
| 6,713,649 B1 | | 3/2004 | Hladiy et al. |
| 6,841,700 B2 | | 1/2005 | Auer et al. |
| 6,849,764 B2 | | 2/2005 | Gurkaynak et al. |
| 6,867,329 B2 | | 3/2005 | Auer et al. |
| 6,906,222 B2 | | 6/2005 | Slany et al. |
| 6,955,743 B2 | | 10/2005 | Rousu et al. |
| 6,987,134 B1 | | 1/2006 | Gagnon |
| 6,992,212 B2 | | 1/2006 | Zehner et al. |
| 7,081,547 B2 | | 7/2006 | Fujimoto et al. |
| 7,157,404 B1 | | 1/2007 | Jun et al. |
| 7,241,365 B2 | | 7/2007 | Auer et al. |
| 7,253,316 B2 | | 8/2007 | Pastre et al. |
| 7,323,593 B2 | | 1/2008 | Adami et al. |
| 7,351,860 B2 | | 4/2008 | Adami et al. |
| 7,420,088 B2 | | 9/2008 | Karl et al. |
| 7,459,590 B2 | | 12/2008 | Olah et al. |
| 7,479,570 B2 | | 1/2009 | Ogo et al. |
| 7,605,293 B2 | | 10/2009 | Olah et al. |
| 7,608,743 B2 | | 10/2009 | Olah et al. |
| 7,612,233 B2 | | 11/2009 | Hauk et al. |
| 7,618,725 B2 | | 11/2009 | Masel et al. |
| 7,704,369 B2 | | 4/2010 | Olah et al. |
| 8,313,634 B2 | | 11/2012 | Bocarsly et al. |
| 8,592,633 B2 | | 11/2013 | Cole et al. |
| 2004/0031685 A1 | | 2/2004 | Anderson et al. |
| 2006/0096871 A1 | | 5/2006 | Manoukian et al. |
| 2006/0234174 A1 | | 10/2006 | Burrahm et al. |
| 2006/0235091 A1 | | 10/2006 | Olah et al. |
| 2007/0036706 A1 | | 2/2007 | Ogo et al. |
| 2007/0045125 A1 | | 3/2007 | Hartvigsen et al. |
| 2007/0187247 A1 | | 8/2007 | Lackner et al. |
| 2008/0039538 A1 | | 2/2008 | Olah et al. |
| 2008/0103040 A1 | | 5/2008 | Rodriguez et al. |
| 2008/0223727 A1 | | 9/2008 | Oloman et al. |
| 2009/0014336 A1 | | 1/2009 | Olah et al. |
| 2009/0016948 A1 | | 1/2009 | Young |
| 2009/0289211 A1 | | 11/2009 | Fujioka et al. |
| 2010/0132556 A1 | | 6/2010 | Constantz et al. |
| 2010/0133120 A1 | * | 6/2010 | Varney et al. ............. 205/785.5 |
| 2010/0135865 A1 | | 6/2010 | Constantz et al. |
| 2010/0137457 A1 | | 6/2010 | Kaplan |
| 2010/0187123 A1 | | 7/2010 | Bocarsly et al. |
| 2010/0193370 A1 | | 8/2010 | Olah et al. |
| 2010/0276287 A1 | | 11/2010 | Manoukian et al. |
| 2011/0114501 A1 | | 5/2011 | Teamey et al. |
| 2011/0114502 A1 | | 5/2011 | Cole et al. |
| 2011/0114503 A1 | | 5/2011 | Sivasankar et al. |
| 2011/0114504 A1 | | 5/2011 | Sivasankar et al. |
| 2011/0226632 A1 | | 9/2011 | Cole et al. |
| 2011/0237830 A1 | * | 9/2011 | Masel ............................ 562/550 |

FOREIGN PATENT DOCUMENTS

| | | | |
|---|---|---|---|
| DE | 183856 C | | 1/1906 |
| DE | 19754304 | * | 6/1999 |
| EP | 0012215 A | | 6/1980 |
| EP | 0293230 | * | 11/1988 ............. G01N 27/56 |
| EP | 0293230 A | | 11/1988 |
| EP | 0323300 A | | 7/1989 |
| GB | 2230782 A | | 10/1990 |
| JP | S59-219485 A | | 12/1984 |
| JP | H05-093290 A | | 4/1993 |
| JP | 2009-511740 A | | 3/2009 |
| JP | 201217300 | | 1/2012 |
| WO | 2008110830 A | | 9/2008 |
| WO | 2010007602 | | 1/2010 |
| WO | WO 2010014684 | * | 2/2010 |
| WO | 2010063626 A | | 6/2010 |
| WO | 2011120021 A | | 9/2011 |

(56) References Cited

FOREIGN PATENT DOCUMENTS

| WO | 2012006240 A | 1/2012 |
|---|---|---|
| WO | 2013006711 | 1/2013 |

OTHER PUBLICATIONS

Masel, R., "Chemical Kinetics and Catalysis", Wiley (2001), pp. 702-742.
Morris, A. et al., "Electrocatalytic carbon dioxide activation: The rate-determining step of pyridinium-catalyzed CO2 reduction", Chem. Sus. Chem, 4(2011), p. 191-196.
Noda, H. et al., "Electrochemical reduction of carbon dioxide at various metal electrodes in aqueous potassium hydrogen carbonate solution", Bull. Chem. Soc. Japan 63 (1990), pp. 2459-2462.
Ogura, K. et al., "Selective formation of ethylene from CO2 by catalytic electrolysis at a three-phase interface", Prepr. Pap.—Am. Chem. Soc., Div. Fuel Chem. 49 (2004), pp. 9-10.
Ogura, K. et al., "Reduction of CO2 to ethylene at three-phase interface effects of electrode substrate and catalytic coating", Journal of the Electrochemical Society 152 (2005), pp. D213-D219.
Ogura, K et al., "CO2 attraction by specifically adsorbed anions and subsequent accelerated electrochemical reduction", Electrochimica Acta 56 (2010), pp. 381-386.
Ohya, S. et al., "Electrochemical reduction of CO2 in methanol with aid of CuO and Cu2O", Catalysis Today 148 (2009), p. 329-334.
Oloman, C. et al., "Electrochemical processing of carbon dioxide", ChemSusChem 1(2008), pp. 385-391.
O'Mahony, A.M. et al., "The electrochemical reduction of hydrogen sulfide on platinum in several room temperature ionic liquids", The Journal of Physical Chemistry C112 (2008), pp. 7725-7730.
Pease, R.N. et al., "The catalytic combination of ethylene and hydrogen in the presence of metallic copper. III. Carbon monoxide as a catalyst poison", J. Am. Chem. Soc. 47 (1925), pp. 1235-1240.
Perez, E.R. et al., "In situ FT-IR and ex situ EPR analysis for the study of the electroreduction of carbon dioxide in N,N-dimethylformamide on a gold interface", Journal of Electroanalytical Chemistry 578 (2005), pp. 87-94.
Podlovchenko, B.I. et al., "Electroreduction of carbon dioxide on palladium electrodes at potentials higher than the reversible hydrogen potential", Journal of Electroanalytical Chemistry 373 (1994), pp. 185-187.
Popic, J.P. et al., "Reduction of carbon dioxide on ruthenium oxide and modified ruthenium oxide electrodes in 0.5 M NaHCO3", Journal of Electroanalytical Chemistry 421 (1997), pp. 105-110.
Qu, J. P. et al., "Electrochemical reduction of CO2 on RuO2/TiO2 nanotubes composite modified Pt electrode", Electrochimica Acta 50 (2005), pp. 3576-3580.
Raebiger, J.W. et al., "Electrochemical Reduction of CO2 to CO Catalyzed by a Bimetallic Palladium Complex", Organometallics 25 (2006), pp. 3345-3351.
Rakowski DuBois, M. et al., "Development of molecular electrocatalysts for CO2 reduction and H2 production/oxidation", Acc. Chem. Res. 42 (2009), pp. 1974-1982.
Ramirez, G. M. et al., "A supramolecular cobalt-porphyrin-modified electrode, toward the electroreduction of CO2", Journal of Coordination Chemistry 57 (2004), pp. 249-255.
Rezaei, B. et al., "Effects of tetrabutylammonium hydrogen sulfate as an electrolyte additive on the electrochemical behavior of lead acid battery", Journal of Solid State Electrochemistry 12 (2008), pp. 1663-1671.
Rezaei, B. et al., "Application of ionic liquids as an electrolyte additive on the electrochemical behavior of lead acid battery", Journal of Power Sources 187 (2009), pp. 605-612.
Saeki, T. et al., "Electrochemical reduction of liquid CO2. Drastic enhancement of current density", Journal of the Electrochemical Society 141 (1994), pp. L130-L132.
Saeki, T. et al., "Electrochemical reduction of CO2 with high current density in a CO2 + methanol medium at various metal electrodes", Journal of Electroanalytical Chemistry 404 (1996), pp. 299-302.

Seshadri, G. et al., "A new homogeneous electrocatalyst for the reduction of carbon dioxide to methanol at low overpotential", J. Electroanalytical Chemistry 372 (1994), p. 145-150.
Silvester, D.S. et al., "Electrochemistry in room temperature ionic liquids: A review and some possible applications", Z. Phys. Chem. 220 (2006), pp. 1247-1274.
Silvester, D.S. et al., "Electrochemical reduction of benzoic acid and substituted benzoic acids in some room temperature ionic liquids", The Journal of Physical Chemistry C112 (2008), pp. 12966-12973.
Smolinka, T. et al., "CO2 reduction on Pt electrocatalysts and its impact on H2 oxidation in CO2 containing fuel cell feed gas—A combined in situ infrared spectroscopy, mass spectrometry and fuel cell performance study", Electrochimica Acta 50 (2005), pp. 5189-5199.
Star, A. et al., "Nanoelectric carbon dioxide sensors", Advanced Materials 16 (2004), pp. 2049-2051.
Subramanian, K. et al., "Electrochemical membrane reactor for the reduction of carbon dioxide to formate", Journal of Applied Electrochemistry 37 (2007), pp. 255-260.
Sun, J. et al., "Hydroxyl-functionalized ionic liquid: a novel efficient catalyst for chemical fixation of CO2 to cyclic carbonate", Tetrahedron Letters 49 (2008), pp. 3588-3591.
Sung, Y.-E. et al., "Structure of chemisorbed sulfur on a Pt(III) electrode", Journal of the American Chemical Society 119 (1997), pp. 194-200.
Udupa, K.S. et al., "Electrolytic reduction of carbon dioxide to formic acid", Electrochimica Acta 16 (1971), pp. 1593-1598.
Wong, W.L. et al., "A robust ionic liquid as reaction medium and efficient organocatalyst for carbon dioxide fixation", ChemSusChem 1 (2008), pp. 67-70.
Xu, X. et al., "Effects of imidazolium salts as cocatalysts on the copolymerization of CO2 with epoxides catalyzed by (salen)CrIIICl complex", Polymer 48 (2007), pp. 3921-3924.
Yan, T. et al., "Adsorption of CO2 on the rutile (110) surface in ionic liquid. A molecular dynamics simulation", J. Phys. Chem. C 113 (2009), pp. 19389-19392.
Yang, H. et al., "Electrochemical activation of carbon dioxide in ionic liquid: synthesis of cyclic carbonates at mild reaction conditions", Chem. Commun. (2002), pp. 274-275.
Yano, H. et al., "Selective electrochemical reduction of CO2 to ethylene at a three-phase interface on copper(I) halide-confined Cu-mesh electrodes in acidic solutions of potassium halides", Journal of Electroanalytical Chemistry 565 (2004), pp. 287-293.
Yano, J. et al., "Selective ethylene formation by pulse-mode electrochemical reduction of carbon dioxide using copper and copper-oxide electrodes", Journal of Solid State Electrochemistry 11 (2006), pp. 554-557.
Yano, M. et al., "Effects of additives in zinc alloy powder on suppressing hydrogen evolution", Journal of Power Sources 74 (1998), pp. 129-134.
Yoshizawa-Fujita, M. et al., "A new class of proton-conducting ionic plastic crystals based on organic cations and dihydrogen phosphate", Electrochemistry Communications 9 (2007), pp. 1202-1205.
Yuan, D. et al., "Electrochemical activation of carbon dioxide for synthesis of dimethyl carbonate in an ionic liquid", Electrochimica Acta 54 (2009), pp. 2912-2915.
Zhang, L. et al., "Electrochemical activation of CO2 in ionic liquid (BMIMBF4): synthesis of organic carbonates under mild conditions", Green Chemistry 10 (2008), pp. 202-206.
Zhang, S. et al., "Chiral ionic liquids improved the asymmetric cycloaddition of CO2 to epoxides", Green Chem. 11 (2009), pp. 935-938.
Zhang, Z. et al., "Hydrogenation of carbon dioxide is promoted by a task-specific ionic liquid", Angew. Chem. Int. Ed. 47 (2008), pp. 1127-1129.
Zhang, Z. et al., "Hydrogenation of CO2 to formic acid promoted by a diamine-functionalized ionic liquid", ChemSusChem 2 (2009), pp. 234-238.
Zhao, G. et al., "Electrochemical reduction of supercritical carbon dioxide in ionic liquid 1-n-butyl-3-methylimidazolium hexafluorophosphate", Journal of Supercritical Fluids 32 (2004), pp. 287-291.

(56) References Cited

OTHER PUBLICATIONS

Danly, D., "Development and commercialization of the Monsanto electrochemical adiponitrile process", J Electrochemical Soc. 131 (1984), pp. 435C-442C.

Derien, S. et al., "Activation of carbon dioxide: nickel-catalyzed electrochemical carboxylation of diynes", J. Organic Chem. vol. 58. No. 9 (1993), pp. 2578-2588.

DuBois, D. et al., "Electrochemical reduction of carbon dioxide catalyzed by [Pd(triphosphine)(solvent)](BF4)2 complexes: synthetic and mechanistic studies", J. Am. Chem. Soc., vol. 113. No. 23 (1991), pp. 8753-8764.

Fisher, B. et al., "Electrocatalytic reduction of carbon dioxide by using macrocycles of nickel and cobalt", J. Am. Chem. Soc., vol. 102, No. 24 (1980), pp. 7361-7363.

Fukuzumi, S.,"Bioinspired Energy Conversion Systems for Hydrogen Production and Storage", Eur. J. Inorg. Chem., vol. 2008. No. 9. (2008), pp. 1351-1362.

International Search Report issued on Jul. 6, 2011, in connection with PCT/2011/030098.

Li, W., "Electrocatalytic Reduction of CO2 to Small Organic Molecule Fuels on Metal Catalysts", Advances in CO2 Conversion and Utilization (2010), pp. 55-76.

Ma, J. et al., "A short review of catalysis for CO2 conversion", Catal. Today 148 (2009), pp. 221-231.

Morris, A. et al., "Electrocatalytic carbon dioxide activation: The rate-determining step of pyridinium-catalyzed CO2 reduction", Chem. Sus. Chem, 4(2011), pp. 191-196.

Welton, T., "Room-Temperature Ionic Liquids. Solvents for Synthesis and Catalysis". Chem. Revs., vol. 99, No. 8 (1999), pp. 2071-2083.

Zhu, A. "Supported cholinechloride/urea as a heterogeneous catalyst for chemical fixation of carbon dioxide to cyclic carbonates", Green Chemistry. vol. 9 (2007), pp. 169-172.

Written Opinion of the International Searching Authority issued on Sep. 26, 2012, in connection with PCT/US2011/030098.

Azuma, M. et al., "Electrochemical reduction of carbon dioxide on various metal, electrodes in low-temperature aqueous KHCO3 media", J. Electrochem. Soc. 137 (1990), pp. 1772-1778.

Barrosse-Antle, L. et al., "Reduction of carbon dioxide in 1-butyl-3-methylimidazolium acetate", Chem. Commun. (2009), pp. 3744-3746.

Begum, A. et al., "Electrocatalysis of CO2 reduction by ruthenium benzothiazole and bithiazole complexes", Electrochemistry Communications 9 (2007), pp. 2525-2528.

Bell, A.T., "Basic Research Needs: Catalysis for Energy", U.S. Department of Energy Report PNNL-17214 (2008), p. 69.

Cahill, L. et al., "Investigation of proton dynamics and the proton transport pathway in choline dihydrogen phosphate using solid-state NMR", Physical Chemistry Chemical Physics 12 (2010), pp. 5431-5438.

Chandrasekaran, K. et al., "In-situ spectroscopic investigation of adsorbed intermediate radicals in electrochemical reactions: carbon dioxide CO2—on platinum", Surface Science 185 (1987), pp. 495-514.

Chaplin, R.P.S. et al., "Effects of process conditions and electrode material on reaction pathways for carbon dioxide electroreduction with particular reference to formate formation", Journal of Applied Electrochemistry 33 (2003), pp. 1107-1123.

Cheung, K.C. et al., "Electrocatalytic reduction of carbon dioxide by a polymeric film of rhenium tricarbonyl dipyridylamine", Journal of Organometallic Chemistry 694 (2009), pp. 2842-2845.

Chu, D. et al., "Fixation of CO2 by electrocatalytic reduction and electropolymerization in ionic liquid-H20 solution", ChemSusChem 1 (2008), pp. 205-209.

Cole, E. et al., "Using a one-electron shuttle for the multielectron reduction of CO2 to methanol: kinetic, mechanism, and structural insights", J. Am. Chem. Soc. 132 (2010), pp. 11539-11551.

Danly, D.E, "Development and commercialization of the Monsanto electrochemical adiponitrile process", J. Electrochemical Soc. 131 (1984).

Davis, Jr., J.H. et al., "Commercially available salts as building blocks for new ionic liquids", ACS Symp. Ser. 856 (2003), pp. 100-107.

Delacourt, C. et al., "Design of an electrochemical cell making syngas (CO+H2−) from CO2 and H2O reduction at room temperature", Journal of the Electrochemical Society 155 (2008), pp. B42-B49.

Delacourt, C. et al., "Mathematical modeling of a cation-exchange membrane containing two cations", Journal of the Electrochemical Society 155 (2008), pp. B1210-B1217.

DeWulf, D.W. et al., "The electrochemical reduction of CO2 to CH4 and C2H4 at Cu/Nafion electrodes (solid polymer electrolyte structures)", Catalysis Letters 1(1988), pp. 73-80.

DeWulf, D.W. et al., "Electrochemical and surface studies of carbon dioxide reduction to methane and ethylene at copper electrodes in aqueous solutions", Journal of the Electrochemical Society 136 (1989), pp. 1686-1691.

Dietz, H. et al., "Influence of substituted benzaldehydes and their derivatives as inhibitors for hydrogen evolution in lead/acid batteries", Journal of Power Sources 53 (1995), pp. 359-365.

Dube, P. et al., "Influence of adsorption processes on the CO2 electroreduction: An electrochemical mass spectrometry study", Journal of Electroanalytical Chemistry 582 (2005), pp. 230-240.

DuBois, D. in A. Bard, ed., "Encyclopedia of Electrochemistry", 7a, Springer (2006), p. 202-225.

Eggins, B.R. et al., "Voltammetry of carbon dioxide. Part 1. A general survey of voltammetry at different electrode materials in different solvents", J. Electroanalytical Chem. 148 (1983), pp. 17-24.

Eggins, B.R. et al., "Improved yields of oxalate, glyoxylate and glycolate from the electrochemical reduction of carbon dioxide in methanol", Journal of Applied Electrochemistry 27 (1997), pp. 706-712.

Franklin, T.C. et al., "The effect of quaternary ammonium salts on the anodic oxidation of ethanol", Surface Technology 24 (1985), pp. 143-155.

Furuya, N. et al., "High performance Ru—Pd catalysts for CO2 reduction at gas-diffusion electrodes", Journal of Electroanalytical Chemistry 431 (1997), pp. 39-41.

Gattrell, M. et al. "A review of the aqueous electrochemical reduction of CO2 to hydrocarbons at copper", Journal of Electroanalytical Chemistry 594 (2006), pp. 1-19.

Gattrell, M. et al., "Electrochemical reduction of CO2 to hydrocarbons to store renewable electrical energy and upgrade biogas", Energy Conversion Management 48 (2007), pp. 1255-1265.

Haerens, K. et al., "Electrochemical decomposition of choline chloride based ionic liquid analogues", Green Chemistry 11 (2009), pp. 1357-1365.

Himeda, Y., "Conversion of CO2 into formate by homogeneously catalyzed hydrogenation in water: tuning catalytic activity and water solubility through the acid-base equilibrium of the ligand", European Journal of Inorganic Chemistry (2007), pp. 3927-3941.

Hori, Y. et al., "Electrochemical evidence of intermediate formation of adsorbed carbon monoxide in cathodic reduction of carbon dioxide at a nickel electrode", Electrochimica Acta 35 (1990), pp. 1777-1780.

Hori, Y. et al., "Electrochemical reduction of carbon dioxide at various series of copper single crystal electrodes", Journal of Molecular Catalysis A: Chemical 199 (2003), pp. 39-47.

Hori, Y., "Electrochemical CO2 reduction on metal electrodes", Modern Aspects of Electrochemistry 42 (2008), pp. 89-189.

Hoshi, N. et al., "Electrochemical reduction of CO2 on single crystal electrodes of Ag(111), Ag(100), and Ag(110)", Journal of Electroanalytical Chemistry 440 (1997), pp. 283-286.

Ikeda, S. et al., "Zinc ion effect on electrochemical reduction of carbon dioxide at zinc electrode in aqueous solutions", Electrochemistry (Tokyo) 67 (1999), pp. 27-33.

Ikeda, S. et al., "Electrochemical reduction of carbon dioxide using gas diffusion electrodes loaded with fine catalysts", Nanoscience and Nanotechnology (2008), pp. 108-113.

Innocent, B. et al., "Electro-reduction of carbon dioxide to formate on lead electrode in aqueous medium", Journal of Applied Electrochemistry 39 (2009), pp. 227-232.

(56) References Cited

OTHER PUBLICATIONS

Jiang, T. et al., "Solvent-free synthesis of substituted ureas from CO2 and amines with a functional ionic liquid as the catalyst", Green Chem. 10 (2008), pp. 465-469.

Jitaru, M., "Electrochemical carbon dioxide reduction—Fundamental applied topics (Review)", Journal of the University of Chemical Technology and Metallurgy 42 (2007), p. 333-344.

Kaneco, S. et al., "Electrochemical reduction of carbon dioxide to ethylene with high Faradaic efficiency at a Cu electrode in CsOH/methanol", Electrochimica Acta 44 (1999), pp. 4701-4706.

Kaneco, S. et al., "Carbon dioxide sequestration technology by electrochemical conversion at cadmium electrode in methanol under mild conditions", Photo/Electrochemistry & Photobiology in Environment, Energy and Fuel (2003), pp. 181-189.

Kaneco, S. et al., "Electrochemical reduction of CO2 in copper particle-suspended methanol", Chemical Engineering Journal 119 (2006), pp. 107-112.

Kaneco, S. et al., "Electrochemical reduction of carbon dioxide to ethylene at a copper electrode in methanol using potassium hydroxide and rubidium hydroxide supporting electrolytes", Electrochimica Acta 51 (2006), pp. 3316-3321.

Kaneco, S. et al., "Electrochemical reduction of CO2 to Methane at the Cu electrode in methanol with sodium supporting salts and its comparison with other alkaline salts", Energy & Fuels 20 (2006), pp. 409-414.

Kaneco, S. et al. "Effect of sodium cation on the electrochemical reduction of CO2 at a copper electrode in methanol", Journal of Solid State Electrochemistry 11 (2007), pp. 490-495.

Kaneco, S. et al., "Photoelectrochemical reduction of CO2 at p-InP electrode in copper particle-suspended methanol", Chemical Engineering Journal 148 (2009), pp. 57-62.

Koleli, F. et al., "Reduction of CO2 under high pressure and high temperature on Pb-granule electrodes in a fixed-bed reactor in aqueous medium", Applied Catalysis A-General 274 (2004), pp. 237-242.

Laitar, D.S. et al., "Efficient homogeneous catalysis in the reduction of CO2 to CO", Journal of the American Chemical Society 127 (2005), pp. 17196-17197.

Lee, C.W. et al., "Studies on suppression of hydrogen evolution reaction for zinc/air fuel cell", Material Science Forums 539-543 (2007), pp. 1427-1430.

Li, H. et al., "Development of a continuous reactor for the electro-reduction of carbon dioxide to formate—Part 1: Process variables", Journal of Applied Electrochemistry 36 (2006), pp. 1105-1115.

Li, H. et al., "Development of a continuous reactor for the electro-reduction of carbon dioxide to formate—Part 2: Scale-up", Journal of Applied Electrochemistry 37 (2007), pp. 1107-1117.

Lukaszewski, M. et al., "Comparative EQCM study on electrooxidation of carbon oxides adsorption products on noble metals and their alloys. Polycrystalline Pd-based systems", Journal of Electroanalytical Chemistry 606 (2007), pp. 117-133.

International Search Report and Written Opinion issued on Feb. 15, 2013 in connection with PCT/US2012/043651.

International Preliminary Report on Patentability issued on Jan. 3, 2013 in connection with International Application No. PCT/US2011/030098.

International Preliminary Report on Patentability issued on Jan. 3, 2013 in connection with International Application No. PCT/US2011/042809.

Kaneco, S. et al., "Electrochemical conversion of carbon dioxide to formic acid on Pb in KOH/methane electrolyte at ambient temperature and pressure", Energy, vol. 23, No. 12 (1998), pp. 1107-1112.

International Search Report and Written Opinion of the International Searching Authority issued on Oct. 31, 2011, in connection with PCT/US2011/042809.

Arenz, M. et al. The effect of the particle size on the kinetics of CO electrooxidation on high surface area Pt catalysts. Journal of the American Chemical Society 127, 6819-6829 (2005).

Blizanac, B. et al., Oxygen Reduction on Silver Low-Index Single-Crystal in Alkaline Solution: Rotating Ring DiskAg (hkl). J. Phys. Chem. 110, 4735-4741 (2006).

Bregoli, L. The influence of platinum crystallite size on the electrochemical reduction of oxygen in phosphoric acid. Electrochimica Acta 23, 489-492 (1978).

Chaplin, R. et al. Effects of process conditions and electrode material on reaction pathways for carbon dioxide electroreduction with particular reference to formate formation. Journal of Applied Electrochemistry 33, 1107-1123 (2003).

Chen, Q. et al., Sun, S. G. & Feliu, J. M. Role of surface defect sites: From Pt model surfaces to shape-controlled nanoparticles. Chemical Science 3, 136-147 (2012).

Cherstiouk, O. et al. Model approach to evaluate particle size effects in electrocatalysis: Preparation and properties of Pt nanoparticles supported on GC and HOPG. Electrochimica Acta 48, 3851-3860 (2003).

Hori, Y. et al. Electrochemical reduction of carbon dioxide at various series of copper single crystal electrodes. Journal of Molecular Catalysis A: Chemical 199, 39-47 (2003).

Hoshi, N. et al. Electrochemical reduction of carbon dioxide at a series of platinum single crystal electrodes. Electrochimica Acta 45, 4263-4270 (2000).

Hoshi, N. et al. Electrochemical reduction of carbon dioxide on kinked stepped surfaces of platinum inside the stereographic triangle. Journal of Electroanalytical Chemistry 540, 105-110 (2003).

Kabbabi, A. et al. Particle size effect for oxygen reduction and methanol oxidation on Pt/C inside a proton exchange membrane. Journal of Electroanalytical Chemistry 373, 251-254 (1994).

Kinge, S. et al.. Dependence of CO oxidation on Pt nanoparticle shape: A shape-selective approach to the synthesis of PEMFC catalysts. Applied Organometallic Chemistry 22, 49-54 (2008).

Kinoshita, K. Particle size effects for oxygen reduction on highly dispersed platinum in acid electrolytes. Journal of the Electrochemical Society 137, 845-848 (1990).

Koper, M. Structure sensitivity and nanoscale effects in electrocatalysis. Nanoscale 3, 2054-2073 (2011).

Lopez-Cudero, A. et al. CO electrooxidation on carbon supported platinum nanoparticles: Effect of aggregation. Journal of Electroanalytical Chemistry 644, 117-126 (2010).

Liu, Y. et al. Observation of surface structural changes of Pt octahedron nanoparticles and its effect in electrocatalysis oxidation of methanol. Catalysis Communications 10, 1244-1247 (2009).

Liu, Z. et al. General rules for predicting where a catalytic reaction should occur on metal surfaces: A density functional theory study of C—H and C—O bond breaking/making on flat, stepped, and kinked metal surfaces. Journal of the American Chemical Society 125, 1958-1967 (2003).

Lukaszewski, M. et al. Electrosorption of carbon dioxide on platinum group metals and alloys—a review. Journal of Solid State Electrochemistry 13, 813-827 (2009).

Maillard, F. et al. Size effects on reactivity of Pt nanoparticles in CO monolayer oxidation: The role of surface mobility. Faraday Discussions 125, 357-377 (2004).

Maillard, F. et al. Influence of particle agglomeration on the catalytic activity of carbon-supported Pt nanoparticles in CO monolayer oxidation. Physical Chemistry Chemical Physics 7, 385-393 (2005).

Meiwes-Broer, K. Work functions of metal clusters. Hyperfine Interactions 89, 263-269 (1994).

Narayanan, R. et al. Catalysis with transition metal nanoparticles in colloidal solution: Nanoparticle shape dependence and stability. Journal of Physical Chemistry B 109, 12663-12676 (2005).

Photinon, K. et al. Thick-Film carbon dioxide sensor via anodic adsorbate stripping technique and its structural dependence. Sensors 9, 7203-7216 (2009).

Rodriguez, P. et al. Specific surface reactions for identification of platinum surface domains: Surface characterization and electrocatalytic tests. Electrochimica Acta 50, 4308-4317 (2005).

Scheijen, F. et al. The electrooxidation of small organic molecules on platinum nanoparticles supported on gold: Influence of platinum deposition procedure. Journal of Solid State Electrochemistry 12, 483-495 (2008).

(56) References Cited

OTHER PUBLICATIONS

Singh, P. et al., Comparison of Oxygen Reduction Reaction at Silver Nanoparticles and Polycrystalline Silver Electrodes in Alkaline Solution. J. Phys. Chem. 116, 10656-10663 (2012).
Smolinka, T. et al. CO2 reduction on Pt electrocatalysts and its impact on H 2 oxidation in CO2 containing fuel cell feed gas—A combined in situ infrared spectroscopy, mass spectrometry and fuel cell performance study. Electrochimica Acta 50, 5189-5199 (2005).
Smolinski, S. et al. Effect of surface order on adsorption of sulfate ions on silver electrodes. Journal of Electroanalytical Chemistry 442, 41-47 (1998).
Sobkowski, J et al. Interaction of sulfate ions with monocrystalline silver electrodes. Colloids Surfaces A: Physicochem. Eng. Aspects 134, 39-45 (1998).
Solla-Gullon, J. et al. Shape dependent electrocatalysis. Annual Reports on the Progress of Chemistry—Section C 107, 263-297 (2011).
Solla-Gullon, J. et al. CO monolayer oxidation on semi-spherical and preferentially oriented (1 0 0) and (1 1 1) platinum nanoparticles. Electrochemistry Communications 8, 189-194 (2006).
Solla-Gullon, J. et al. Shape-dependent electrocatalysis: Methanol and formic acid electrooxidation on preferentially oriented Pt nanoparticles. Physical Chemistry Chemical Physics 10, 3689-3698 (2008).
Takahashi, I. et al. Electrochemical reduction of CO2 at copper single crystal Cu(S)-[n(111) Ã—(111)] and Cu(S)—[n(110) Ã—(100)] electrodes. Journal of Electroanalytical Chemistry 533, 135-143 (2002).
Tian, N. et al. Platinum metal catalysts of high-index surfaces: from single-crystal planes to electrochemically shape-controlled nanoparticles. Journal of Physical Chemistry C 112, 19801-19817 (2008).
Tian, N. et al. Synthesis of tetrahexahedral platinum nanocrystals with high-index facets and high electro-oxidation activity. Science 316, 732-735 (2007).
Tian, N. et al. Direct electrodeposition of tetrahexahedral Pd nanocrystals with high-index facets and high catalytic activity for ethanol electrooxidation. Journal of the American Chemical Society 132, 7580-7581 (2010).
Yano, H. et al. Particle-size effect of nanoscale platinum catalysts in oxygen reduction reaction: An electrochemical and 195Pt EC-NMR study. Physical Chemistry Chemical Physics 8, 4932-4939 (2006).
Yu, D. et al. Carboxylation of Terminal Alkynes with Carbon Dioxide Catalyzed by Poly(N-Heterocyclic Carbene)-Supported Silver Nanoparticles. Adv. Synth. Catal. 354, 969-974 (2012).
Zhou, W. et al. Size effects in electronic and catalytic properties of unsupported palladium nanoparticles in electrooxidation of formic acid. Journal of Physical Chemistry B 110, 13393-13398 (2006).
Perez, J. et al. Particle size effect for ethanol electro-oxidation on Pt/C catalystsin half-cell and in a single direct ethanol fuel cell. Journal of Electroanalytical Chemistry 654, 108-115 (2011).
Rosen, B. et al. Ionic Liquid-Mediated Selective Conversion of CO2 to CO at Low Overpotentials. Science 334, 643-644 (2011).
Urey, H. et al., "Some reactions of atomic hydrogen", Journal of the American Chem. Society 51 (1929), pp. 3286-3290.
Weiss, A. et al., "Formose sugars from formaldehyde", Applied Catalysis 1 (1981), pp. 237-246.

Idriss, H. et al., "Two routes to formaldehyde from formic acid on TiO2, (001) surfaces", Surface Science 348 (1996), pp. 39-48.
Kiss, G. et al., "Palladium-catalyzed reppe carbonylation", Chem. Rev. 101 (2001), pp. 3435-3456.
Jessop, P. et al., "Recent advances in the homogeneous hydrogenation of carbon dioxide", Coordination Chem. Rev. 248 (2004), pp. 2425-2442.
Gazsi, A. et al., "Decomposition and reforming of formic acid on supported Au catalysts: Production of CO-free H2", Journal of Physical Chem. C 115 (2011), pp. 15459-15466.
Sabatier, P. et al., "Chimie Organique.—Sur la decomposition catalytique de l 'acide formique", Comptes Rendus Hebdomadaires Des Seances De L'Academie Dessciences 152 (2011), pp. 1213-1215.
Deng, J. et al., "Linked strategy for the production of fuels via formose reaction", Scientific Reports 3 (2013), p. 1244.
International Search Report and Written Opinion issued on Jun. 17, 2014 in connection with PCT/US2014/018067.
International Preliminary Report on Patentability issued on Jan. 9, 2014 in connection with International Application PCT/US2012/043651.
S. Ikeda, T. Takagi, and K. Ito, "Selective Formation of Formic Acid. Oxalic Add, and Carbon Monoxide by Electrochemical Reduction of Carbon Dioxide", Bull. Chem. Soc. Japan, vol. 60, pp. 2517-2522 (1987).
M. Aulice Scibioh and B. Viswanathan,"Electrochemical Reduction of Carbon Dioxide: A Status Report", Indian Natn. Sci. Acad., vol. 70, A, No. 3, pp. 407-462 (May 2004).
Third-Party Submissions Under 37 CFR 1.290, submitted on Sep. 17 and 18, 2013, in connection with co-owned U.S. Appl. No. 12/830,338, and Concise Description of Relevance for each of the references cited in the Third Party Submissions.
D. Dubois, "Electrochemical Reactions of Carbon Dioxide", Encyclopedia of Electrochemistry, pp. 212 (2007).
International Search Report and Written Opinion issued on May 16, 2014 in connection with PCT/US2013/061506.
Ishida, et al., "High-temperature electrochemical reduction of carbon dioxide using an ionic liquid", The Chem. Soc. of Japan, Proceeding of 82th Autumn Meeting, Sep. 10, 2002, p. 46.
Japanese Office Action dated Jun. 2, 2015 issued in connection with Japanese Application No. 2013-518759.
Chinese Office Action issued on Aug. 5, 2014 in connection with Chinese Application No. 201180023851.2.
Chinese Office Action issued on Oct. 16, 2015 in connection with Chinese Application No. 201180033161.5.
Patent Examination Report issued on Nov. 5, 2014, in connection with Australian patent application No. 2011276362.
Notice of Acceptance issued on Mar. 2, 2016, in connection with Australian patent application No. 2011276362.
Office Action issued on Dec. 22, 2014, in connection with Chinese patent application No. 2013011600390800.
Office Action issued on Oct. 16, 2015, in connection with Chinese patent application No. 2013011600390800.
Notification of Grant issued on Jun. 14, 2016, in connection with Chinese patent application No. 2013011600390800.
Office Action issued on Jun. 2, 2015, in connection with Japanese patent application No. 2013-518759.
Office Action issued on Feb. 16, 2016, in connection with Japanese patent application No. 2013-518759.

\* cited by examiner sarcosines benzamidines serinols

2' amino alcohols
($R_1$ = H, 1' amino alcohols)

norepinepherines isoetarines

CATALYST MIXTURES

CROSS-REFERENCE TO RELATED APPLICATION(S)

This application is related to and claims priority benefits from U.S. Provisional Patent Application Ser. No. 61/484,072 filed May 9, 2011, entitled "Novel Catalyst Mixtures". This application is also related to and claims priority benefits from U.S. Non-Provisional Patent Application Serial No. 12/830,338 filed Jul. 5, 2010, entitled "Novel Catalyst Mixtures" and international patent application No. PCT/US2011/030098, filed Mar. 25, 2011, entitled "Novel Catalyst Mixtures". Each of the '072, '338 and '098 applications is hereby incorporated herein by reference in its entirety.

STATEMENT OF GOVERNMENT INTEREST

This invention was made, at least in part, with U.S. government support under Department of Energy Grant DE-SC0004453. The U.S. government has certain rights in the invention.

FIELD OF THE INVENTION

The field of the invention is electrochemical cells and electrochemistry. The electrochemical cell additives and methods of this invention are applicable, for example, to formic acid fuel cells, carbon dioxide conversion devices or sensors for monitoring carbon dioxide.

BACKGROUND OF THE INVENTION

There is a present need to decrease carbon dioxide ($CO_2$) emissions from industrial facilities. Over the years, a number of electrochemical processes have been suggested for the conversion of $CO_2$ into useful products. Processes for $CO_2$ conversion and the catalysts for them are discussed in U.S. Pat. Nos. 3,959,094; 4,240,882; 4,523,981; 4,545,872; 4,595,465; 4,608,132; 4,608,133; 4,609,440; 4,609,441; 4,609,451; 4,620,906; 4,668,349; 4,673,473; 4,711,708; 4,756,807; 4,818,353; 5,064,733; 5,284,563; 5,382,332; 5,457,079; 5,709,789; 5,928,806; 5,952,540; 6,024,855; 6,660,680; 6,987,134 (the '134 patent); U.S. Pat. Nos. 7,157,404; 7,378,561; 7,479,570; U.S. Patent Application Publication No. US 2008/0223727 A1 (the '727 publication); and papers reviewed by Hori (Modern Aspects of Electrochemistry, 42, 89-189, 2008) ("the Hori review"), Gattrell, et al. (Journal of Electroanalytical Chemistry, 594, 1-19, 2006) ("the Gattrell review"), DuBois (Encyclopedia of Electrochemistry, 7a, 202-225, 2006) ("the DuBois review"), and the papers Li, et al. (Journal of Applied Electrochemistry, 36, 1105-1115, 2006), Li, et al. (Journal of Applied Electrochemistry, 37, 1107-1117, 2007), and Oloman, et al. (ChemSusChem, 1, 385-391, 2008) ("the Li and Oloman papers").

Generally an electrochemical cell 10 contains an anode 50, a cathode 51 and an electrolyte 53 as indicated in FIG. 1. The devices can also include a membrane 52. Catalysts are placed on the anode, and or cathode and or in the electrolyte to promote desired chemical reactions. During operation, reactants or a solution containing reactants is fed into the cell via anode reactant manifold 54 and cathode reactant manifold 55. Then a voltage is applied between the anode and the cathode, to promote an electrochemical reaction.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds. Examples of cathode reactions in the Hori review include:

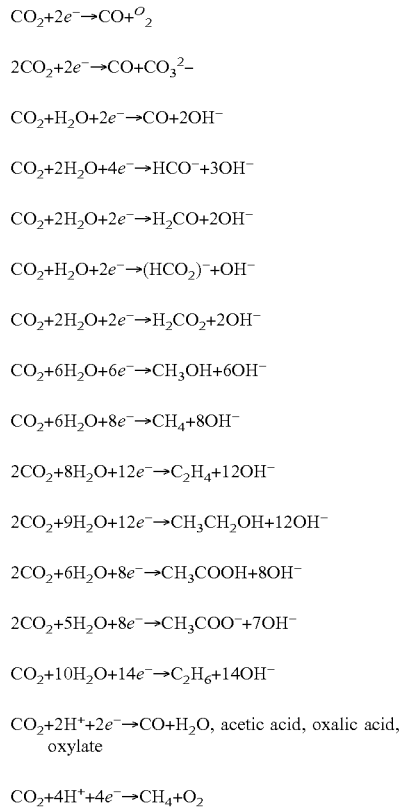

where $e^-$ is an electron. The examples given above are merely illustrative and are not meant to be an exhaustive list of all possible cathode reactions.

Examples of reactions on the anode mentioned in the Hori review include:

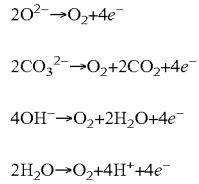

The examples given above are merely illustrative and are not meant to be an exhaustive list of all possible anode reactions.

In the previous literature, catalysts comprising one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd have all shown activity for $CO_2$ conversion. Reviews include Ma, et al. (Catalysis Today, 148, 221-231, 2009), Hori (Modern Aspects of Electrochemistry, 42, 89-189, 2008), Gattrell, et al. (Journal of Electroanalytical Chemistry, 594, 1-19, 2006), DuBois (Encyclopedia of Electrochemistry, 7a, 202-225, 2006) and references therein.

The results in the Hori review show that the conversion of $CO_2$ is only mildly affected by solvent unless the solvent also acts as a reactant. Water can act like a reactant, so reactions in water are different than reactions in non-aqueous solutions. But the reactions are the same in most non-aqueous solvents, and importantly, the overpotentials are almost the same in water and in the non-aqueous solvents.

Zhang, et al. (ChemSusChem, 2, 234-238, 2009) and Chu, et al. (ChemSusChem, 1, pages 205-209, 2008) report $CO_2$ conversion catalyzed by an ionic liquid. Zhao, et al. (The Journal of Supercritical Fluids, 32, pages 287-291, 2004) and Yuan, et al. (Electrochimica Acta 54, pages 2912-2915, 2009) report the use of an ionic liquid as a solvent and electrolyte, but not a co-catalyst, for $CO_2$ electroconversion. Each of these papers is incorporated by reference. Catalyst Today, Volume 48, pages 189-410 November 2009 provides the proceedings of the 10th international conference on $CO_2$ utilization. These pages are incorporated by reference. The catalysts have been in the form of either bulk materials, supported particles, collections of particles, small metal ions or organometallics. Still, according to Bell (A. Bell, Ed., Basic Research Needs, Catalysis For Energy, U.S. Department Of Energy Report PNNL17712, 2008) ("the Bell Report"), "The major obstacle preventing efficient conversion of carbon dioxide into energy-bearing products is the lack of catalyst" with sufficient activity at low overpotentials and high electron conversion efficiencies.

The overpotential is associated with lost energy of the process, and so one needs the overpotential to be as low as possible. Yet, according to the Bell Report, "Electron conversion efficiencies of greater than 50 percent can be obtained, but at the expense of very high overpotentials".

The '134 patent also considers the use of salt (NaCl) as a secondary "catalyst" for $CO_2$ reduction in the gas phase, but salt does not lower the overpotential for the reaction.

A second disadvantage of many of the catalysts is that they also have low electron conversion efficiency. Electron conversion efficiencies over 50% are desirable for practical catalyst systems.

The examples above consider applications for $CO_2$ conversion, but the present invention overcomes limitations of other systems. For example some commercial $CO_2$ sensors use an electrochemical reaction to detect the presence of $CO_2$. At present, these sensors require over 1-5 watts of power, which may be too high for portable sensing applications.

The present invention also considers, for example, new methods to produce or electrochemically react formic acid. Other methods of generating formic acid are discussed in U.S. Pat. Nos. 7,618,725; 7,612,233; 7,420,088; 7,351,860; 7,323,593; 7,253,316; 7,241,365; 7,138,545; 6,992,212; 6,963,909; 6,955,743; 6,906,222; 6,867,329; 6,849,764; 6,841,700; 6,713,649; 6,429,333; 5,879,915; 5,869,739; 5,763,662; 5,639,910; 5,334,759; 5,206,433; 4,879,070; and 4,299,891. These processes do not use $CO_2$ as a reactant.

Formic acid can be used, for example, in fuel cells. It has been shown that the oxidation reaction of formic acid in a fuel cell can be poisoned by organic acids such as acetic acid, as well as by methyl formate or methanol. See, for example, Masel, et al., U.S. Pat. No. 7,618,725 (Low Contaminant Formic Acid Fuel For Direct Liquid Fuel Cell).

Another benefit of the present invention is that it can suppress undesirable side reactions, such as the generation of hydrogen gas from the electrolysis of water in an electrochemical cell. This hydrogen evolution reaction (HER) can reduce the electron conversion efficiency of a desired reaction, and in some instances may present a safety hazard from the buildup of potentially explosive hydrogen gas. In Monsanto U.S. Pat. No. 4,207,151 (Electrohydrodimerization Process Improvement And Improved Electrolyte Recovery Process), Franke, et al. described inhibiting formation of hydrogen at the cathode surface by adding to the aqueous solution a nitrilocarboxylic acid. One such nitrilocarboxylic acid cited is the complexing agent ethylenediaminetetraacetic acid (EDTA). The patent also discloses that the "generation of hydrogen at the cathode is even more significantly inhibited by including in the electrolysis medium a boric acid, a condensed phosphoric acid or an alkali metal or ammonium salt thereof," such as ammonium triphosphate. The process improvement method also discloses incorporating at least a small amount of quaternary ammonium cations in the aqueous phase as a "directive salt", in order to improve the phase partition extraction efficiency for separating the desired product. "In general, there need be only an amount sufficient to provide the desired hydrodimer selectivity (typically at least about 75%) although much higher proportions can be present if convenient or desired." Quaternary ammonium salts can also be used in the process as conductive salts to provide the desired conductivity of the cell electrolyte. A more detailed history of the development of this process is provided by D. E. Danly, "Development and Commercialization of the Monsanto Electrochemical Adiponitrile Process," Journal of the Electrochemical Society, October 1984, pages 435C-442C. This paper indicates that the hydrogen suppression by the addition of the nitrilocarboxylic acid EDTA was accomplished by chelating Fe and Cd anode corrosion products before they could reach the cathode. The paper stated that, "In the absence of EDTA, hydrogen evolution at the cathode increased over a day's operation to the point where it represented greater than 10% loss in cathodic current efficiency."

Rezaei and Taki have recently shown that the quaternary amine tetrabutylammonium hydrogen sulfate (TBAHS) can increase the hydrogen overpotential for the hydrogen evolution reaction (HER) in a lead acid battery that uses Pb—Sb—Sn positive and negative electrode grids. (Behzad Rezaei and Mahmood Taki, "Effects of tetrabutylammonium hydrogen sulfate as an electrolyte additive on the electrochemical behavior of lead acid battery," J. Solid State Electrochem. (2008) 12:1663-1671). Water loss has been high in such batteries because antimony from the positive grid can migrate through the sulfuric acid electrolyte solution and be deposited on the negative plate, where it diminishes the overpotential for hydrogen evolution from the electrolysis of water. TBAHS was selected as a possible electrolyte additive material that might be able to withstand the sulfuric acid electrolyte. Rezaei, et al., similarly investigated ammonium hydrogen sulfate salts of a primary, a secondary, and a tertiary amine, as well as the "aromatic quaternary amine" 1-butyl-3-methylimidazolium hydrogen sulfate (BMIM HS). The results were somewhat inconsistent, particularly for the BMIM HS. Also, the addition of these materials to the battery electrolyte was found to increase the grid corrosion rate. (Behzad Rezaei, Shadpour Mallakpour, and Mahmood Taki, "Application of ionic liquids as an electrolyte additive on the electrochemical behavior of lead acid battery," J. of Power Sources, 187 (2009) 605-612).

Substituted benzaldehydes were studied for suppressing hydrogen evolution to reduce water loss during cycling by Dietz, et al., "Influence of benzaldehydes and their derivatives as inhibitors for hydrogen evolution in lead/acid batteries," Journal of Power Sources, 53, pages 359-365 (1995).

The addition of succinic acid to the electrolyte of a fuel cell was found to greatly increase the hydrogen evolution overpotential and reduce hydrogen generation in the investigation by Lee, et al., "Study on Suppression of Hydrogen Evolution Reaction for Zinc/Air Fuel Cell," Materials Science Forum, Vols. 539-543, pages 1427-1430 (2007).

One recent paper mentions hydrogen evolution from trace amounts of water as a side reaction during electrodeposition of metals from the deep eutectic solvent Ethaline 200 (choline chloride with ethylene glycol). See Haerens, et al., "Electrochemical decomposition of choline chloride based ionic liquid analogues," 2009 Green Chemistry 11 (9), pages 1357-1365.

The quaternary amine salt choline dihydrogen phosphate has recently been investigated as a possible solid state proton exchange membrane for applications such as fuel cells and sensors. See, for example, Yoshizawa-Fujita, et al., "A new class of proton-conducting ionic plastic crystals based on organic cations and dihydrogen phosphate," 2007 Electrochemistry Communications 9 (5), pages 1202-1205, and Cahill, et al., "Investigation of proton dynamics and the proton transport pathway in choline dihydrogen phosphate using solid-state NMR," 2010 Physical Chemistry Chemical Physics 12 (20), pages 5431-5438.

In light of the above, there still exists a need for cost effective methods to suppress undesired reactions such as the hydrogen evolution reaction in applications such as electrochemical cells, fuel cells, and sensors, while simultaneously enhancing the rate or yield of the desired reaction(s). In particular there is a need to suppress the hydrogen evolution reaction using additives that do not contain carboxylate groups, since carboxylic acids and their salts inhibit desired reactions such as formic acid electrooxidation or carbon dioxide conversion.

SUMMARY OF THE INVENTION

A novel catalyst mixture overcomes one or more of the limitations of low rates, high overpotentials and low electron conversion efficiencies (namely, selectivities) for catalytic reactions, such as those in electrochemical cells, fuel cells, and batteries, as well as overcoming the problem of the high power required for operating certain chemical sensors. At the same time, the novel catalyst mixture can suppress undesired side reactions, such as the production of hydrogen gas from the electrolysis of water. This suppression is accomplished by increasing the overpotential of the undesired reaction. The catalyst mixture includes at least one Catalytically Active Element, and at least one Helper Catalyst. The Helper Catalyst can include, for example salts of choline, or choline derivatives. When the Catalytically Active Element and the Helper Catalyst are combined, the rate and/or selectivity of a chemical reaction can be enhanced over the rate seen in the absence of the Helper Catalyst. For example, the overpotential for electrochemical conversion of carbon dioxide can be substantially reduced, and the current efficiency (namely, selectivity) for $CO_2$ conversion can be substantially increased. Similarly, the electrooxidation of formic acid in water (as occurs in a formic acid fuel cell) can be enhanced while the side reaction of hydrogen evolution from the water is minimized.

In one aspect, the present invention includes an electrochemical cell with a fluid phase, the cell including a hydrogen evolution suppressor material that includes at least one positively charged nitrogen or phosphorus atom in its structure. The nitrogen could be, for example, part of a quaternary amine group. The hydrogen suppressor molecules can also have at least one polar group selected from the group consisting of —OR, —COR, —COOR, —$NR_2$, —$PR_2$, —SR and X, where each R independently can be H or a linear, branched, or cyclic $C_1$-$C_4$ aliphatic group, —COOR is not a carboxylic acid, and X is a halide, such as chlorine or fluorine. In particular, the polar group or groups can include at least one hydroxyl group and or at least one halide atoms, but these molecules would preferably not contain a carboxylic acid group or be ionic salts of a carboxylic acid. An example of such a hydrogen evolution suppressor molecule would be a salt including the choline cation, or a choline derivative of the form $R_1R_2R_3N^+(CH_2)_nOH$ or $R_1R_2R_3N^+(CH_2)_nCl$, wherein n=1-4, and $R_1$, $R_2$, and $R_3$ are independently selected from the group consisting of aliphatic $C_1$-$C_4$ groups, —$CH_2OH$, —$CH_2CH_2OH$, —$CH_2CH_2CH_2OH$, —$CH_2CHOHCH_3$, —$CH_2COH$, —$CH_2CH_2COH$, and —$CH_2COCH_3$ and molecules where one of more chlorine or fluorine is substituted for hydrogen in aliphatic $C_1$-$C_4$ groups, —$CH_2OH$, —$CH_2CH_2OH$, —$CH_2CH_2CH_2OH$, —$CH_2CHOHCH_3$, —$CH_2COH$, —$CH_2CH_2COH$, and —$CH_2COCH_3$. The reactants or the products of the reaction can include at least one of the following: $CO_2$, $CO$, $CO_3^{2-}$, $HCO_3^-$, $OH^-$, $HCO^-$, $H_2CO$, $(HCO_2)^-$, $H_2CO_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, $(COO^-)_2$. The electrochemical cell could be, for example, a fuel cell, a chemical sensor, or a battery. The electrochemical cell can also include a Catalytically Active Element, which could be at least one of the following chemical elements: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, C, In, Sn, Tl, Pb, Bi, Sb, Te, U, Sm, Tb, La, Ce, Nd.

In another aspect, the present invention includes a method of suppressing hydrogen gas evolution from water that might be present in an electrochemical cell, the method including the steps of: (i) providing an electrochemical cell having a fluid phase and a negative electrode, (ii) providing in the fluid phase a hydrogen evolution suppressor as described above that includes a cation containing at least one positively charged nitrogen or phosphorus group and at least one polar group selected from the group consisting of —OR, —COR, —COOR, —$NR_2$, —$PR_2$, —SR and X, where each R independently can be H or a linear, branched, or cyclic $C_1$-$C_4$ aliphatic group, —COOR is not a carboxylic acid, and X is a halide, and (iii) operating the electrochemical cell with the negative electrode at a potential that would cause hydrogen gas evolution from water that might be present in an electrochemical cell if the hydrogen evolution suppressor were not present. The electrical cell could be as described in the previous paragraph.

In yet another aspect, the present invention includes an electrochemical cell that includes an Active Element, Helper Catalyst Mixture, in which the addition of the Helper Catalyst improves the rate or yield of a desired reaction, while simultaneously decreasing the rate or yield of an undesired reaction. The undesired reaction may be the evolution of hydrogen gas. The Helper Catalyst can include a cation containing at least one positively charged nitrogen or phosphorus group and at least one polar group selected from the group consisting of —OR, —COR, —COOR, —$NR_2$, —$PR_2$, —SR and X, where each R independently can be H or a linear, branched, or cyclic $C_1$-$C_4$ aliphatic group, —COOR is not a carboxylic acid, and X is a halide. For example, the cation could contain at least one quaternary amine group and at least one halide or hydroxyl group, but no carboxylic acid group or carboxylic acid salt. The quaternary amine cation can be, for example, choline cations, or choline cation derivatives of the form $R_1R_2R_3N^+(CH_2)_nOH$ or $R_1R_2R_3N^+(CH_2)_nCl$, where n=1-4, and $R_1$, $R_2$, and $R_3$ are independently selected from the group that includes aliphatic $C_1$-$C_4$ groups, —$CH_2OH$, —$CH_2CH_2OH$, —CH$_2$CH$_2$CH$_2$OH—CH$_2$CHOHCH$_3$, —CH$_2$COH, —CH$_2$CH$_2$COH, and —CH$_2$COCH$_3$ and molecules where one of more chlorine or fluorine is substituted for hydrogen in aliphatic C$_1$-C$_4$ groups, —CH$_2$OH, —CH$_2$CH$_2$OH, —CH$_2$CH$_2$CH$_2$OH, —CH$_2$CHOHCH$_3$, —CH$_2$COH, —CH$_2$CH$_2$COH, and —CH$_2$COCH$_3$ In still another aspect of the present invention, this application discloses a catalyst mixture having a Catalytically Active Element and a Helper Catalyst in which the Helper Catalyst also functions as a director molecule. The Helper Catalyst/director molecule would be a molecule containing at least one positively charged group and at least one group for surface attachment. The positively charged group can be, for example, a phosphonium group, or an amine group, such as a quaternary amine. The group for surface attachment can be, for example, a polar group selected from the group consisting of —OR, —COR, —COOR, —NR$_2$, —PR$_2$, —SR and X, where each R independently can be H or a linear, branched, or cyclic C$_1$-C$_4$ aliphatic group, —COOR is not a carboxylic acid, and X is a halide.

In addition, another aspect of the present invention is a method of operating an electrochemical cell at negative potentials with respect to the reversible hydrogen electrode (RHE). This method includes the steps of: (i) providing an electrochemical cell having a fluid phase and a negative electrode, (ii) providing in the fluid phase a hydrogen evolution suppressor comprising a cation, and (iii) operating the electrochemical cell with the negative electrode at a negative potential with respect to RHE. The cation would have at least one positively charged group and at least one group for surface attachment. Again, the positively charged group can be, for example, a phosphonium group, or an amine group, such as a quaternary amine. The group for surface attachment can be, for example, a polar group selected from the group consisting of —OR, —COR, —COOR, —NR$_2$, —PR$_2$, —SR and X, where each R independently can be H or a linear, branched, or cyclic C$_1$-C$_4$ aliphatic group, —COOR is not a carboxylic acid, and X is a halide.

The present invention is not limited to catalysts for CO$_2$ conversion or formic acid reactions. In particular, catalysts that include Catalytically Active Elements and Helper Catalysts might enhance the rate of a wide variety of chemical reactions. Reaction types include: homogeneously catalyzed reactions, heterogeneously catalyzed reactions, chemical reactions in chemical plants, chemical reactions in power plants, chemical reactions in pollution control equipment and devices, chemical reactions in fuel cells, and chemical reactions in sensors. The present invention includes all of these examples. The present invention also includes processes using these catalysts.

DETAILED DESCRIPTION OF PREFERRED EMBODIMENT(S)

Figure 1:
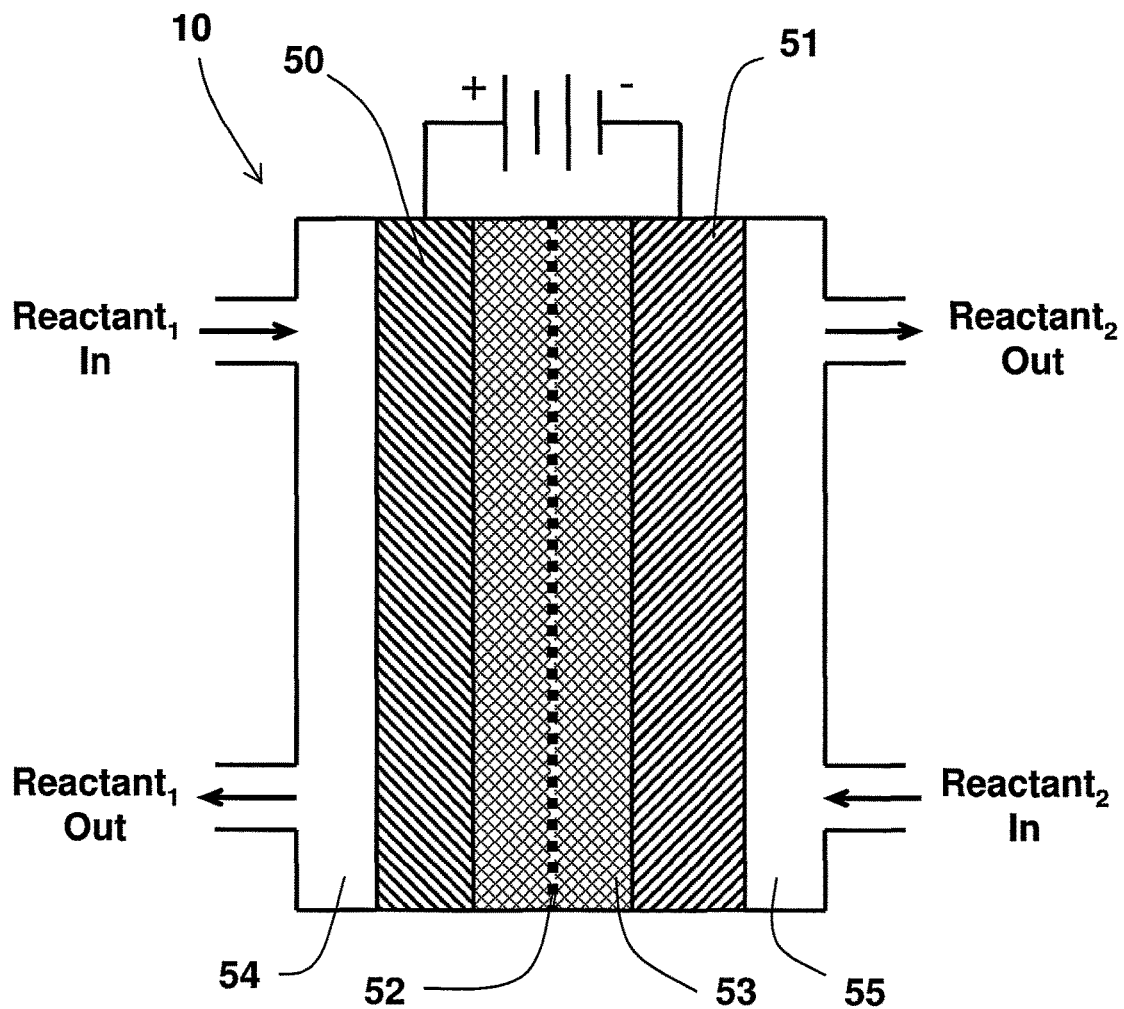
FIG. 1 is a diagram of a typical electrochemical cell.

It is understood that the invention is not limited to the particular methodology, protocols, and reagents, etc., described herein, as these can vary as the skilled artisan will recognize. It is also to be understood that the terminology used herein is used for the purpose of describing particular embodiments only, and is not intended to limit the scope of the invention. It also is to be noted that as used herein and in the appended claims, the singular forms "a", "an", and "the" include the plural reference unless the context clearly dictates otherwise. Thus, for example, a reference to "a linker" is a reference to one or more linkers and equivalents thereof known to those familiar with the technology involved here.

Unless defined otherwise, all technical and scientific terms used herein have the same meanings as commonly understood by one of ordinary skill in the art to which the invention pertains. The embodiments of the present invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment can be employed with other embodiments as the skilled artisan would recognize, even if not explicitly stated herein.

Any numerical value ranges recited herein include all values from the lower value to the upper value in increments of one unit provided that there is a separation of at least two units between a lower value and a higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the present invention are defined specifically. Particular methods, devices, and materials are described, although methods and materials similar or equivalent to those described herein can be used in the practice or testing of the present invention. All references referred to herein are incorporated by reference herein in their entirety.

Definitions

The term "electrochemical conversion of $CO_2$ as used here refers to an electrochemical process where carbon dioxide, carbonate, or bicarbonate is converted into another chemical substance in a step of the process.

The term "CV" as used here refers to a cyclic voltamogram or cyclic voltammetry.

The term "Overpotential" as used here refers to the potential (voltage) difference between a reaction's thermodynamically determined reduction or oxidation potential and the potential at which the event is experimentally observed.

The term "Cathode Overpotential" as used here refers to the overpotential on the cathode of an electrochemical cell.

The term "Anode Overpotential" as used here refers to the overpotential on the anode of an electrochemical cell.

The term "Electron Conversion Efficiency" refers to selectivity of an electrochemical reaction. More precisely, it is defined as the fraction of the current that is supplied to the cell that goes to the production of a desired product.

The term "Catalytically Active Element" as used here refers to a chemical element that can serve as a catalyst for the electrochemical conversion of $CO_2$ or another species of interest in a desired reaction.

The term "Helper Catalyst" refers to an organic molecule or mixture of organic molecules that does at least one of the following: (a) speeds up a chemical reaction, or (b) lowers the overpotential of the reaction, without being substantially consumed in the process.

The term "Active Element, Helper Catalyst Mixture" refers to a mixture that includes one or more Catalytically Active Element(s) and at least one Helper Catalyst The term "Ionic Liquid" refers to salts or ionic compounds that form stable liquids at temperatures below 200° C.

The term "Deep Eutectic Solvent" refers to an ionic solvent that includes a mixture which forms a eutectic with a melting point lower than that of the individual components.

The term "director molecule" (or "director ion") refers to a molecule or ion that increases the selectivity of a reaction. If a director molecule (or ion) is added to a reaction mixture, the selectivity for a desired reaction goes up. This effect may be the result of suppressing undesired side reactions, even if the desired reaction is also slowed, as long as the selectivity toward the desired reaction is increased.

The term "hydrogen suppressor" refers to a molecule that either: (a) decreases the rate of hydrogen formation, or (b) increases the overpotential for hydrogen formation, when the molecule is added to a reaction mixture.

Specific Description

The earlier related applications by Masel, et al., mentioned above, described Active Element, Helper Catalyst Mixtures where the mixture does at least one of the following: (1) speeds up a chemical reaction, or (2) lowers the overpotential of the reaction, without being substantially consumed in the process.

For example, such mixtures can lower the overpotential for $CO_2$ conversion to a value less than the overpotentials seen when the same Catalytically Active Element is used without the Helper Catalyst.

In the course of exploring these Active Element, Helper Catalyst Mixtures, it was found that certain materials that were being tested as Helper Catalysts, such as salts of the choline cation (N,N,N-trimethylethanolammonium cation) could also raise the overpotential for certain undesirable side reactions, such as the evolution of hydrogen gas from electrolysis of water, for example, in a fuel cell, battery, electrolytic cell or chemical sensor. Without wishing to be bound by theory, the present disclosure provides data supporting the hypothesis that when a monolayer of an organic compound is adsorbed on a metal surface, the presence of the organic compound can change the binding energy of key intermediates of reactions occurring on (or near) the metal surface. This can lead to changes in reaction rates. For example, data herein suggests that the adsorption of a cationic species such as a quaternary amine on an electrode (typically the negative electrode) of an electrochemical cell tends to stabilize anionic intermediates and destabilize cationic intermediates in electrochemical reactions. If the amine binds too strongly, it will simply poison the surface, but if the binding strength is modest, rate enhancement is possible. Aliphatic quaternary amines would tend to be merely electrostatically attracted to a metal electrode surface, since the positively charged nitrogen is sterically shielded by the aliphatic groups and cannot interact directly with the metal surface. For the same reason, quaternary ammonium cations tend to be electrochemically stable across a wide window of electrode potentials. Choline salts in particular are commercially attractive quaternary amines, because choline chloride is a common food additive for livestock, and it is also sold as a dietary supplement for humans. It is inexpensive, is readily available, and presents minimal hazard. One could reasonably expect that quaternary amine cations with structures similar to choline (for example, structures in which one or more of the methyl groups on the nitrogen is replaced with other small aliphatic groups such as ethyl or propyl groups) would behave in a fashion similar to the choline data disclosed in the present application.

According to the Hon review, Gattrell, et al. (Journal of Electroanalytical Chemistry, 594, 1-19, 2006), DuBois (Encyclopedia of Electrochemistry, 7a, 202-225, 2006) and references therein, catalysts including one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd all show activity for $CO_2$ conversion. Products include one or more of CO, $CO_3^{2-}$, $OH^-$, $HCO^-$, $H_2CO$, $(HCO_2)^-$, $H_2O_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$. Therefore, V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd are each examples of Catalytically Active Elements, but the present invention is not limited to this list of chemical elements. Possible products of the reaction include one or more of CO, $CO_3^{2-}$, $OH^-$, $HCO^-$, $H_2CO$, $(HCO_2)^-$, $H_2O_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$, but the present invention is not limited to this list of products.

The Hon review also notes that Pb, Hg, Tl, In, Cd, Bi, Zr, Cr, Sn and W are best for formic acid production. Furuya, et al. (Journal of Electroanalytical Chemistry, 431, 39-41, 1997) notes that Pd/Ru is also active.

The Hon review notes that there has been over 30 years of work on the electrochemical conversion of $CO_2$ into saleable products, but still, according to the Bell Report "Electron conversion efficiencies of greater than 50 percent can be obtained, but at the expense of very high overpotentials". This limitation needs to be overcome before practical processes can be obtained.

Figure 2:
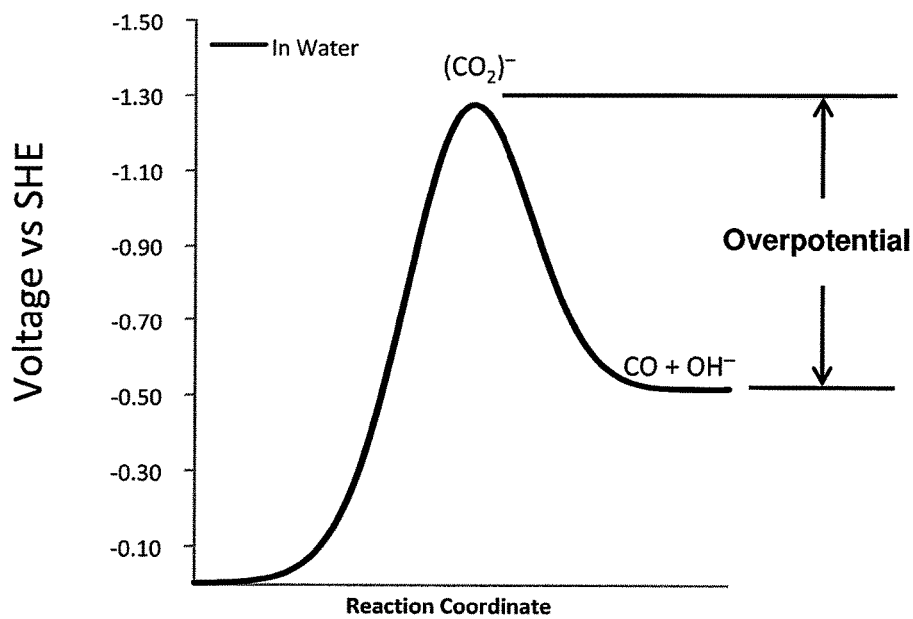
FIG. 2 is a schematic diagram of how the potential of the system moves as it proceeds along the reaction coordinate in the absence of the ionic liquid if the system goes through a (CO$_2$)$^-$ intermediate. The reaction coordinate indicates the fraction of the reaction that has been completed. A high potential for (CO$_2$)$^-$ formation can create a high overpotential for the reaction.
Figure 3:
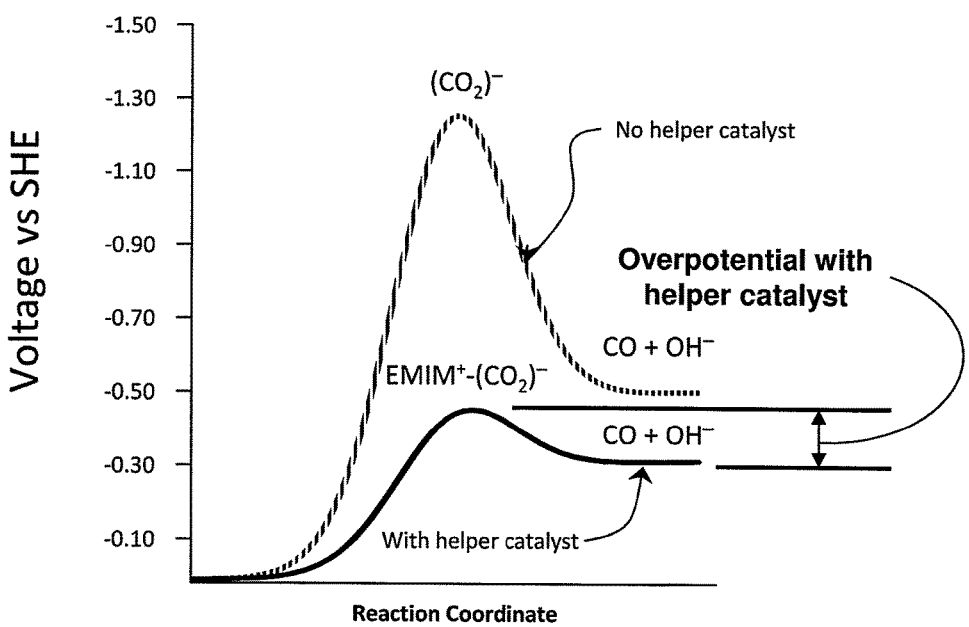
FIG. 3 illustrates how the potential could change when a Helper Catalyst is used. In this case the reaction could go through a CO$_2$ complex rather than a (CO$_2$)$^-$, substantially lowering the overpotential for the reaction.

FIGS. 2 and 3 illustrate one possible mechanism by which a Helper Catalyst can enhance the rate of $CO_2$ conversion. According to Chandrasekaran, et al. (Surface Science, 185, 495-514, 1987) the high overpotentials for $CO_2$ conversion occur because the first step in the electroreduction of $CO_2$ is the formation of a $(CO_2)^-$ intermediate. It takes energy to form the intermediate as illustrated in FIG. 2. This results in a high overpotential for the reaction.

FIG. 3 illustrates what might happen if a solution containing 1-ethyl-3-methylimidazolium cations ($EMIM^+$) is added to the mixture. $EMIM^+$ might be able to form a complex with the $(CO_2)^-$ intermediate. In that case, the reaction could proceed via the EMIM™ $(CO_2)^-$ complex instead of going through a bare $(CO_2)^-$ intermediate as illustrated in FIG. 3. If the energy to form the $EMIM^+$-$(CO_2)$ complex is less than the energy to form the $(CO_2)^-$ intermediate, the overpotential for $CO_2$ conversion could be substantially reduced. Therefore a substance that includes $EMIM^+$ cations could act as a Helper Catalyst for $CO_2$ conversion.

In most cases, solvents only have small effects on the progress of catalytic reactions. The interaction between a solvent and an adsorbate is usually much weaker than the interaction with a Catalytically Active Element, so the solvent only makes a small perturbation to the chemistry occurring on metal surfaces. However, the diagram in FIG. 3 shows that such an effect could be large.

Of course a Helper catalyst, alone, will be insufficient to convert $CO_2$. Instead, one still needs a Catalytically Active Element that can catalyze reactions of $(CO_2)^-$ in order to get high rates of $CO_2$ conversion. Catalysts including at least one of the following Catalytically Active Elements have been previously reported to be active for electrochemical conversion of $CO_2$: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd.

Many of these catalysts also show activity for a number of other reactions. All of these elements are specifically included as Catalytically Active Elements for the purposes of the present invention. This list of elements is meant for illustrative purposes only, and is not meant to limit the scope of the present invention.

Further, those skilled in the technology involved here should realize that the diagram in FIG. 3 could be drawn for any molecule that could form a complex with $(CO_2)^-$. Previous literature indicates that solutions including one or more of: ionic liquids, deep eutectic solvents, amines, and phosphines; including specifically imidazoliums (also called imidazoniums), pyridiniums, pyrrolidiniums, phosphoniums, ammoniums, sulfoniums, prolinates, and methioninates can form complexes with $CO_2$. Consequently, they can serve as Helper Catalysts. Also Davis Jr., et al. (in ACS Symposium Series 856: Ionic Liquids as Green Solvents: Progress and Prospects, 100-107, 2003) list a number of other salts that show ionic properties. Specific examples include compounds including one or more of acetylcholines, alanines, aminoacetonitriles, methylammoniums, arginines, aspartic acids, threonines, chloroformamidiniums, thiouroniums, quinoliniums, pyrrolidinols, serinols, benzamidines, sulfamates, acetates, carbamates, triflates, and cyanides. These salts can act as helper catalysts. These examples are meant for illustrative purposes only, and are not meant to limit the scope of the present invention.

Of course, not every substance that forms a complex with $(CO_2)^-$ will act as a Helper Catalyst. Masel (Chemical Kinetics and Catalysis, Wiley, pages 717-720, 2001,), notes that when an intermediate binds to a catalyst, the reactivity of the intermediate decreases. If the intermediate bonds too strongly to the catalyst, the intermediate will become unreactive, so the substance will not be effective. This provides a key limitation on substances that act as Helper Catalysts. The Helper Catalyst cannot form so strong a bond with the $(CO_2)^-$ that the $(CO_2)^-$ is unreactive toward the Catalytically Active Element.

More specifically, one wishes the substance to form a complex with the $(CO_2)^-$ so that the complex is stable (that is, has a negative free energy of formation) at potentials less negative than $-1$ V with respect to the standard hydrogen electrode (SHE). However, the complex should not be so stable that the free energy of the reaction between the complex and the Catalytically Active Element is more positive than about 3 kcal/mol.

Those familiar with the technology involved here should realize that the ability of the Helper Catalyst to stabilize the $(CO_2)^-$ also varies with the anion. For example Zhao, et al. (The Journal of Supercritical Fluids, 32, 287-291, 2004) examined $CO_2$ conversion in 1-n-butyl-3-methylimidazolium hexafluorophosphate (BMIM-PF6), but FIG. 3 in Zhao, et al., shows that the BMIM-PF6 did NOT lower the overpotential for the reaction (that is, the BMIM-PF6 did not act as a Helper Catalyst). This may be because the BMIM-PF6 formed such a strong bond to the $(CO_2)^-$ that the $CO_2$ was unreactive with the copper. Similarly Yuan, et al., Electrochimica Acta 54, pages 2912-2915 (2009), examined the reaction between methanol and $CO_2$ in 1-butyl-3-methylimidazolium bromide (BMIM-Br). The BMIM-Br did not act as a Helper Catalyst. This may be because the complex was too weak or that the bromine poisoned the reaction.

Figure 4A:
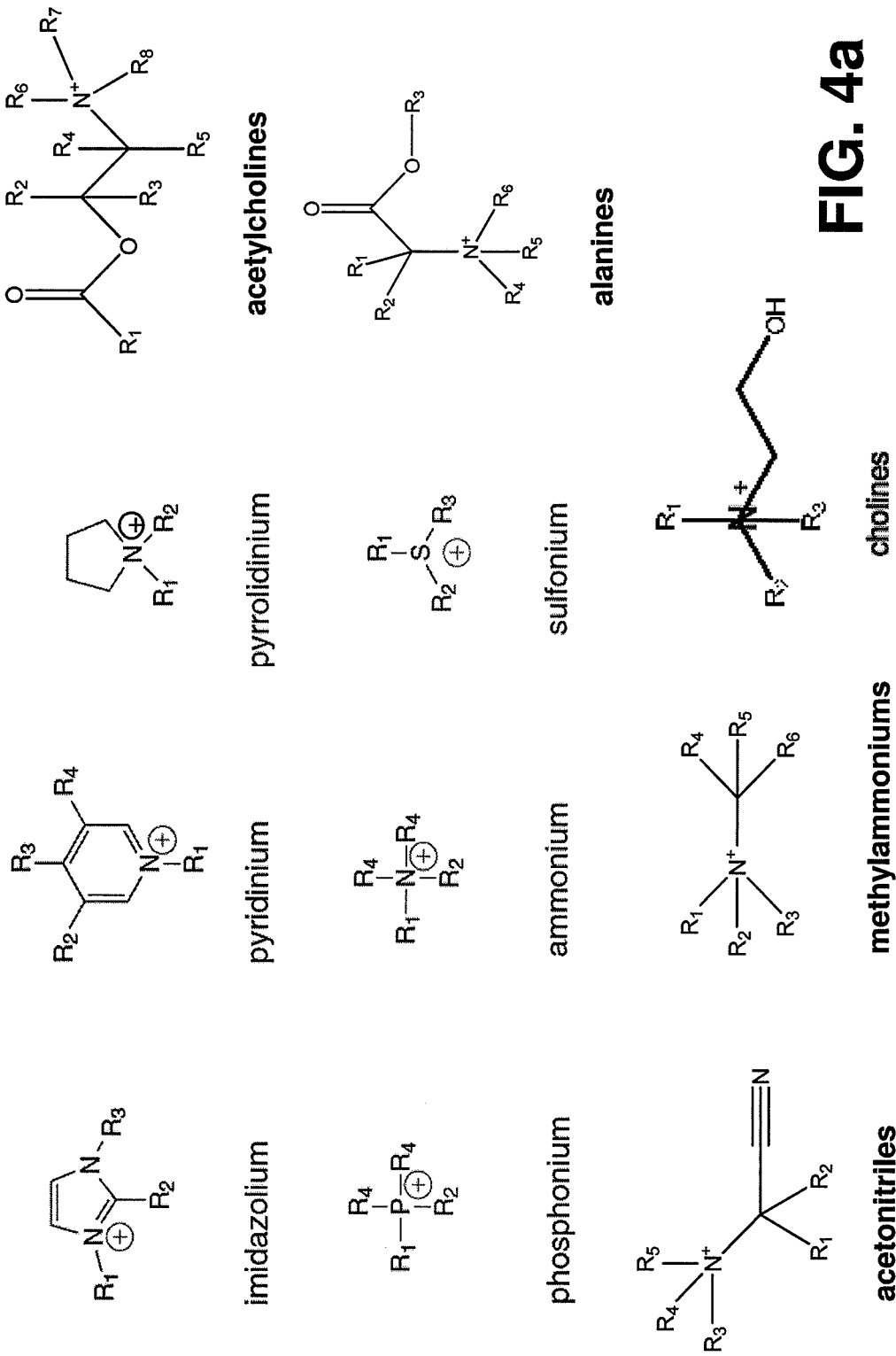
FIGS. 4a, 4b and 4c illustrate some of the cations that can be used to form a complex with (CO$_2$)$^-$.
Figure 4B:
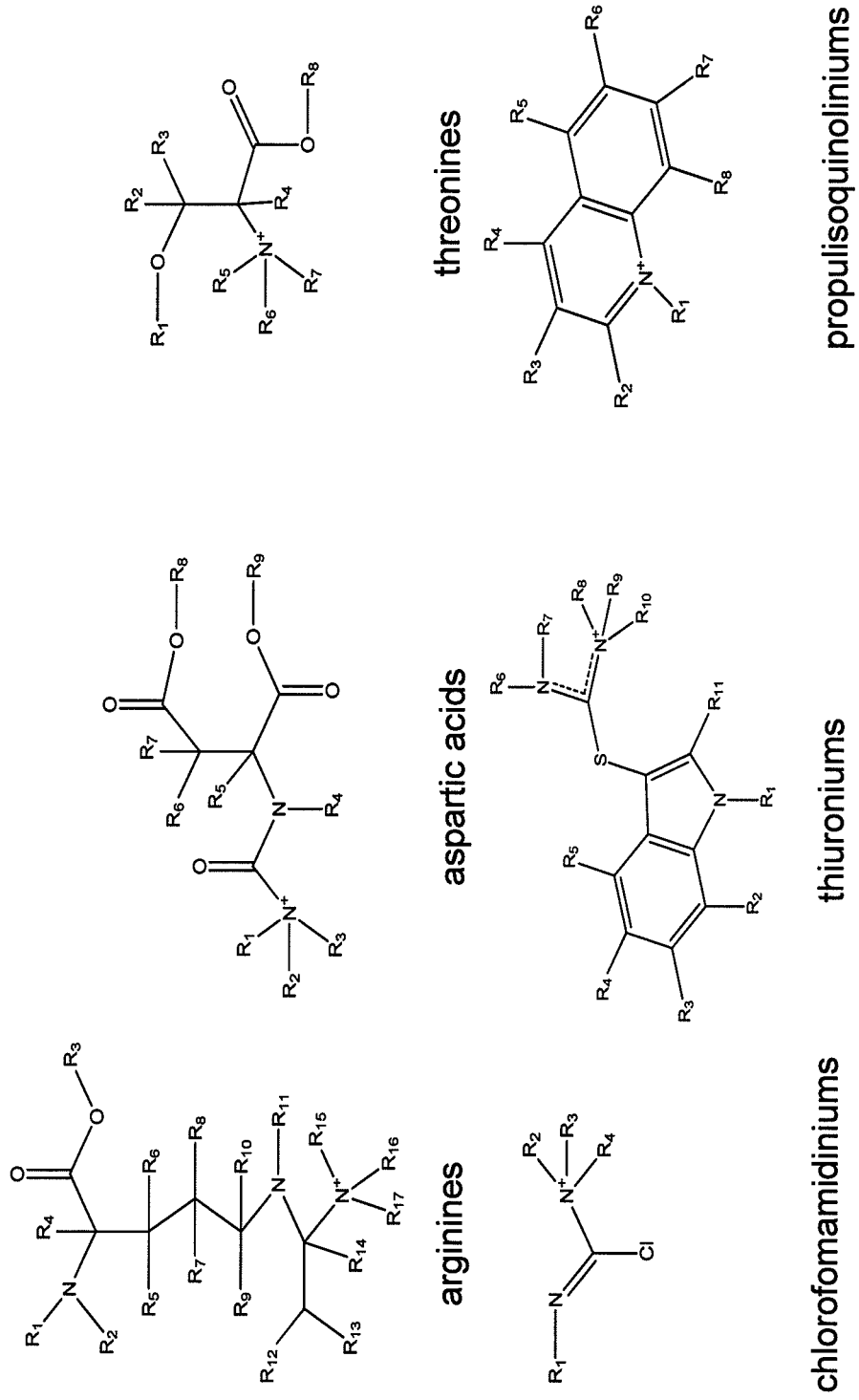
Figure 4C:
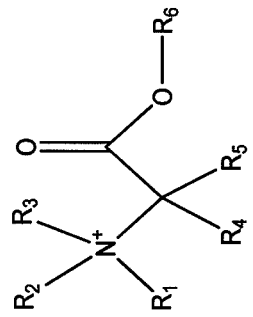
Figure 4C:
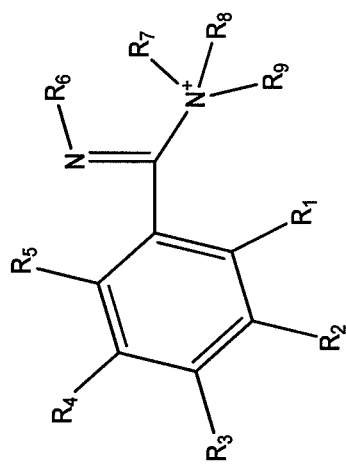
Figure 4C:
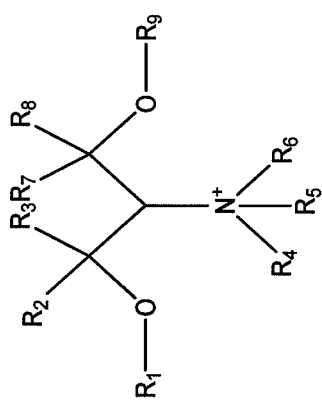
Figure 5A:
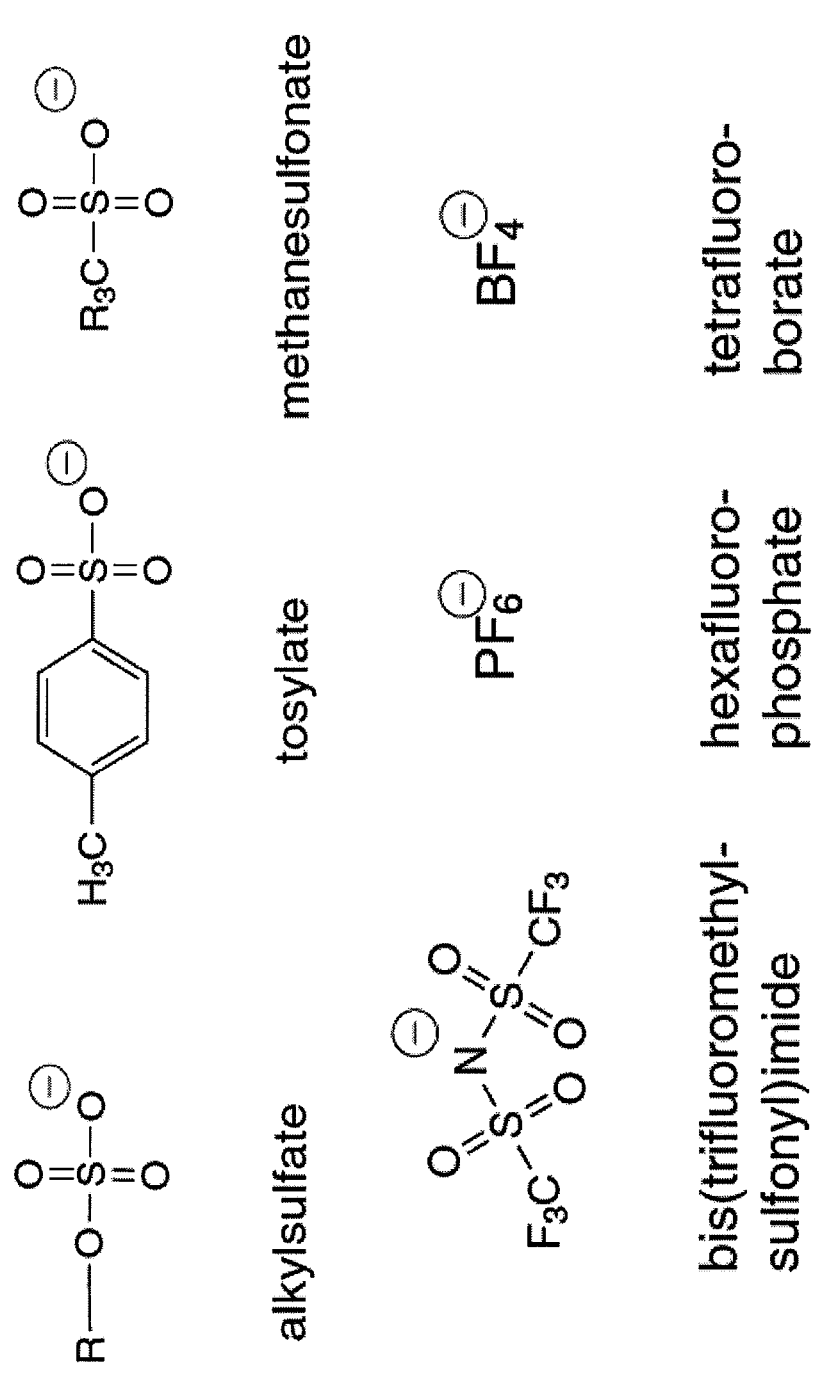
FIGS. 5a and 5b illustrate some of the anions that can help to stabilize the (CO$_2$)$^-$ anion.
Figure 5B:
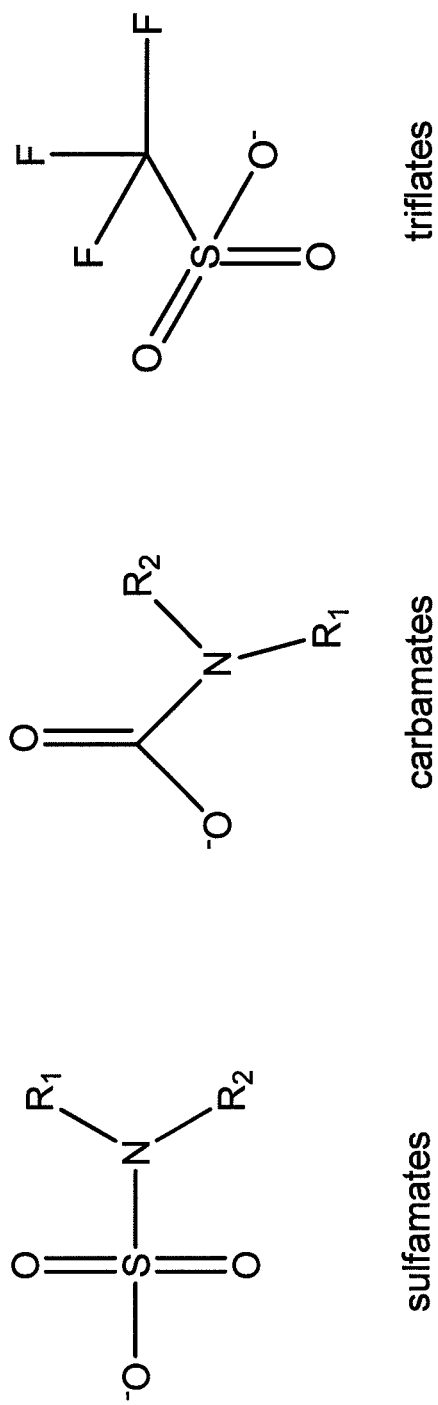
Figure 6:
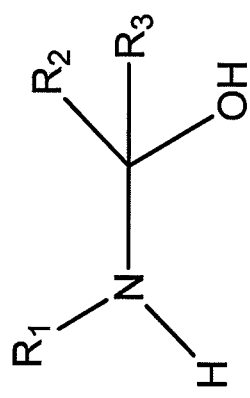
FIG. 6 illustrates some of the neutral molecules that can be used to form a complex with (CO$_2$)$^-$.
Figure 6:
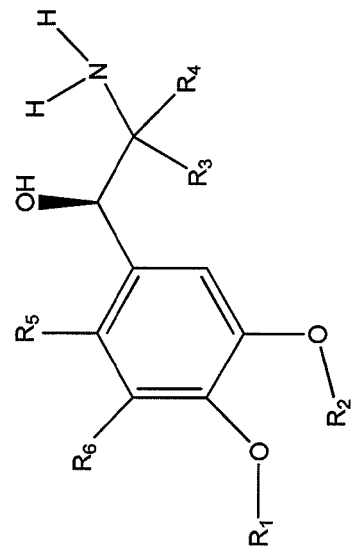
Figure 6:
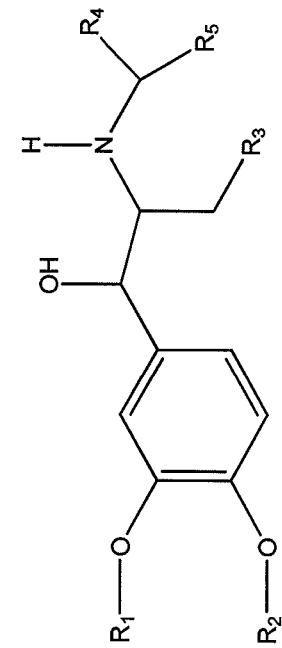

Solutions that include one or more of the cations in FIGS. 4a, 4b and 4c, the anions in FIGS. 5a and 5b, and/or the neutral species in FIG. 6, where $R_1$, $R_2$ and $R_3$ (and $R_4$-$R_{17}$) include H, OH or a ligand containing at least one carbon atom, are believed to form complexes with $CO_2$ or $(CO_2)^-$. Specific examples include: imidazoliums (also called imidazoniums), pyridiniums, pyrrolidiniums, phosphoniums, ammoniums, sulfoniums, prolinates, and methioninates. All of these examples might be able to be used as Helper Catalysts for $CO_2$ conversion, and are specifically included in the present invention. These examples are meant for illustrative purposes only, and are not meant to limit the scope of the present invention.

In general one can determine whether a given substance S is a helper catalyst for a reaction R catalyzed by an active metal M as follows:
  (a) Fill a standard 3-electrode electrochemical cell with the electrolyte commonly used for reaction R. Common electrolytes include such as 0.1 M sulfuric acid or 0.1 M KOH in water can also be used.
  (b) Mount the active metal into the 3 electrode electrochemical cell and an appropriate counter electrode.
  (c) Run several CV cycles to clean the active metal.
  (d) Measure the reversible hydrogen electrode (RHE) potential in the electrolyte.
  (e) Load the reactants for the reaction R into the cell, and measure a CV of the reaction R, noting the potential of the peak associated with the reaction R.
  (f) Calculate V1=the difference between the onset potential of the peak associated with reaction and RHE.
  (g) Calculate V1A=the difference between the maximum potential of the peak associated with reaction and RHE.
  (h) Add 0.0001 to 99.9999% of the substance S to the electrolyte.
  (i) Measure RHE in the reaction with Helper Catalyst.
  (j) Measure the CV of reaction R again, noting the potential of the peak associated with the reaction R.
  (k) Calculate V2=the difference between the onset potential of the peak associated with reaction and RHE.
  (l) Calculate V2A=the difference between the maximum potential of the peak associated with reaction and RHE.

If V2<V1 or V2A<V1A at any concentration of the substance S between 0.0001 and 99.9999%, the substance S is a Helper Catalyst for the reaction.

Further, the Helper Catalyst could be in any one of the following forms: (i) a solvent for the reaction; (ii) an electrolyte; (iii) an additive to a component of the system; or (iv) something that is bound to at least one of the catalysts in a system. These examples are meant for illustrative purposes only, and are not meant to limit the scope of the present invention.

Those familiar with the technology involved here should recognize that one might only need a tiny amount of the Helper Catalyst to have a significant effect. Catalytic reactions often occur on distinct active sites. The active site concentration can be very low, so in principle a small amount of Helper Catalyst can have a significant effect on the rate. One can obtain an estimate of how little of the helper catalyst would be needed to change the reaction from Pease, et al., JACS 47, 1235 (1925) study of the effect of carbon monoxide (CO) on the rate of ethylene hydrogenation on copper. This paper is incorporated into this disclosure by reference. Pease, et al., found that 0.05 cc (62 micrograms) of carbon monoxide (CO) was sufficient to almost completely poison a 100 gram catalyst towards ethylene hydrogenation. This corresponds to a poison concentration of 0.0000062% by weight of CO in the catalyst. Those familiar with the technology involved here know that if 0.0000062% by weight of the poison in a Catalytically Active Element-poison mixture could effectively suppress a reaction, then as little as 0.0000062% by weight of Helper Catalyst in an Active Element, Helper Catalyst Mixture could enhance a reaction. This provides an estimate of a lower limit to the Helper Catalyst concentration in an Active Element, Helper Catalyst Mixture.

The upper limit is illustrated in Example 1 below, where the Active Element, Helper Catalyst Mixture could have approximately 99.999% by weight of Helper Catalyst, and the Helper Catalyst could be at least an order of magnitude more concentrated. Thus, the range of Helper Catalyst concentrations for the present invention can be 0.0000062% to 99.9999% by weight.

FIG. 3 only considered the electrochemical conversion of $CO_2$, but the method is general. There are many examples where energy is needed to create a key intermediate in a reaction sequence. Examples include: homogeneously catalyzed reactions, heterogeneously catalyzed reactions, chemical reactions in chemical plants, chemical reactions in power plants, chemical reactions in pollution control equipment and devices, chemical reactions in safety equipment, chemical reactions in fuel cells, and chemical reactions in sensors.

Theoretically, if one could find a Helper Catalyst that forms a complex with a key intermediate, the rate of the reaction should increase. All of these examples are within the scope of the present invention.

Specific examples of specific processes that can benefit with Helper Catalysts include the electrochemical process to produce products including one or more of $Cl_2$, $Br_2$, $I_2$, NaOH, KOH, NaClO, $NaClO_3$, $KClO_3$, $CF_3COOH$.

Further, the Helper Catalyst could enhance the rate of a reaction even if it does not form a complex with a key intermediate. Examples of possible mechanisms of action include the Helper Catalyst (i) lowering the energy to form a key intermediate by any means, (ii) donating or accepting electrons or atoms or ligands, (iii) weakening bonds or otherwise making them easier to break, (iv) stabilizing excited states, (v) stabilizing transition states, (vi) holding the reactants in close proximity or in the right configuration to react, or (vii) blocking side reactions. Each of these mechanisms is described on pages 707-742 of Masel, Chemical Kinetics and Catalysis, Wiley, NY (2001). All of these modes of action are within the scope of the present invention.

Also, the invention is not limited to just the catalyst. Instead it includes a process or device that uses an Active Element, Helper Catalyst Mixture as a catalyst. Fuel cells, sensors and electrolytic cells are specifically included in the present invention.

Without further elaboration, it is believed that one skilled in the art using the preceding description can utilize the present invention to the fullest extent. The following examples are illustrative only, and not limiting of the disclosure in any way whatsoever. These are merely illustrative and are not meant to be an exhaustive list of all possible embodiments, applications or modifications of the present invention.

Testing of Active Element, Helper Catalyst Mixtures

The following section describes the testing procedure used for an Active Element, Helper Catalyst Mixture as previously disclosed in the related applications cited above. These particular experiments measured the ability of an Active Element, Helper Catalyst Mixture consisting of platinum and 1-ethyl-3-methylimidazolium tetrafluoroborate (EMIM-BF4) to lower the overpotential for electrochemical conversion of $CO_2$ and raise the selectivity (current efficiency) of the reaction. Therefore, the test can determine whether EMIM-BF4 and the $EMIM^+$ ion can serve as director molecules and director ions, respectively, for the desired reaction. The desired reaction in this test will be the electrochemical reduction of carbon dioxide (typically to primary products such as CO or formic acid).

Figure 7:
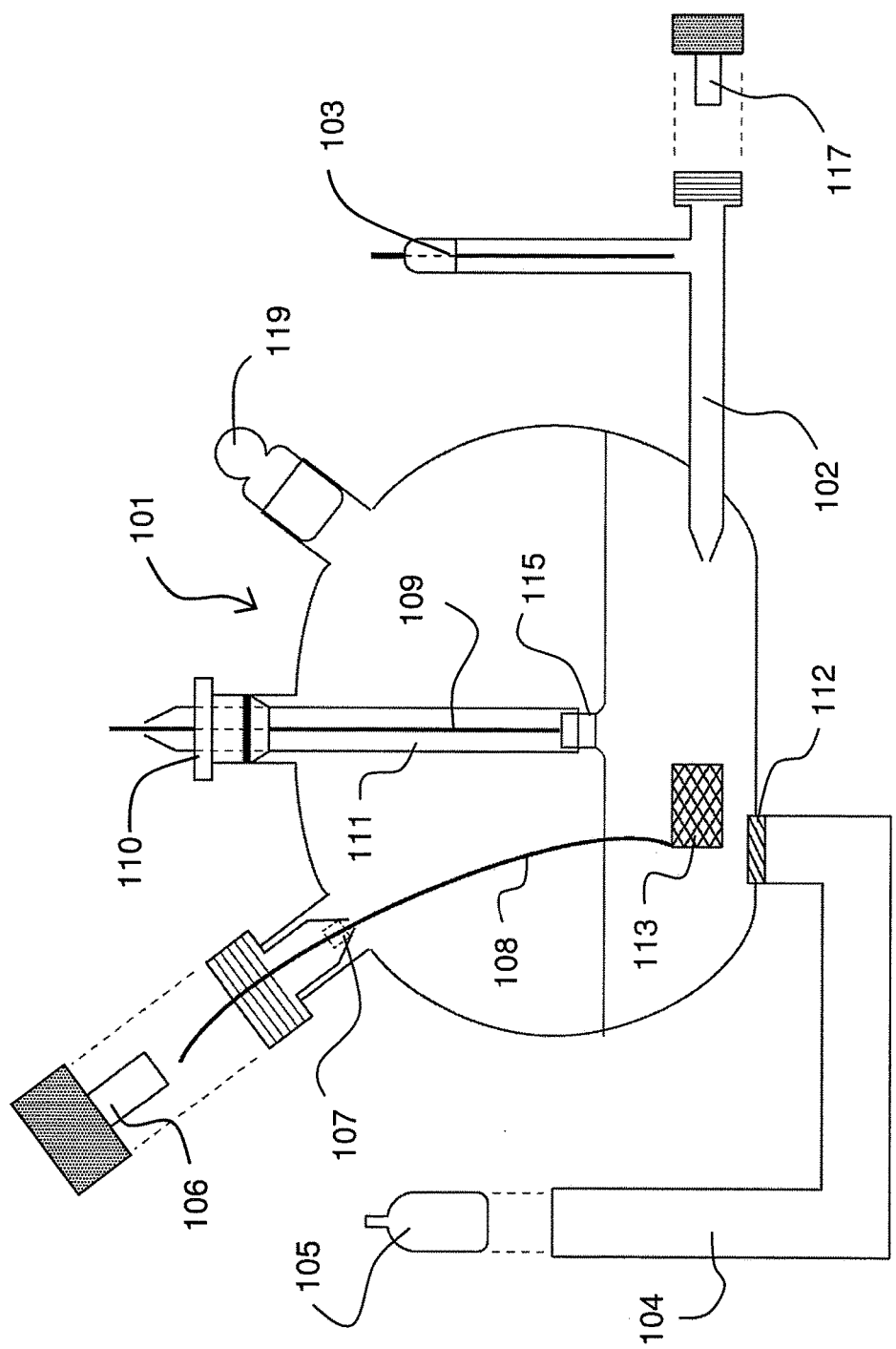
FIG. 7 shows a schematic diagram of a cell used for the experiments in testing Catalytically Active Element, Helper Catalyst Mixtures, and in Specific Examples 1, 2, and 3.

The experiments used the glass three electrode cell shown in FIG. 7. The cell consisted of a three neck flask 101, to hold the anode 108, and the cathode 109. Seal 107 forms a seal around anode wire 108. Fitting 106 compresses seal 107 around anode wire 108. Rotary seal 110 facilitates rotation of shaft 111, which in turn causes gold plug 115 to spin. Seal 119 closes the unused third neck of flask 101.

A silver/0.01 molar silver ion reference electrode 103 in acetonitrile was connected to the cell through a Luggin Capillary 102, which includes a seal 117. The reference electrode 103 was fitted with a Vycor® frit to prevent the reference electrode solution from contaminating the ionic liquid in the capillary. The reference electrode was calibrated against the ferrocene Fc/Fc+ redox couple. A conversion factor of +535 was used to convert our potential axis to reference the Standard Hydrogen Electrode (SHE). A 25×25 mm platinum gauze 113 (size 52) was connected to the anode while a 0.33 $cm^2$ polycrystalline gold plug 115 was connected to the cathode.

Prior to the experiments all glass parts were put through a 1% Nochromix® bath (2 hrs), followed by a 50/50 v/v nitric acid/water bath (12 hrs), followed by rinsing with Millipore water. In addition, the gold plug 115 and platinum gauze 113 were mechanically polished using procedures known to workers trained in the technology involved here. The glass parts were then cleaned in a sulfuric acid bath for 12 hours.

During the experiment a catalyst ink comprising a Catalytically Active Element, platinum, was first prepared as follows: First 0.056 grams of Johnson-Matthey Hispec 1000 platinum black purchased from Alfa-Aesar was mixed with 1 gram of Millipore water and sonicated for 10 minutes to produce a solution containing a 5.6 mg/ml suspension of platinum black in Millipore water. A 25 µl drop of the ink was placed on the gold plug 115 and allowed to dry under a heat lamp for 20 min, and subsequently allowed to dry in air for an additional hour. This yielded a catalyst with 0.00014 grams of Catalytically Active Element, platinum, on a gold plug. The gold plug was mounted into the three neck flask 101. Next a Helper Catalyst, EMIM-BF4 (EMD Chemicals, Inc., San Diego, Calif., USA) was heated to 120° C. under a −23 in. Hg vacuum for 12 hours to remove residual water and oxygen. The concentration of water in the ionic liquid after this procedure was found to be approximately 90 mM by conducting a Karl-Fischer titration. (That is, the ionic liquid contained 99.9999% of Helper Catalyst.) 13 grams of the EMIM-BF4 was added to the vessel, creating an Active Element, Helper Catalyst Mixture that contained about 99.999% of the Helper Catalyst. The geometry was such that the gold plug formed a meniscus with the EMIM-BF4. Next, ultra-high-purity (UHP) argon was fed through the sparging tube 104 and glass frit 112 for 2 hours at 200 sccm to further remove any moisture picked up by contact with the air. Connector 105 is used to attach the cell to a tube leading to the gas source.

Next, the cathode was connected to the working electrode connection in an SI 1287 Solartron electrical interface, the anode was connected to the counter electrode connection and the reference electrode was connected to the reference electrode connection on the Solartron. Then the potential on the cathode was swept from −1.5 V versus a standard hydrogen electrode (SHE) to 1V vs. SHE, and then back to −1.5 volts versus SHE thirty times at a scan rate of 50 mV/s. The current produced during the last scan is labeled as the "argon" scan in FIG. 8.

Next carbon dioxide was bubbled through the sparging tube at 200 sccm for 30 minutes, and the same scanning technique was used. That produced the $CO_2$ scan in FIG. 8. Notice the peak starting at −0.2 volts with respect to SHE, and reaching a maximum at −0.4 V with respect to SHE. That peak is associated with $CO_2$ conversion.

The applicants have also used broad-band sum frequency generation (BB-SFG) spectroscopy to look for products of the reaction. The desired product carbon monoxide was only detected in the voltage range shown (namely, the selectivity is about 100%) Oxalic acid was detected at higher potentials.

Table 1 compares these results to results from the previous literature. The table shows the actual cathode potential. More negative cathode potentials correspond to higher overpotentials. More precisely the overpotential is the difference between the thermodynamic potential for the reaction (about −0.2 V with respect to SHE) and the actual cathode potential. The values of the cathode overpotential are also given in the table. Notice that the addition of the Helper Catalyst has reduced the cathode overpotential (namely, lost work) on platinum by a factor of 4.5 and improved the selectivity to nearly 100%.

TABLE 1

(Comparison of data in this test to results reported in previous literature)

| Reference | Catalytically Active Element | Cathode potential versus SHE | Cathode overpotential | Selectivity to carbon-containing products |
|---|---|---|---|---|
| Data from this test | Platinum (+EMIM-BF$_4$) | −0.4 V | 0.2 V | ~100% |
| Hori review Table 3 | Platinum (+water) | −1.07 V | 0.87 V | 0.1% |
| The Li and Oloman papers and the '727 publication | Tin | −2.5 to −3.2 V | 2.3 to 3 V | 40-70% |

TABLE 2

(Cathode potentials where CO$_2$ conversion starts on a number of Catalytically Active Elements as reported in the Hori review).

| Metal | Cathode potential (SHE) | Metal | Cathode potential (SHE) | Metal | Cathode potential (SHE) |
|---|---|---|---|---|---|
| Pb | −1.63 | Hg | −1.51 | Tl | −1.60 |
| In | −1.55 | Sn | −1.48 | Cd | −1.63 |
| Bi | −1.56 | Au | −1.14 | Ag | −1.37 |
| Zn | −1.54 | Pd | −1.20 | Ga | −1.24 |
| Cu | −1.44 | Ni | −1.48 | Fe | −0.91 |
| Pt | −1.07 | Ti | −1.60 | | |

Figure 8:
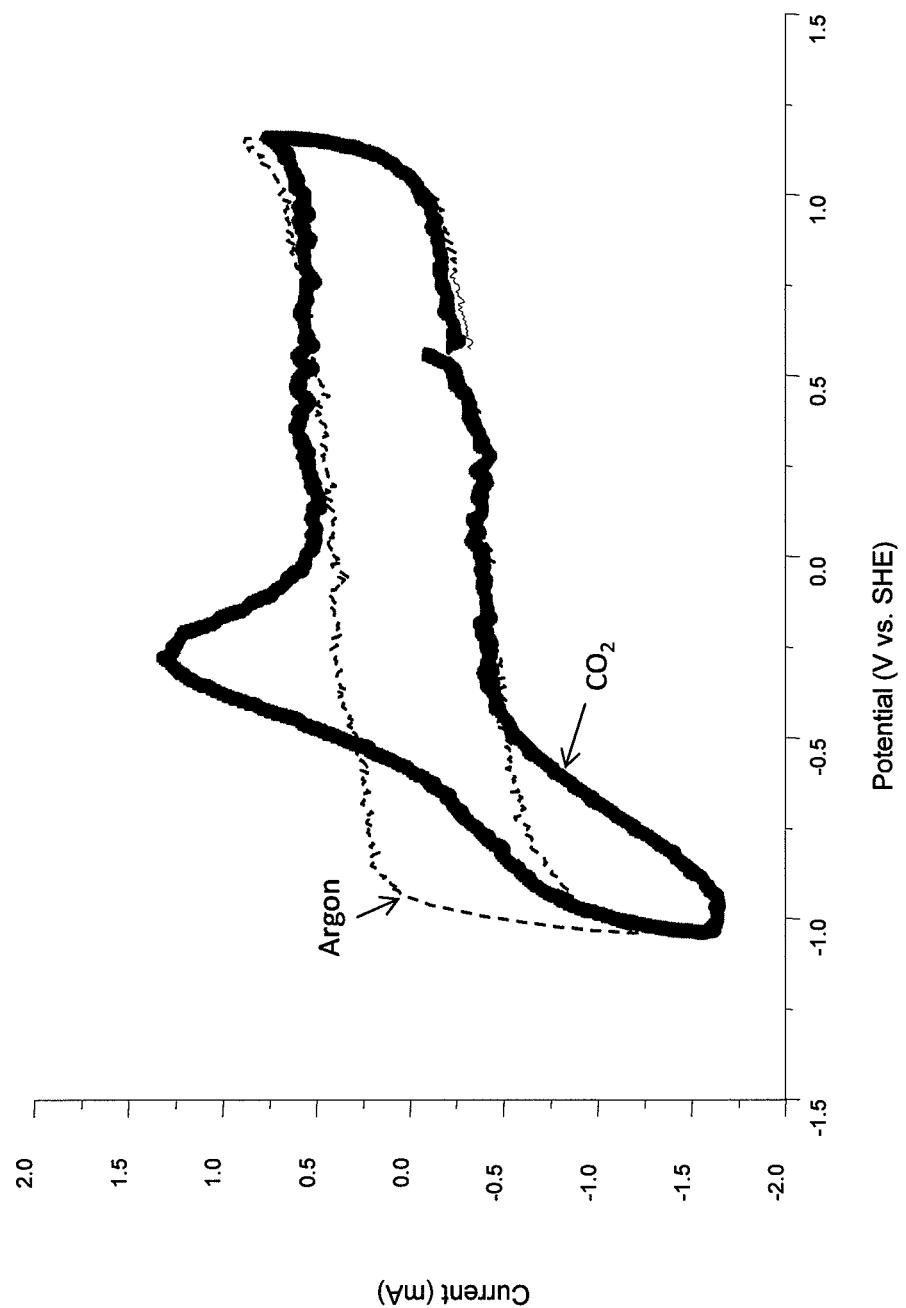
FIG. 8 represents a comparison of the cyclic voltammetry for a blank scan where the catalyst was synthesized as in the described testing procedure for Catalytically Active Element, Helper Catalyst Mixtures, where (i) the EMIM-BF4 was sparged with argon, and (ii) a scan where the EMIM-BF4 was sparged with CO$_2$. Notice the large negative peak associated with CO$_2$ complex formation.

Table 2 indicates the cathode potential needed to convert CO$_2$. Notice that all of the values are more negative than −0.9 V. By comparison, FIG. 8 shows that CO$_2$ conversion starts at −0.2 V with respect to the reversible hydrogen electrode (RHE), when the Active Element, Helper Catalyst Mixture is used as a catalyst. More negative cathode potentials correspond to higher overpotentials. This is further confirmation that Active Element, Helper Catalyst Mixtures are advantageous for CO$_2$ conversion.

Figure 9:
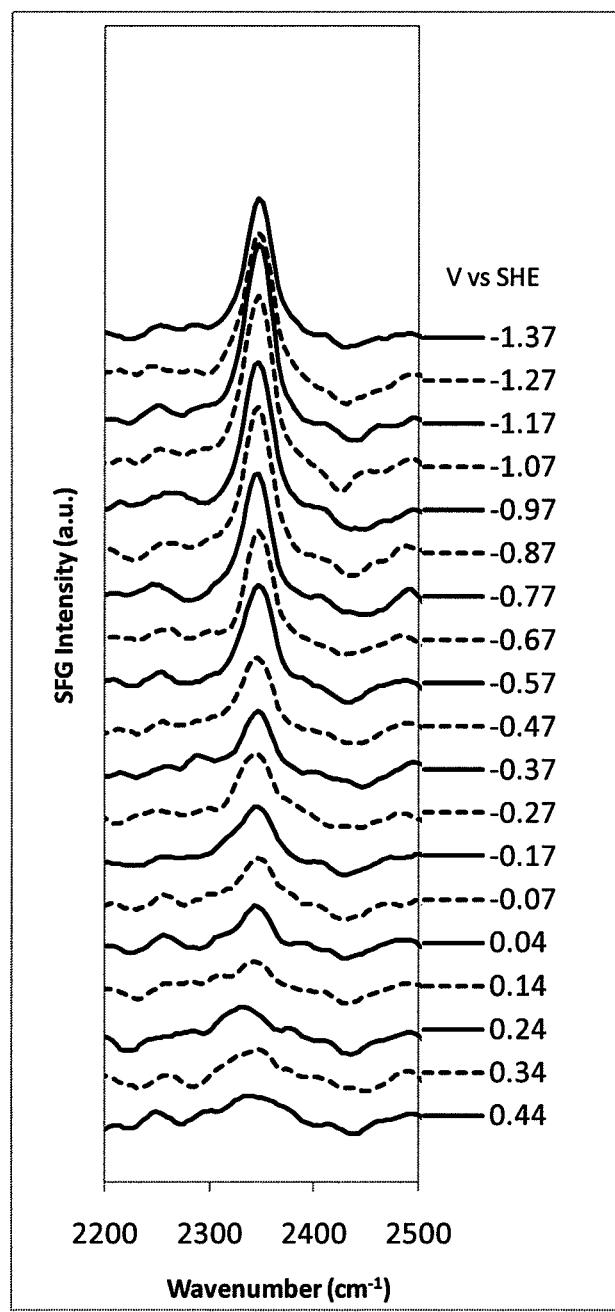
FIG. 9 represents a series of Broad Band Sum Frequency Generation (BB-SFG) spectra taken sequentially as the potential in the cell was scanned from +0.0 V to −1.2 V with respect to the standard hydrogen electrode (SHE).

FIG. 9 shows a series of broad band sum-frequency generation (BB-SFG) spectra taken during the reaction. Notice the peak at 2350 cm$^{-1}$. This peak corresponded to the formation of a stable complex between the Helper Catalyst and $(CO_2)^-$. It is significant that the peak starts at −0.1 V with respect to SHE. According to the Hori review, $(CO_2)^-$ is thermodynamically unstable unless the potential is more negative than −1.2 V with respect to SHE on platinum. Yet FIG. 9 shows that the complex between EMIM-BF4 and $(CO_2)^-$ is stable at −0.1 V with respect to SHE.

Those familiar with the technology involved here should recognize that this result is very significant. According to the Hori review, the Dubois review and references therein, the formation of $(CO_2)^-$ is the rate determining step in CO$_2$ conversion to CO, OH—, HCO—, H$_2$CO, (HCO$_2$)—, H$_2$CO$_2$, CH$_3$OH, CH$_4$, C$_2$H$_4$, CH$_3$CH$_2$OH, CH$_3$COO$^-$, CH$_3$COOH, C$_2$H$_6$, O$_2$, H$_2$, (COOH)$_2$, and (COO$^-$)$_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd. The $(CO_2)^-$ is thermodynamically unstable at low potentials, which leads to a high overpotential for the reaction as indicated in FIG. 2. The data in FIG. 9 shows that one can form the EMIM-BF4-$(CO_2)^-$ complex at low potentials. Thus, the reaction can follow a low energy pathway for CO$_2$ conversion to CO, OH$^-$, HCO$^-$, H$_2$CO, (HCO$_2$)$^-$, H$_2$CO$_2$, CH$_3$OH, CH$_4$, C$_2$H$_4$, CH$_3$CH$_2$OH, CH$_3$COO$^-$, CH$_3$COOH, C$_2$H$_6$, O$_2$, H$_2$, (COOH)$_2$, or (COO$^-$)$_2$ on V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Sn, Tl, Pb, Bi, Sb, Te, U, Sm, Tb, La, Ce, and Nd as indicated in FIG. 3.

In order to understand the economic consequences of this result, we calculated the cost of the electricity needed to create 100,000 metric tons per year of formic acid via two processes, (i) the process described in The Li and Oloman papers and the '727 publication, and (ii) a similar process using the catalyst in this example. In both cases we assumed that the anode would run at +1.2 V with respect to SHE and that electricity would cost $0.06/kW-hr, and we scaled the current to be reasonable. The results of the calculations are given in Table 3. Notice that the calculations predict that the electricity cost will go down by almost a factor of 5 if the new catalysts are used. These results demonstrate the possible impact of the new catalysts disclosed here.

TABLE 3

(Comparison of the projected costs using catalyst in Li and Oloman papers and the '727 publication, and a similar process using the catalyst in this example).

| Catalyst | Cathode potential, V (SHE) | Anode potential, V (SHE) | Net potential, V | Selectivity | Yearly electricity cost |
|---|---|---|---|---|---|
| The Li and Oloman papers and the '727 publication | −3.2 | 1.2 | 4.4 | 0.6 | $65,000,000 |
| Active Element, Helper Catalyst Mixture | −0.4 | 1.2 | 1.6 | 1 | $14,000,000 |

The Effect of Dilution on the Electrochemical Conversion of CO$_2$

Figure 10:
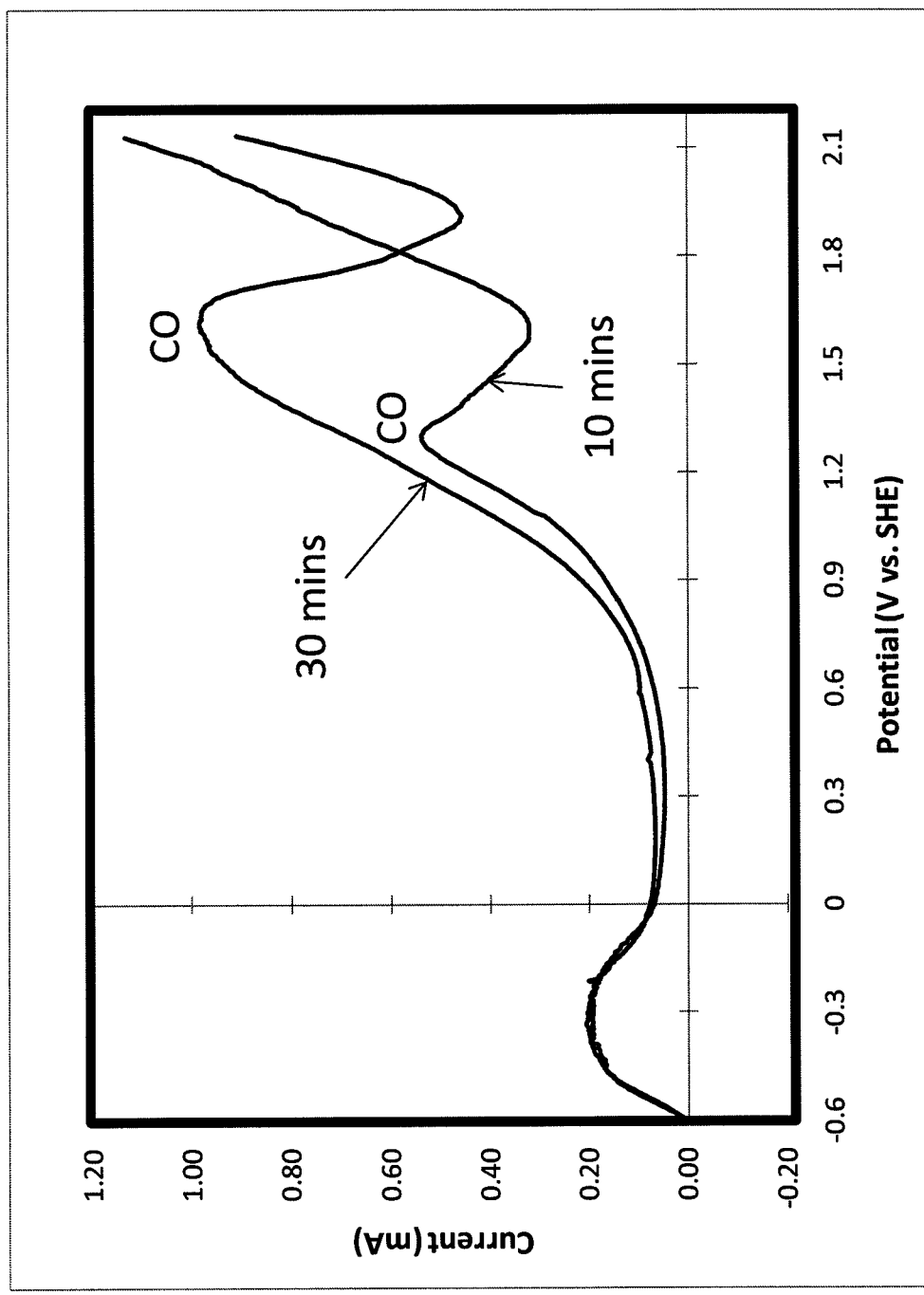
FIG. 10 shows a CO stripping experiment done by holding the potential at −0.6 V for 10 or 30 minutes and then measuring the size of the CO stripping peak between 1.2 and 1.5 V with respect to the reversible hydrogen electrode (RHE).

This experiment shows that water additions speed the formation of CO in the previous reaction. The experiment used the cell and procedures described above, with the following exception: a solution containing 98.55% EMIM-BF4 and 0.45% water was substituted for the 99.9999% EMIM-BF4 used in the experiment above, the potential was held for 10 or 30 minutes at −0.6 V with respect to RHE, and then the potential was ramped positively at 50 mV/sec. FIG. 10 shows the result. Notice the peak between 1.2 and 1.5 V. This is the peak associated with CO formation and is much larger than in the first experiment above. Thus the addition of water has accelerated the formation of CO presumably by acting as a reactant.

Specific Example 1

Use of an Active Element, Helper Catalyst Mixture Including Palladium and Choline Iodide to Lower the Overpotential for Electrochemical Conversion of CO$_2$ in Water and Suppress Hydrogen Formation This example is to demonstrate that the present invention can be practiced using palladium as an active element and choline iodide as a Helper Catalyst.

The experiment used the cell and procedures described in the first test above, with the following exceptions: i) a 10.3% by weight of a Helper Catalyst, choline iodide, in water solution was substituted for the 1-ethyl-3-methylimidazolium tetrafluoroborate and ii) a 0.25 cm² Pd foil purchased from Alfa Aesar of Ward Hill, Mass., USA, was substituted for the gold plug and platinum black on the cathode, and a silver/silver chloride reference was used.

The cell contained 52 mg of palladium and 103 mg of helper catalyst, so the overall catalyst mixture contained 66% of helper catalyst.

Figure 11:
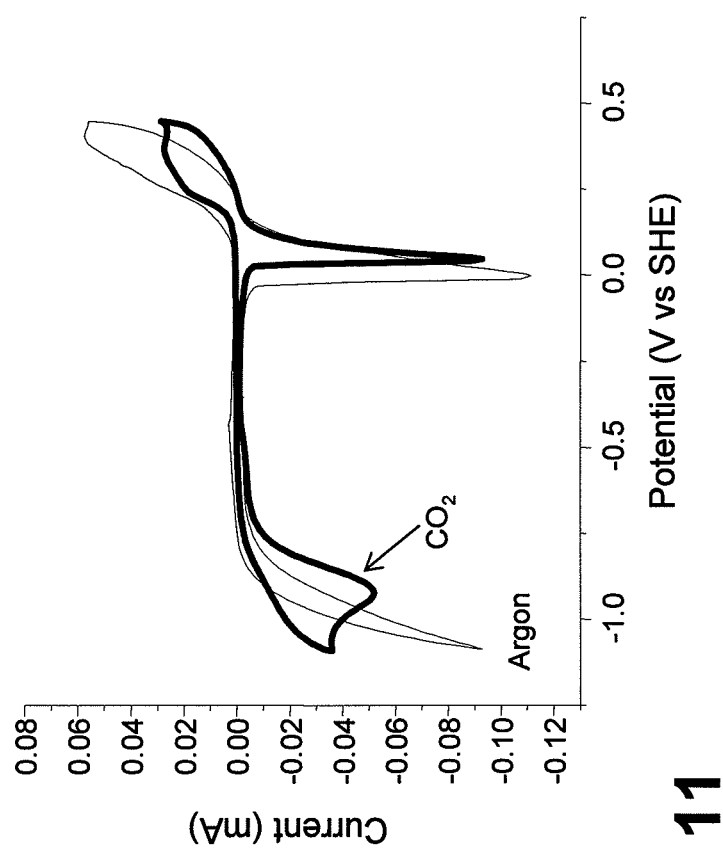
FIG. 11 represents a comparison of the cyclic voltammetry for a blank scan where the catalyst was synthesized as in Example 1 where (i) the water-choline iodide mixture was sparged with argon and (ii) a scan where the water-choline iodide mixture was sparged with CO$_2$.

FIG. 11 shows a CV taken under these conditions. There is a large negative peak near zero volts with respect to SHE associated with iodine transformations and a negative going peak at about −0.8 V associated with conversion of $CO_2$. By comparison the data in Table 2 indicates that one needs to use a voltage more negative than −1.2 V to convert $CO_2$ on palladium in the absence of the Helper Catalyst. Thus, the Helper Catalyst has lowered the overpotential for $CO_2$ formation by about 0.5 V.

This example also demonstrates that the Active Element, Helper Catalyst Mixture concept can be practiced with a second Active Element, palladium, and a second Helper Catalyst, choline iodide. Further, those trained in the technology involved here will note that the choice of the combination palladium and choline iodide is not critical. Rather, this example shows that the results are general and not limited to the special case of EMIM-BF4 on platinum described in the test experiments above.

Specific Example 2

Use of an Active Element, Helper Catalyst Mixture that Includes Palladium and Choline Chloride to Lower the Overpotential for Electrochemical Conversion of $CO_2$ to Formic Acid and Suppress Hydrogen Formation The next example is to demonstrate that the present invention can be practiced using a second Helper Catalyst, choline chloride.

The experiment used the cell and procedures in Example 1, with the following exception: a 6.5% by weight choline chloride in water solution was substituted for the choline iodide solution.

Figure 12:
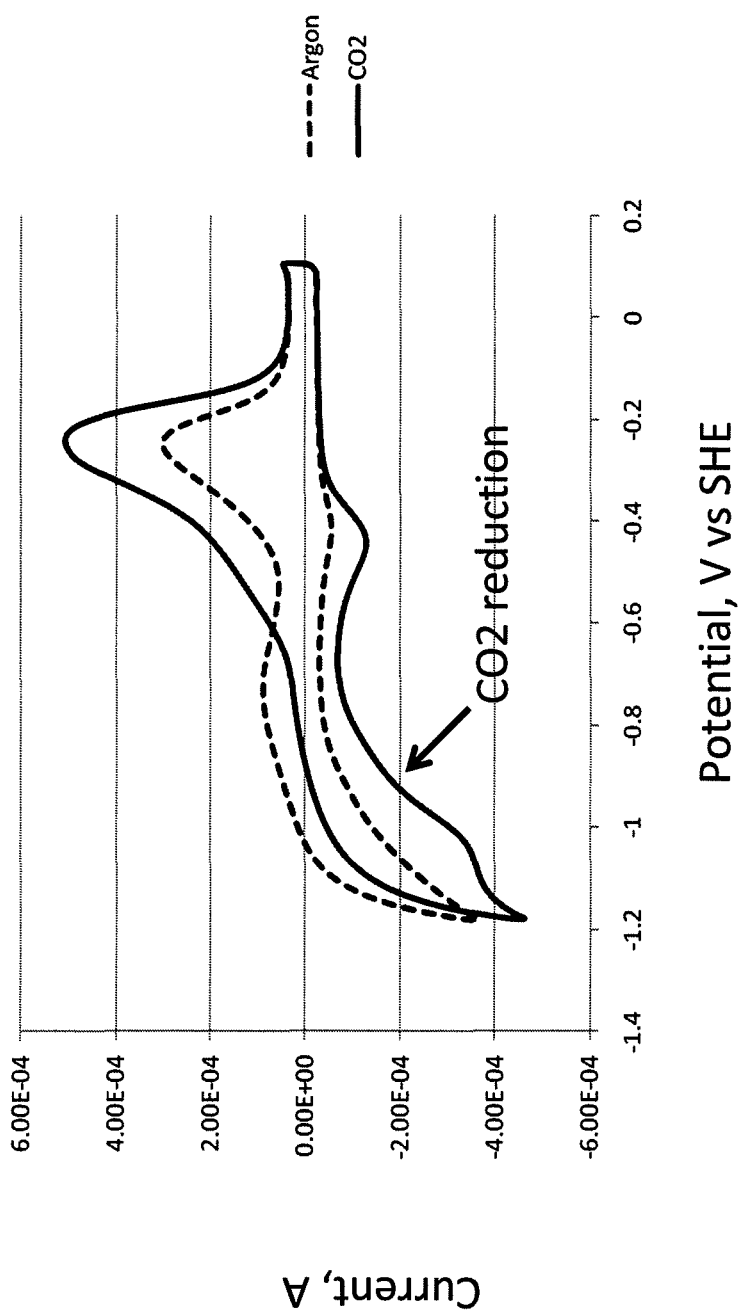
FIG. 12 shows a comparison of the cyclic voltammetry for a blank scan where the catalyst was synthesized as in Example 2 where (i) the water-choline chloride mixture was sparged with argon and (ii) a scan where the water-choline chloride mixture was sparged with CO$_2$.

The cell contained 52 mg of palladium and 65 mg of Helper Catalyst, so the overall catalyst mixture contained 51% of Helper Catalyst. FIG. 12 shows a comparison of the cyclic voltammetry for (i) a blank scan where the water-choline chloride mixture was sparged with argon and (ii) a scan where the water-choline chloride mixture was sparged with $CO_2$. Notice the negative going peaks starting at about −0.6. This shows that $CO_2$ is being reduced at −0.6 V. By comparison the data in Table 2 indicates that a voltage more negative than −1.2 V is needed to convert $CO_2$ on palladium in the absence of the Helper Catalyst. Thus, the overpotential for $CO_2$ conversion has been lowered by 0.6 V by the Helper Catalyst.

Another important point is that there is no strong peak for hydrogen formation. A bare palladium catalyst would produce a large hydrogen peak at about −0.4 V at a pH of 7, while the hydrogen peak moves to −1.2 V in the presence of the Helper Catalyst. The Hori review reports that palladium is not an effective catalyst for $CO_2$ reduction because the side reaction producing hydrogen is too large. The data in FIG. 12 show that the Helper Catalysts are effective in suppressing hydrogen formation. The same effect can be observed in FIG. 11 for the choline iodide solution on palladium in Example 1.

Cyclic voltammetry was also used to analyze the reaction products. Formic acid was the only product detected. By comparison, the Hori review reports that the reaction is only 2.8% selective to formic acid in water. Thus the Helper Catalyst has substantially improved the selectivity of the reaction to formic acid.

This example also demonstrates that the present invention can be practiced with the Helper Catalyst choline chloride. Further, those familiar with the technology involved here will note that there is nothing special about the Active Element, Helper Catalyst pair of palladium and choline chloride. Similar effects have been found for choline acetate and choline tetrafluoroborate.

Further, those familiar with the technology involved here should recognize that the results should not depend on the thickness of the palladium foil. For example, if the thickness of the palladium foil were increased by a factor of 10, the active element-helper catalyst mixture would only contain 11% of helper catalyst. If the foil thickness is increased to 0.5 inches, the mixture will contain about 1% of helper catalyst.

Specific Example 3

Use of an Active Element, Helper Catalyst Mixture that Includes Nickel and Choline Chloride to Lower the Overpotential for Electrochemical Conversion of $CO_2$ to CO and Suppress Hydrogen Formation This example is to demonstrate that the present invention can be practiced using a second metal, namely, nickel.

The experiment used the cell and procedures in Example 2, with the following exception: a nickel foil from Alfa Aesar was substituted for the palladium foil.

Figure 13:
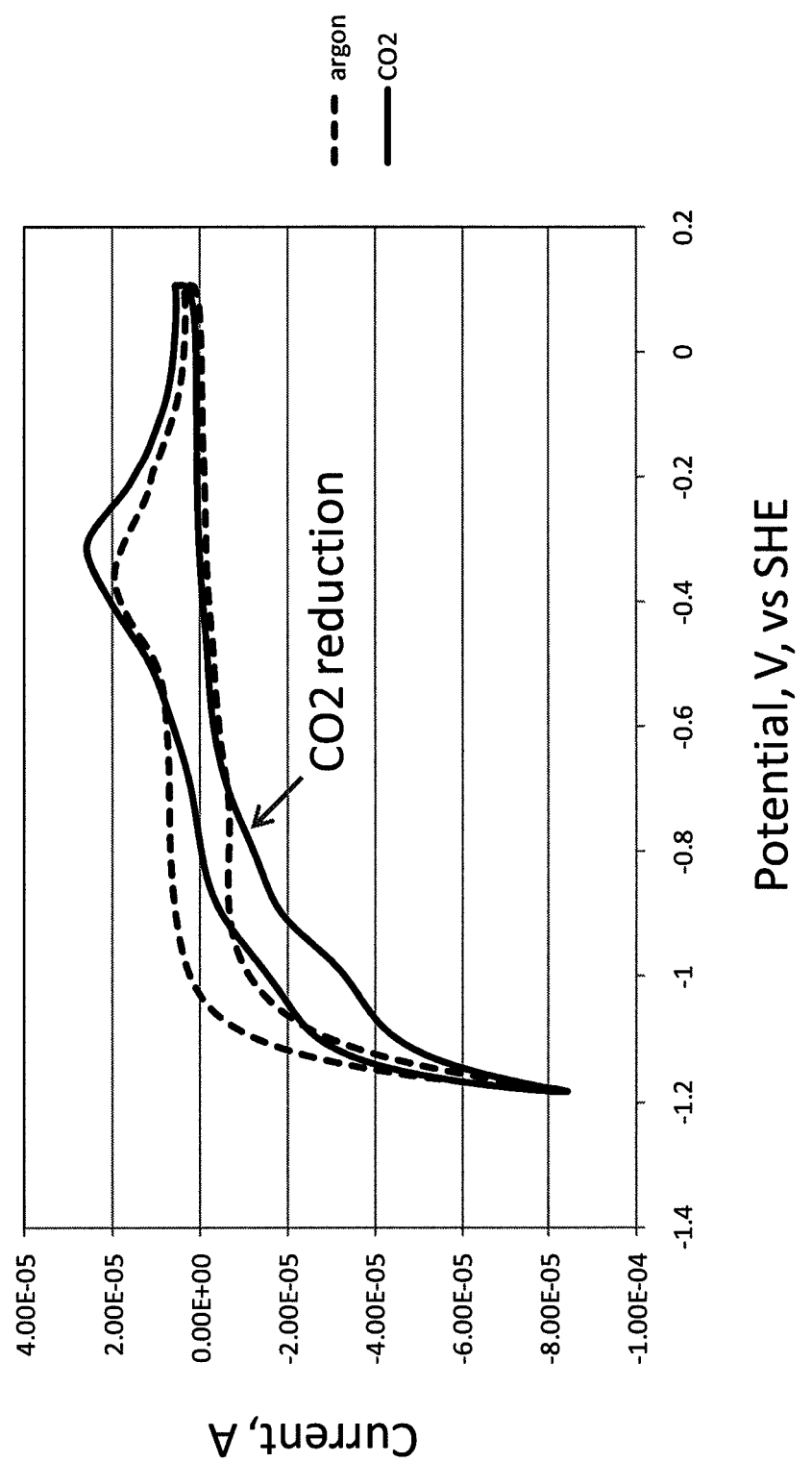
FIG. 13 shows a comparison of the cyclic voltammetry for a blank scan where the catalyst was synthesized as in Example 3 where (i) the water-choline chloride mixture was sparged with argon and (ii) a scan where the water-choline chloride mixture was sparged with CO$_2$.

FIG. 13 shows a comparison of the cyclic voltammetry for a blank scan where i) the water-choline chloride mixture was sparged with argon and ii) a scan where the water-choline chloride mixture was sparged with $CO_2$. Notice the negative going peaks starting at about −0.6. This shows that $CO_2$ is being reduced at −0.6 V. By comparison, the data in Table 2 indicates that a voltage more negative than −1.48 V is needed to convert $CO_2$ on nickel in the absence of the Helper Catalyst. Thus, the Helper Catalyst has lowered the overpotential for $CO_2$ conversion.

Another important point is that there is no strong peak for hydrogen formation. A bare nickel catalyst would produce a large hydrogen peak at about −0.4 V at a pH of 7, while the hydrogen peak moves to −1.2 V in the presence of the Helper Catalyst. The Hori review reports that nickel is not an effective catalyst for $CO_2$ reduction because the side reaction producing hydrogen is too large. The data in FIG. 13 show that the Helper Catalysts are effective in suppressing hydrogen formation.

Also the Helper Catalyst is very effective in improving the selectivity of the reaction. The Hori review reports that hydrogen is the major product during carbon dioxide reduction on nickel in aqueous solutions. The hydrolysis shows 1.4% selectivity to formic acid, and no selectivity to carbon monoxide. By comparison, analysis of the reaction products by CV indicates that carbon monoxide is the major product during $CO_2$ conversion on nickel in the presence of the Helper Catalyst. There may be some formate formation.

However, no hydrogen is detected. This example shows that the Helper Catalyst has tremendously enhanced the selectivity of the reaction toward CO and formate.

This example also demonstrates that the present invention can be practiced with a second metal, nickel. Further, those familiar with the technology involved here will note that there is nothing special about the Active Element, Helper Catalyst pair of nickel and choline chloride. The results are similar to those of other choline salts with palladium described above.

Those familiar with the technology involved here should realize that since choline chloride and choline iodide are active, other choline salts such as choline bromide, choline fluoride and choline acetate should be active as well.

Specific Example 4

Suppression of the Hydrogen Evolution Reaction (HER) and Enhancement of Formic Acid Electrooxidation in the Presence of Choline Chloride Materials:

The catalyst metal black ink was prepared by mixing 5.6 mg of metal black (Alfa Aesar 99.9% metal basis) with 1 ml deoxygenated Millipore water. There were two kinds of counter electrodes used in this experiment. For platinum and palladium catalyst, the counter electrode was made by attaching a 25×25 mm platinum mesh (size 52) to a 5 inch platinum wire (99.9%, 0.004 inch diameter). For a gold electrode, the counter electrode was made by attaching a 25×25 mm gold mesh (size 52) to a 5 inch gold wire (99.9%, 0.002 inch diameter). The reference electrode was a silver-silver chloride electrode with a Flexible Connector (Table 4). Four kinds of electrolyte were used: 0.5M choline chloride, 0.5M sodium bicarbonate, 0.5M sulfuric acid and buffer solution. The solutions were prepared with triple distilled water. Measurements were taken at 25° C. under argon gas (99.999% purity) bubbling at 1 atm.

Instruments:

The measurements were made with a Solartron SI 1287 potentiostat in a standard three-electrode electrochemical cell with an Ag/AgCl reference electrode. The working electrode was prepared by applying the metal black ink onto the gold surface of a rotating electrode. The catalyst was applied on the surface of the rotating electrode by adding 12.5 μL of the ink to the surface and allowing the water to evaporate under ambient temperature for 60 minutes.

Cyclic Voltammetry:

The electrolytes were first loaded into the glass cell and then purged with dry argon (99.99%) for two hours in order to remove oxygen from the electrolytes. Prior to each experiment, a 20-40 linear sweep cyclic voltammogram at 75 mV·s$^{-1}$ was taken between −1.5 V and +1 V vs. Ag/AgCl in order to condition the electrodes and remove oxides from the surfaces. Then several cycles were performed at 10 mV·s$^{-1}$ before taking the final cycle to insure that the CV had stabilized (that is, "dirt" or other material was removed from the surfaces). Finally, cleaning and stabilizing CV cycles were performed at 10 mV·s$^{-1}$. Later, formic acid was added in the electrolyte and the final concentrations were 0.001M, 0.01M and 0.03M. CV was obtained again to investigate the reaction between formic acid and catalyst surface. In order to ensure the quality of the measurements, special attention was paid to the material cleaning and solution purity (See Quaino, P. M., Gennero De Chialvo, M. R., and Chialvo, A. C., Hydrogen Diffusion Effects on the Kinetics of the Hydrogen Electrode Reaction Part II. Evaluation of Kinetic Parameters, Physical Chemistry Chemical Physics, 6(18): pages 4450-4455 (2004) and Montero, M. A., Marozzi, C. A., Chialvo, M. R. G. D., and Chialvo, A. C., The Evaluation of the Polarization Resistance in a Tubular Electrode and Its Application to the Hydrogen Electrode Reaction. Electrochimica Acta, 2007. 52(5): pages 2083-2090].

Calibration of the Reference Electrode:

Initially, an Ag/AgCl reference electrode connected to the cell through a Luggin Capillary was used, in hopes that the reference electrode would be stable. However, it was found that the reference electrode would drift when it was exposed to a choline chloride mixture. Therefore, the reference electrode was calibrated against a reversible hydrogen electrode (RHE) during each experiment. Essentially, a RHE was set up by bubbling hydrogen over the counter electrode and the potential of this electrode was compared to the reference electrode. To measure RHE potential, the working and the counter electrode leads are shorted, then, after bubbling hydrogen under the counter electrode for 20 minutes, the open cell potential was measured until it stabilized. The open cell potential was the RHE vs. Ag/AgCl electrode. This permitted determination of a reference potential for each run. In the work that follows, the data was plotted against the measured potential of the reversible hydrogen electrode, to avoid issues with the drift of the reference electrode. Four solutions were used, as shown in Table 4. A 0.5M choline chloride solution was compared to three standard solutions: 0.5M sodium bicarbonate, 0.5M sulfuric acid and a borax buffer solution. Sulfuric acid was an internal standard. Sodium bicarbonate and the borax buffer have a similar pH to the choline chloride solutions, so they were good comparison cases.

TABLE 4

(Calculated and measured values of the potential of the Ag/AgCl electrode)

|  | pH | Equilibrium potential of the Ag/AgCl electrode after exposure to the solution, V vs. RHE |
| --- | --- | --- |
| Choline Chloride | 8.6 | 0.08 |
| 1M Sulfuric Acid | 1.2 | 0.27 |
| Sodium Bicarbonate | 8.5 | 0.27 |
| Buffer | 8.6 | 0.28 |

Chronoamperometry:

Chronoamperometry was generally performed by stepping from open cell potential to the potential of interest, unless noted otherwise. The potential mentioned for chronoamperometric data is the potential that was stepped to from open cell potential. Two kinds of electrolyte were prepared for measurement: 0.01M formic acid solution and 0.01M formic acid in 0.5M choline chloride. The potential was held at 0.2 V vs. RHE and the current-time (1-t) curve was recorded with a potentiostat.

Theoretically, formic acid first adsorbs on the catalyst surface and then goes into two reaction routes (Batista, B. C. and Varela, H., Open Circuit Interaction of Formic Acid with Oxidized Pt Surfaces: Experiments, Modeling, and Simulations, Journal of Physical Chemistry C, 114(43), pages 18494-18500): direct formation of carbon dioxide and water; or firstly transferring to adsorbed carbon monoxide and then becoming carbon dioxide. In this experiment, the elevated current density in choline electrolyte was attributed to the choline ion's preference for the reaction through the first route instead of forming adsorbed CO on the surface.

Experimental Results

Hydrogen Evolution Reaction Suppression:

The first experiments were to determine whether choline chloride would inhibit HER. Cyclic voltammetry was performed in each of the solutions to see how the hydrogen evolution reaction changed.

Figure 14:
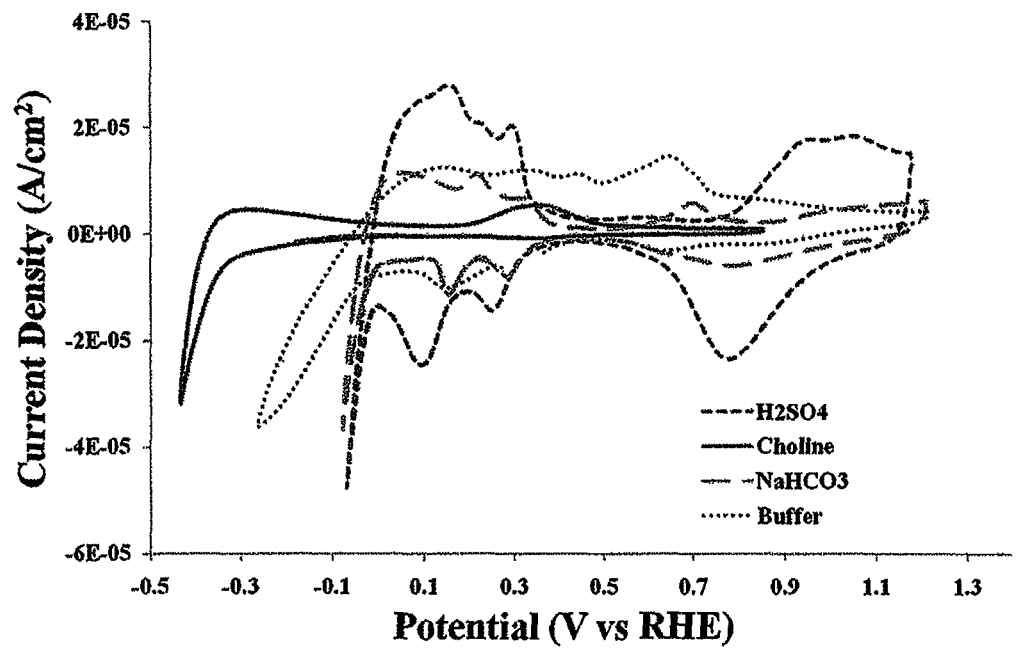
FIG. 14 shows a plot of cyclic voltammetry of platinum in different electrolytes, including 0.5M choline chloride. In each case the potential is reported versus the measured value of the RHE.

FIG. 14 presents the cyclic voltammetric measurements of the hydrogen evolution reaction on platinum catalyst in 0.5M solutions containing sulfuric acid, bicarbonate, borax buffer and choline chloride. In each case the potential was plotted versus the measured value of RHE to avoid the issues with the drift in the Ag/AgCl reference electrode. The sulfuric acid data looked similar to those from the previous literature, with hydrogen adsorption peaks at 0.11 V and 0.27 V, and hydrogen desorption peaks at 0.14 V, 0.21 V and 0.28 V. The hydrogen evolution started at around 0V. In sodium bicarbonate electrolyte, the peaks related to hydrogen reactions were at almost the same potentials as in sulfuric acid. There were hydrogen adsorption peaks at 0.16 V and 0.30 V, and hydrogen desorption peaks at 0.20 V and 0.30 V. The hydrogen evolution reaction began at zero (0) V as well. The same situation happened in buffer solution, which showed the hydrogen adsorption peaks at 0.17 V and 0.27 V, and hydrogen desorption peak at 0.14 V and 0.31 V. In this case, the hydrogen evolution reaction started at zero (0) V, but proceeded to bulk reaction slower than in sulfuric acid and sodium bicarbonate.

Everything changed in the choline chloride electrolyte. The characteristic hydrogen adsorption and desorption peaks were not observed. There was a peak at 0.33 V (RHE) that was attributed to the interaction between choline ion and catalyst surface, and a hydrogen reduction peak at about 0.4 V vs. RHE.

Other catalysts such as Pd and Au were also tested. The same suppression phenomenon was observed for the hydrogen evolution reaction.

Figure 15:
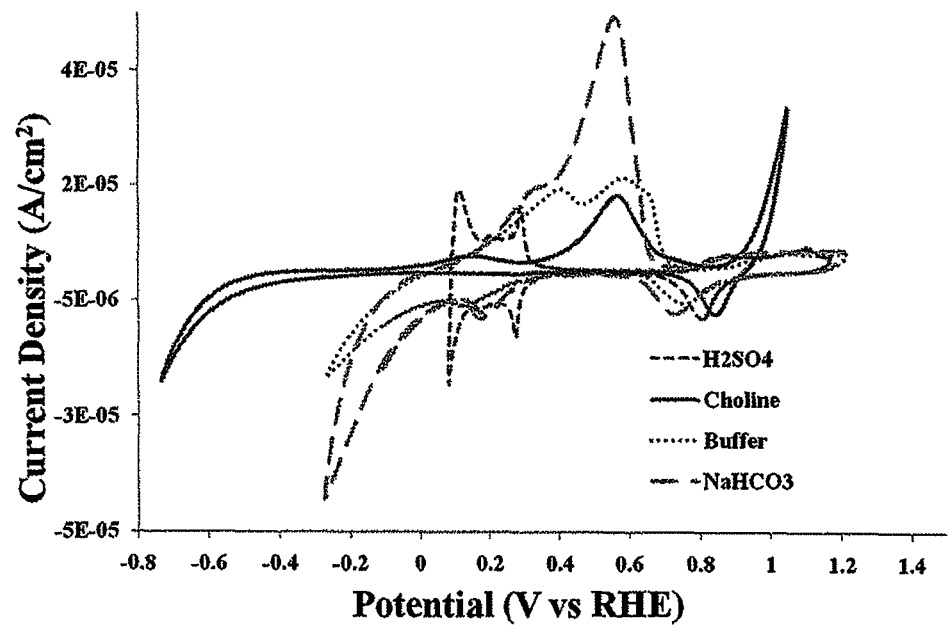
FIG. 15 shows a plot of cyclic voltammetry of palladium in different electrolytes, including 0.5M choline chloride.

With palladium catalyst, the bulk hydrogen evolution happened at 0.07 V in sulfuric acid (see FIG. 15). Hydrogen adsorption happened at 0.21 V and 0.27 V, and hydrogen desorption at 0.19 V and 0.26 V. In sodium bicarbonate, the obvious peaks of hydrogen adsorption and desorption were at 0.20 V and 0.30 V. The huge peak ranging from 0.30 V to 0.66 V was related to the reversible reaction of reduction products with catalyst surface, because the peak increases if the potential is pushed to more negative values. In buffer solution, a hydrogen adsorption peak at 0.19 V and hydrogen desorption peak at 0.36 V could still be observed. In both sodium bicarbonate and buffer solution, the hydrogen evolution reaction started around the same potential as sulfuric acid, but the bulk hydrogen evolution reaction happened more slowly than in sulfuric acid.

In choline chloride, there was a smooth line at the point where hydrogen adsorption happened in other electrolytes and the characteristic potential change of hydrogen adsorption was still not observed. The hydrogen evolution started smoothly below about $-0.5$ V.

Figure 16:
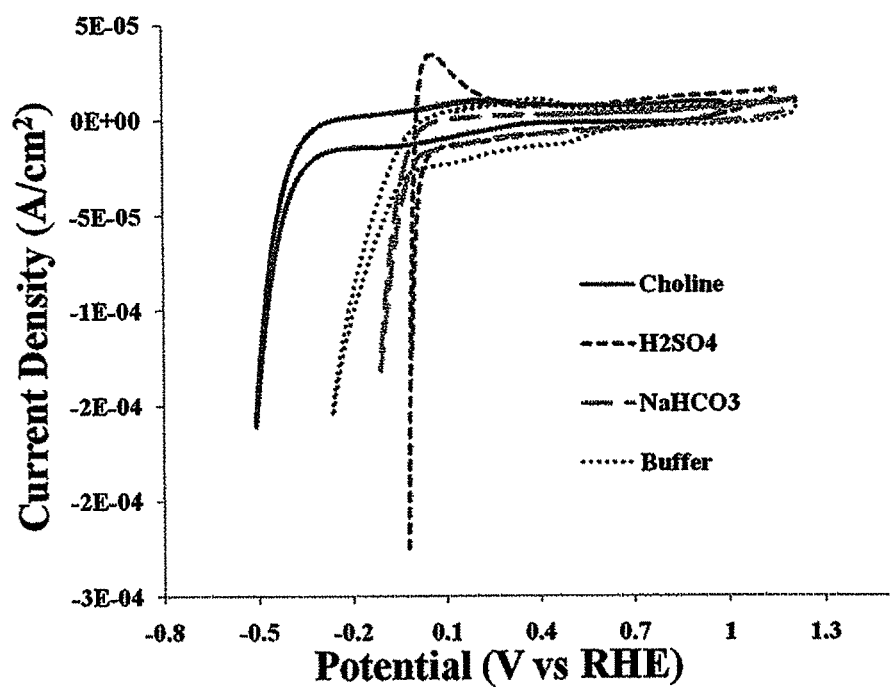
FIG. 16 shows a plot of cyclic voltammetry of gold in different electrolytes, including 0.5M choline chloride.

Gold showed less activity than the catalysts discussed before according to FIG. 16. In four kinds of electrolyte, the hydrogen adsorption peaks could hardly be seen. In sulfuric acid, hydrogen evolution started at around 0V, in agreement with previous literature (Daniel, R. M., Ionel, C. S., Daniel, A. S., and Mortimer, J. T., Electrochemistry of Gold in Aqueous Sulfuric Acid Solutions under Neural Stimulation Conditions, Journal of the Electrochemical Society, 152(7), pages E212-E221 (2005)). In sodium bicarbonate and buffer solution, the hydrogen evolution happened at the same potential as in the sulfuric acid. In choline chloride, however, the hydrogen evolution reaction started at $-0.3$ V. Therefore, with gold catalyst, choline chloride still showed the strongest suppression of the hydrogen evolution reaction among all four electrolytes.

Examining the Effect of Choline Chloride on the Formic Acid Electro-Oxidation:

The results in the previous section indicated that hydrogen formation was strongly suppressed in the presence of choline chloride. The next question to be addressed was whether the catalyst had been completely poisoned, or whether there instead had been a positive effect of formic acid electrooxidation.

Figure 17:
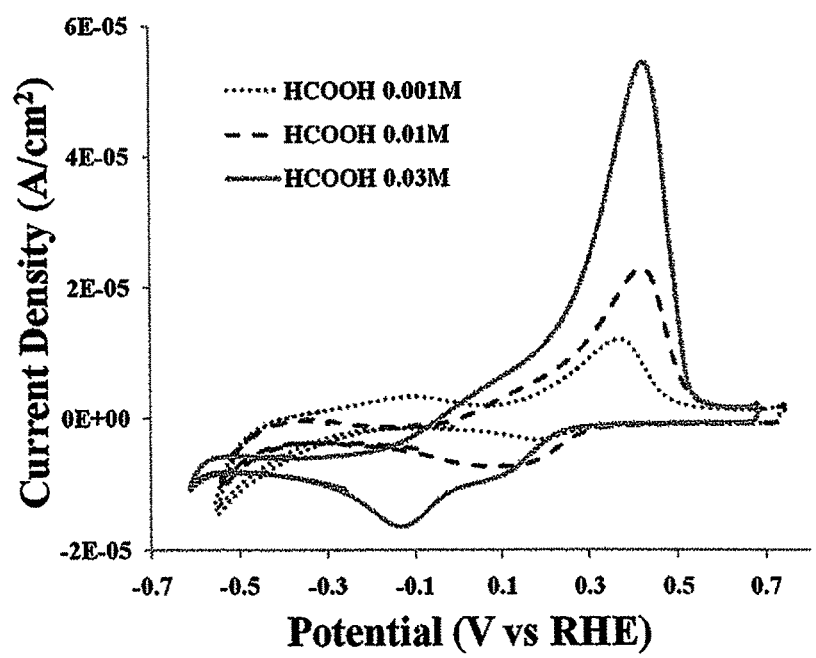
FIG. 17 shows a plot of cyclic voltammetry of palladium in choline chloride with different concentrations of formic acid.

FIG. 17 shows the results of a series of CV's of formic acid on a palladium catalyst. There were two formic acid oxidation peaks, one at about zero and a second at about 0.4 V. These are similar positions to those observed previously on palladium, although conversion was observed at lower potential than on clean palladium in the literature. The only major difference was that the large hydrogen evolution peaks were suppressed. The plot shows that there was considerable current at voltages between 0.1 and 0.4 V vs. RHE. This is the same range where the anodes in formic acid fuel cells operate. This indicates that choline chloride does not suppress the electro-oxidation of formic acid on palladium.

Figure 18:
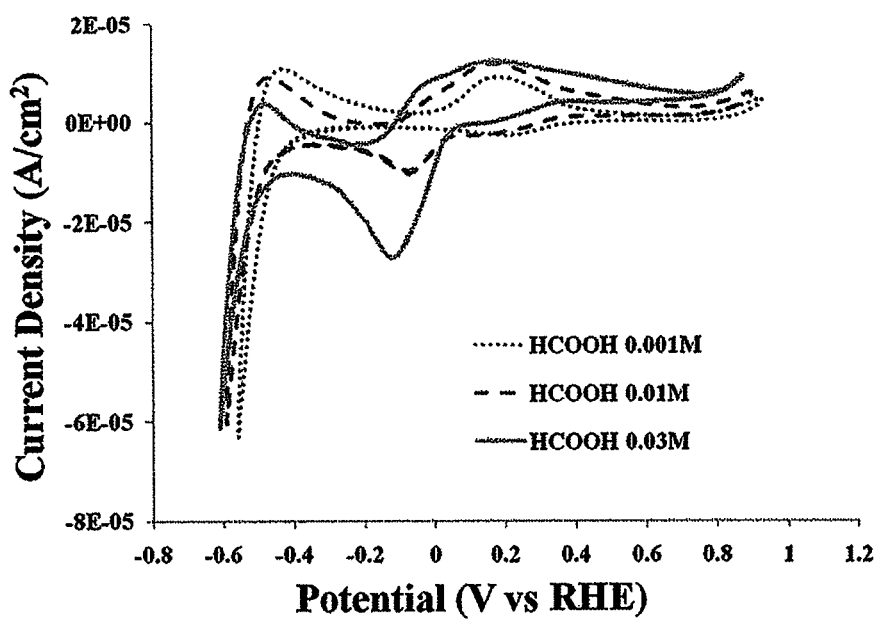
FIG. 18 shows a plot of cyclic voltammetry of platinum in choline chloride with different concentrations of formic acid.

FIG. 18 shows the CV measured for formic acid in choline chloride on platinum. The currents were smaller here, but again some formic acid electroxidation was observed near zero with respect to RHE, and more around 0.6 V. Formic acid electrooxidation can follow two different routes on platinum; a direct pathway that has been theorized to go through a formate intermediate, and an indirect pathway going through an adsorbed CO intermediate. The oxidation peak around zero (0) V with respect to RHE, and the reduction peak around $-0.1$ V with respect to RHE are characteristic of the direct pathway, while the shoulder around 0.6 V is characteristic of the CO pathway. The fact that these positions were at about the same potential as on platinum showed that formic acid electro-oxidation on platinum is not strongly inhibited by the presence of choline chloride.

Figure 19:
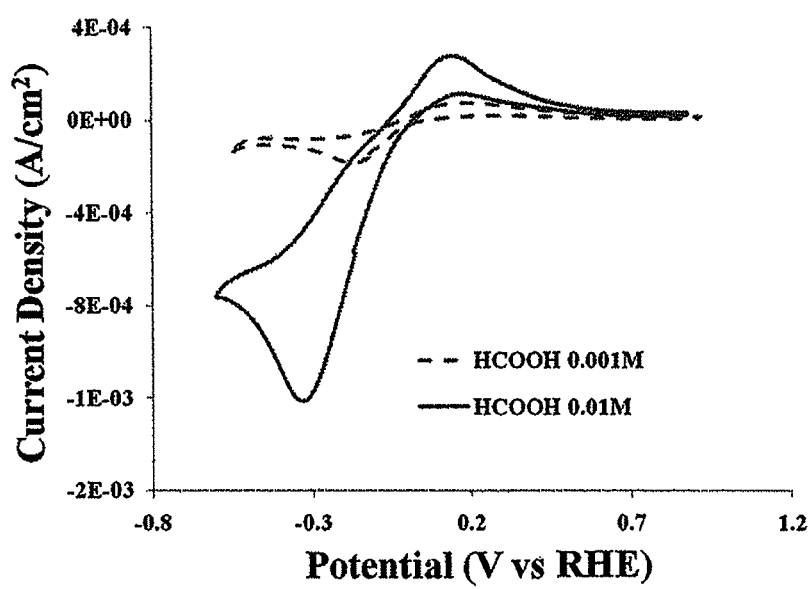
FIG. 19 shows a plot of cyclic voltammetry of gold in choline chloride with different concentrations of formic acid.

The same experiment was also done on a gold surface. FIG. 19 shows the cyclic voltammetry of formic acid on gold. Formic acid electrooxidation on gold is difficult to study because much of the chemistry occurs below RHE, and it is swamped by the hydrogen reduction reaction. The hydrogen reduction reaction was suppressed in the presence of the choline chloride, and instead a fairly large formic acid reduction peak was observed at about $-0.3$ V.

These results demonstrated that formic acid oxidation and reduction were not suppressed in the presence of choline chloride even though hydrogen evolution was suppressed.

Figure 20:
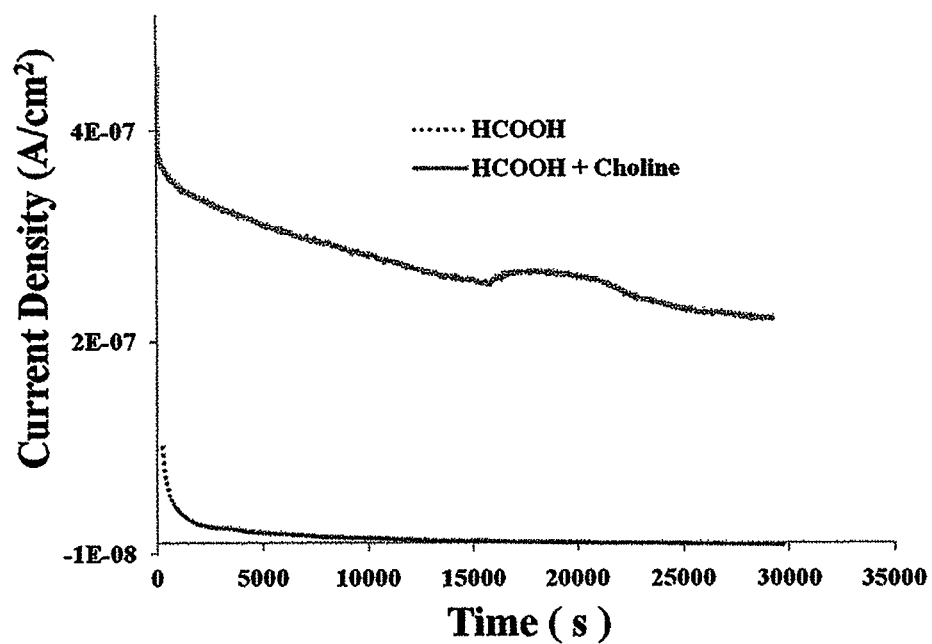
FIG. 20 shows chronoamperometric data for Pt black on gold electrode at 0.2 V vs. RHE in pure formic acid solution and formic acid solution with choline chloride.

Chronoamperometry:

Another question is whether formic acid electrooxidation would be enhanced in the presence of choline chloride. FIG. 20 shows chronoamperometric scans for Pt held at 0.2 V vs. RHE in choline chloride electrolyte with 0.01M formic acid compared to pure formic acid electrolyte. A potential of 0.2 V was chosen because this potential is similar to that used in formic acid fuel cells.

For both chronoamperometric curves, the current density started out high on the Pt surface. Then, as formic acid was depleted near the electrode surface, the current density rapidly dropped and later become relatively stable for 5 hours. After around 6 hours, the current density with pure formic acid electrolyte became zero and then switched to negative values. The activity of the Pt catalyst with formic acid and choline chloride, however, still stayed relatively high even after 6-hour operation. Results also demonstrated more than an order of magnitude improvement in the measured current density for this electrolyte over that of pure formic acid solution.

Surface Enhanced Raman Spectroscopy (SERS):

In other work, the applicants and co-workers have done surface enhanced Raman spectroscopy (SERS) to examine choline chloride adsorption on gold films. In all cases, strong peaks were observed at 2976 $cm^{-1}$, 1453 $cm^{-1}$, 967 $cm^{-1}$, 717 $cm^{-1}$ as expected for adsorbed choline cations. Therefore, it was concluded that choline ions adsorb molecularly on gold as expected.

The above data indicates that the hydrogen evolution reaction is suppressed and the electrooxidation of formic acid is enhanced. Fortunately, both are desirable results. The HER is undesirable during $CO_2$ conversion in aqueous media, because HER competes with the main reaction, $CO_2$ conversion. It is also a side reaction in formic acid fuel cells. Therefore inhibition of the HER would be desirable. On the other hand, formic acid electrooxidation is the main reaction in formic acid fuel cells. Enhancements could improve the stability of the fuel cell and lower the needed catalyst loading.

Predictive Examples of Director Molecules and Director Ions:

The applicants believe that to serve as a director molecule (or ion) for purposes such as suppressing hydrogen evolution in an electrochemical cell, the chemical species should have at least one positively charged group and at least one group for surface attachment (for example, for attachment to the negative electrode). In other words, what is needed is a positively charged species with something to hold the positive charge on the surface, but not to bind so strongly that the surface is poisoned. A number of alcohols, aldehydes, ketones, and carboxylic acids should work, although some carboxylic acids might bind too tightly to the electrode surface, and may thus poison the desired reaction. Similarly, other polar groups in addition to —OR, —COR, and —COOR, such as —$NR_2$, —$PR_2$, —SR and halides, where the R groups can independently be hydrogen or ligands containing carbon, (with the possible exception of carboxylic acid groups and their salts,) could serve as satisfactory surface attachment groups. For the positively charged group, a variety of amines and phosphoniums should be satisfactory. The key is to add an attached group to bind them to the surface, and the positive group(s) should not be so large as to be hydrophobic. Methyl, ethyl and propyl quaternary amines should perform well. Imidazoliums (sometimes also called imidazoniums) should also be satisfactory, provided they contain an attachment group. A significant aspect of the present invention is the identification of molecules or ions that can serve as both Helper Catalysts (accelerating or lowering the overpotential for desired reactions) and director molecules (increasing the selectivity toward the desired reaction, for example, by poisoning undesired reactions more than the desired reaction).

Specific Example 5

Demonstration that an Active Element (Gold), Helper Catalyst Mixture is Useful in a $CO_2$ Sensor)

The sensor can be a simple electrochemical device wherein an Active Element, Helper Catalyst Mixture is placed on an anode and cathode in an electrochemical device, then the resistance of the sensor is measured. If there is no $CO_2$ present, the resistance will be high, but preferably not infinite, because of leakage currents. When $CO_2$ is present, the Active Element, Helper Catalyst Mixture can catalyze the conversion of $CO_2$. That allows more current to flow through the sensor. Consequently, the sensor resistance decreases. As a result, the sensor can be used to detect carbon dioxide.

Figure 21:
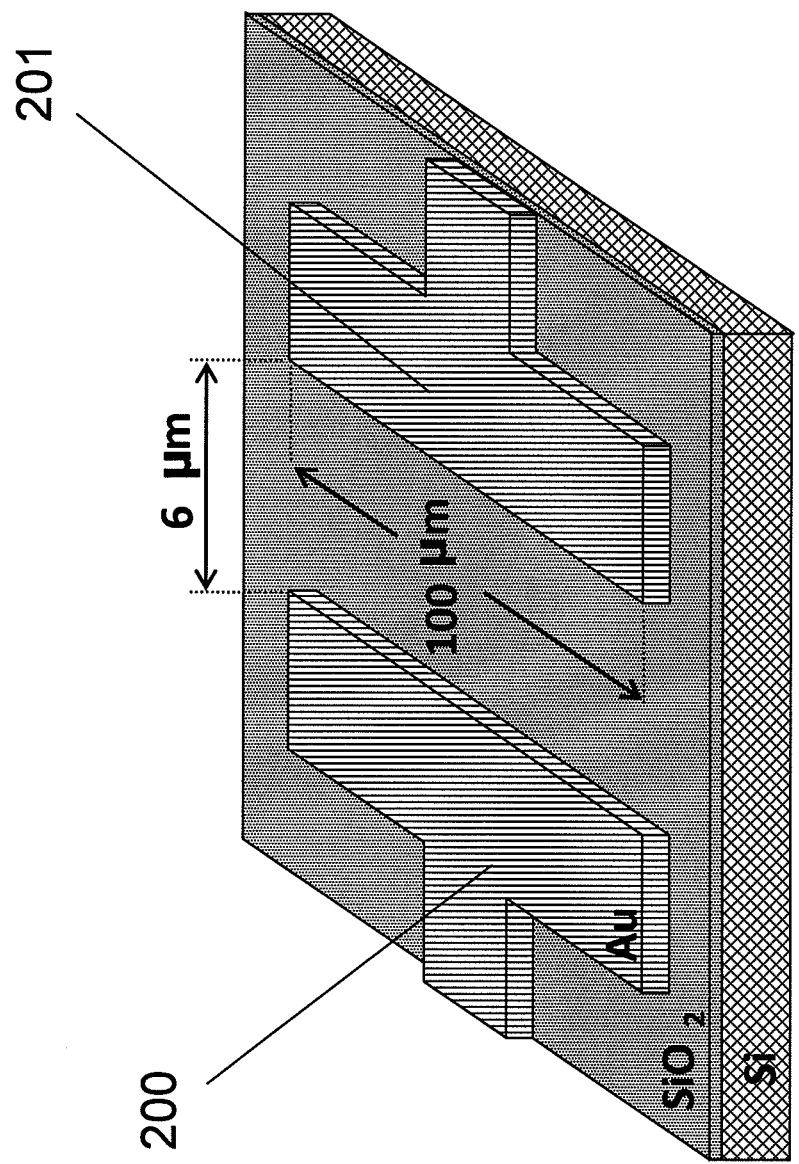
FIG. 21 shows a schematic diagram of an example sensor before the Helper Catalyst was added.

An example sensor was fabricated on a substrate made from a 100 mm silicon wafer (Silicon Quest International, Inc., Santa Clara, Calif., USA, 500 μm thick, <100> oriented, 1-5 Ω·cm nominal resistivity) which was purchased with a 500 nm thermal oxide layer. On the wafer, 170 Å of chromium was deposited by DC magnetron sputtering (~$10^{-2}$ Torr of argon background pressure). Next, 1000 Å of a Catalytically Active Element, gold, was deposited on the chromium and the electrode was patterned via a standard lift-off photolithography process to yield the device shown schematically in FIG. 21.

At this point, the device consisted of an anode 200 and cathode 201 separated by a 6 μm gap, wherein the anode and cathode were coated with a Catalytically Active Element, gold. At this point the sensor could not detect $CO_2$.

Figure 22:
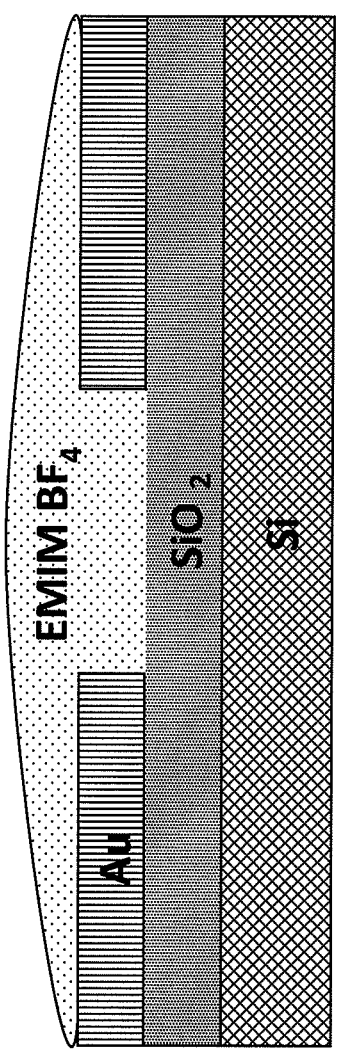
FIG. 22 shows a schematic diagram of where EMIM-BF4 is placed on the sensor.

Next 2 μl of a Helper Catalyst, EMIM-BF4 202 was added over the junction as shown in FIG. 22. The device was mounted into a sensor test cell with wires running from the anode and cathode. (It is believed that choline salts or other Helper Catalysts that suppress hydrogen evolution could be readily substituted for the Helper Catalyst EMIM-BF4.)

Figure 23:
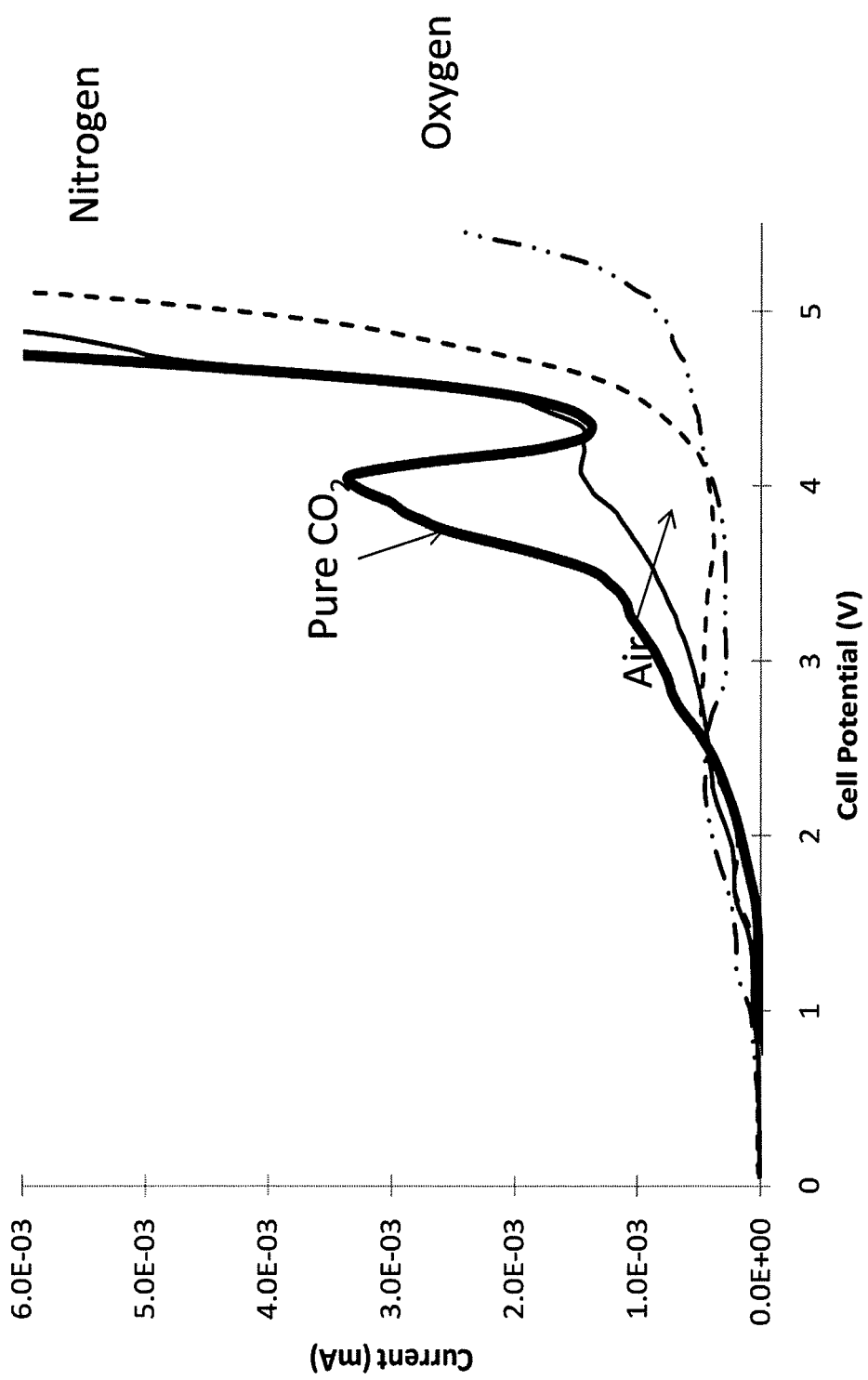
FIG. 23 represents the current measured when the voltage on the sensor was exposed to various gases; the applied voltage on the sensor was swept from 0 to 5 volts at 0.1 V/sec.

Next, the anode and cathode were connected to a SI 1287 Solartron electrical interface, and the catalysts were condition by sweeping from 0 V to 5 V at 0.1 V/sec and then back again. The process was repeated 16 times. Then the sensor was exposed to either nitrogen, oxygen, dry air or pure $CO_2$, and the sweeps were recorded. The last sweep is shown in FIG. 23. Notice that there is a sizable peak at an applied voltage of 4 V in pure $CO_2$. That peak is associated with the electrochemical conversion of $CO_2$.

Notice that the peak is absent when the sensor is exposed to oxygen or nitrogen, but it is clearly seen when the sensor is exposed to air containing less than 400 ppm of $CO_2$. Further, the peak grows as the $CO_2$ concentration increases. Thus, the sensor can be used to detect the presence of $CO_2$.

Figure 24:
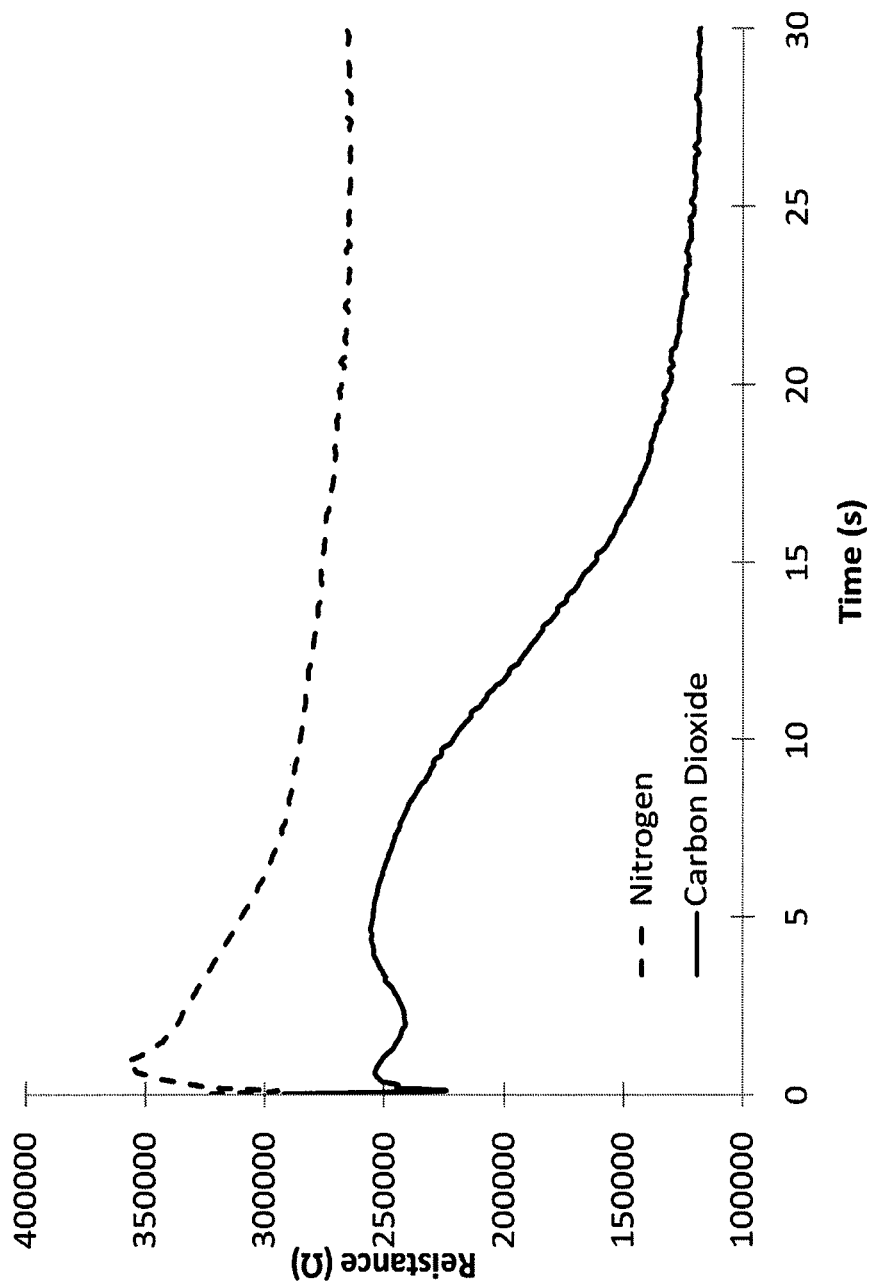
FIG. 24 represents the resistance of the sensor, in nitrogen and in carbon dioxide. The resistance was determined by measuring the voltage needed to maintain a current of 1 microamp. Time is the time from when the current was applied.
Figure 25A:
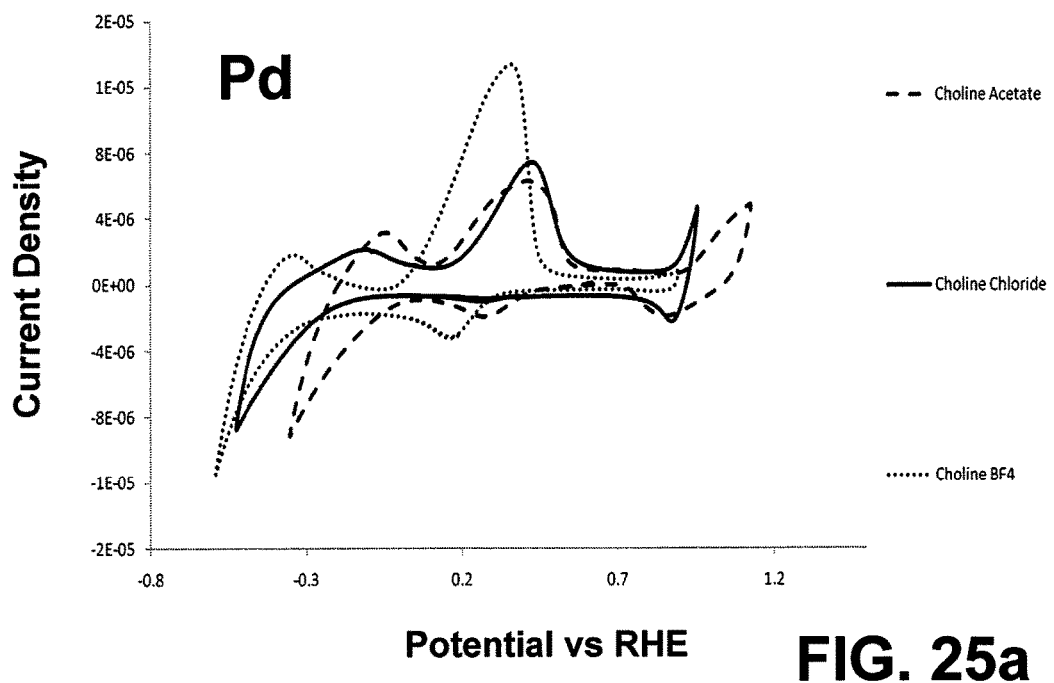
FIGS. 25a and 25b each shows a plot of cyclic voltammetry of palladium in the presence of different hydrogen suppressors. In each case the potential is reported versus the measured value of RHE.
Figure 25B:
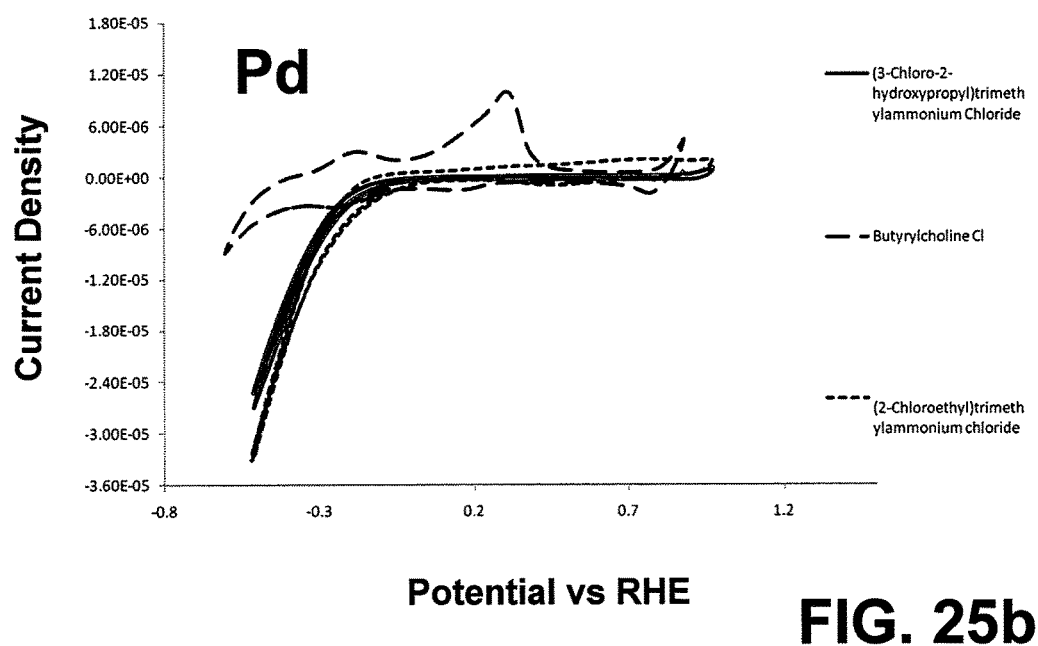
Figure 26A:
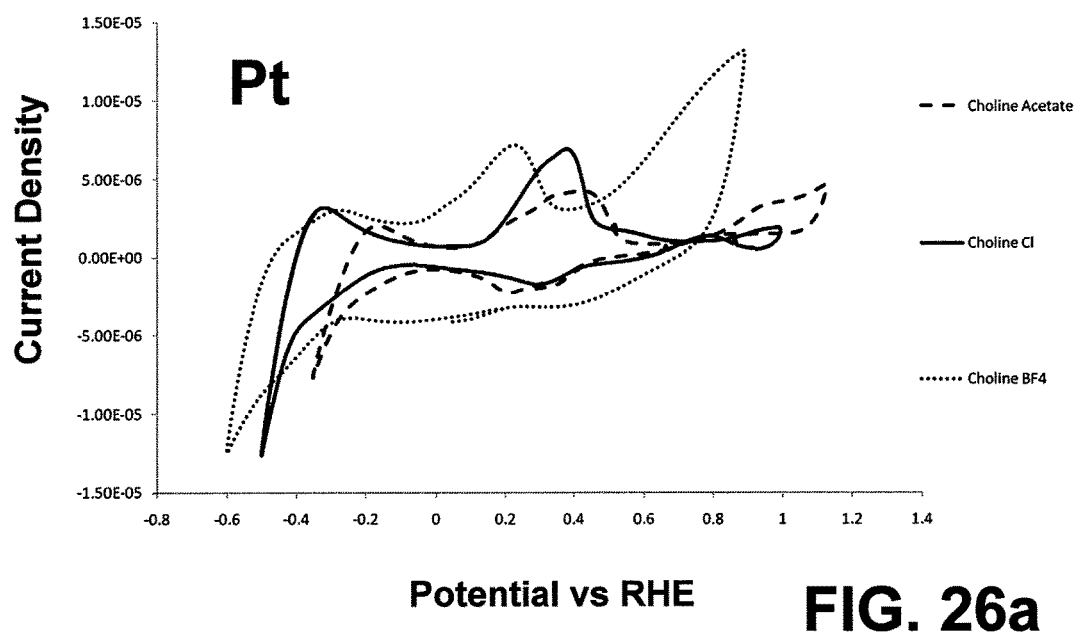
FIGS. 26a and 26b each shows a plot of cyclic voltammetry of platinum in the presence of different hydrogen suppressors. In each case the potential is reported versus the measured value of RHE.
Figure 26B:
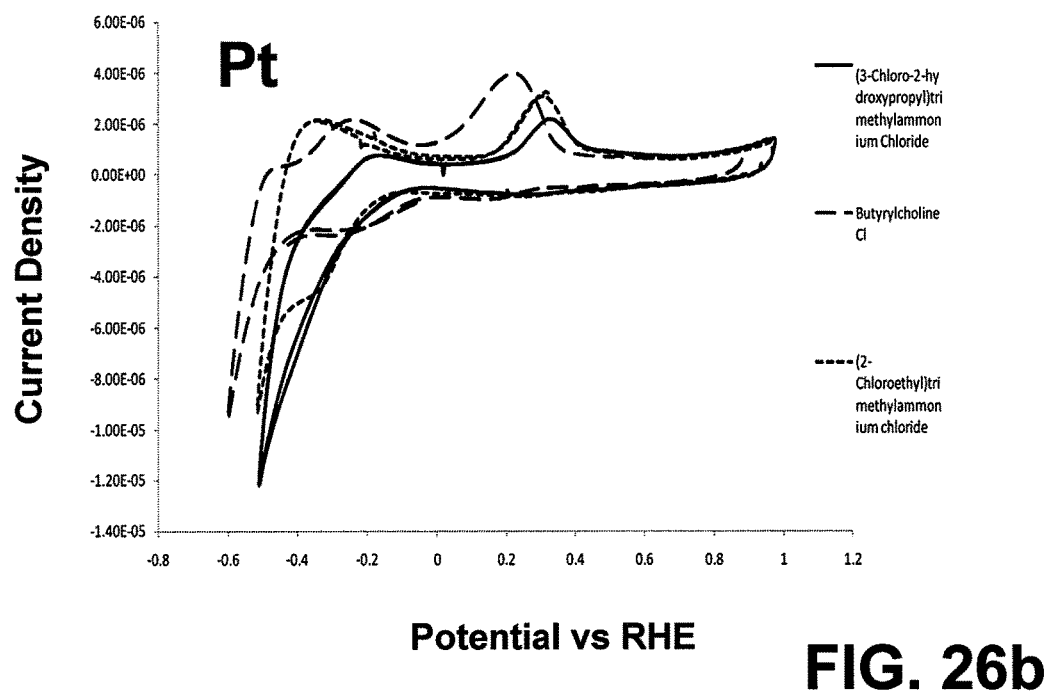
Figure 27A:
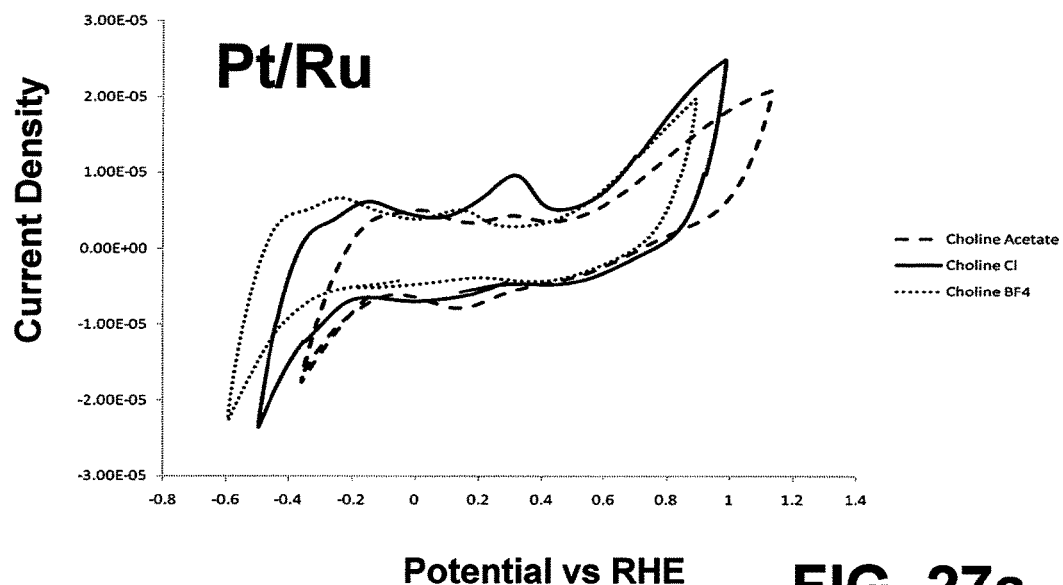
FIGS. 27a and 27b each shows a plot of cyclic voltammetry of platinum/ruthenium in the presence of different hydrogen suppressors. In each case the potential is reported versus the measured value of RHE.
Figure 27B:
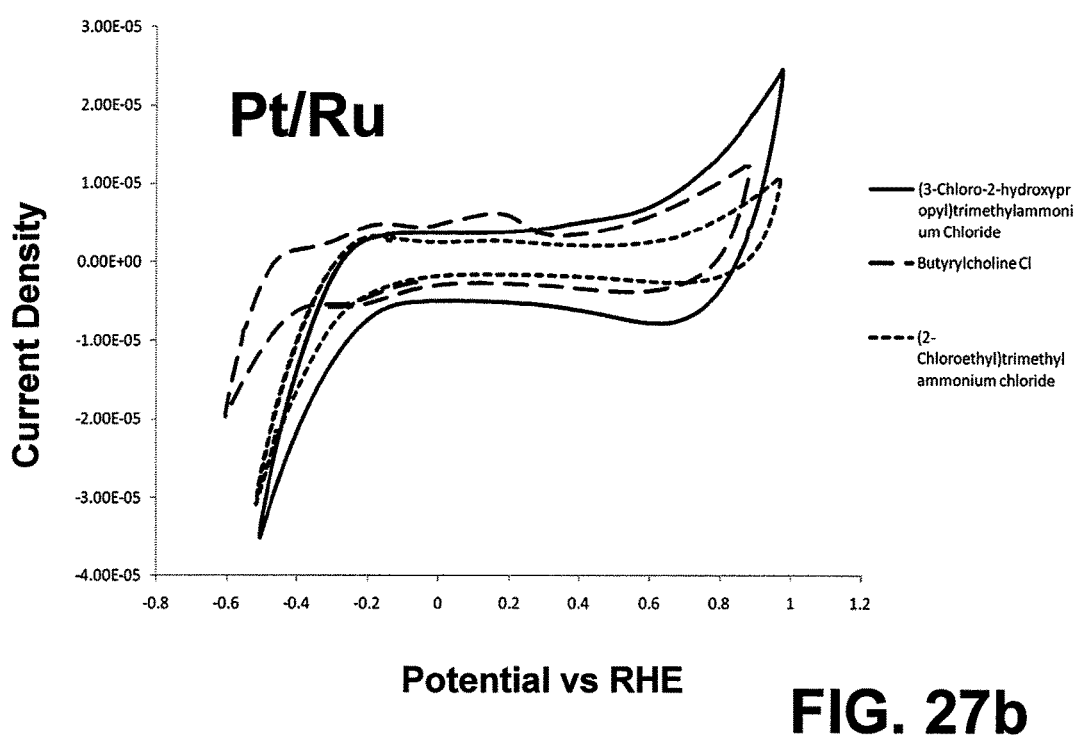

The sensor has also been run in a galvanastatic mode, wherein the applicants measured the voltage needed to maintain the current constant at 1 microamp, and measured the voltage of the device. FIG. 24 shows that less voltage is needed to maintain the current when $CO_2$ is added to the cell. This shows that the sensor that includes an Active Element, Helper Catalyst Mixture responds to the presence of $CO_2$.

Table 5 compares the sensor here to those in the previous literature. Notice that the new sensor uses orders of magnitude less energy than commercial $CO_2$ sensors. This is a key advantage for many applications.

This example also again illustrates that the present invention can be practiced with a fourth Active Element, gold.

TABLE 5

(Comparison of power needed to run the present sensor to that needed to operate commercially available $CO_2$ sensors)

| Sensor | Power | Sensor | Power |
|---|---|---|---|
| Specific Example 5 | 5 × 10−7 watts | GE Ventostat 8100 | 1.75 watts |
| Honeywell C7232 | 3 watts | Vaisala CARBOCAP GMP343 | about 1 watt |

Specific Example 6

Steady State Production of Carbon Monoxide

This experiment used the flow cell described in Devin T. Whipple, E. C. Finke, and P. J. A. Kenis, Electrochem. & Solid-State Lett., 2010, 13 (9), B109-B111 ("the Whipple paper"). First, catalyst inks were prepared as follows:

For the Cathode:

10 mg of silver nanoparticles (Sigma Aldrich) was sonicated into a solution containing 100 μL of water, 100 μL of isopropyl alcohol and 5.6 μL of 5% Nafion® (perfluorosulfonic acid) solution (Ion Power). The resultant catalyst ink was painted on a 1×1.5 cm section of a 2×3 cm piece of carbon paper (ion power) and dried with a heat lamp.

The preparation was identical for anode except 4 mg of HiSpec 1000 platinum black (Sigma Adrich) was substituted for the silver.

Both catalysts were mounted in the flow cell described in the Whipple Paper. Five sccm of $CO_2$ was fed to the anode, and a solution containing 18 mole percent of EMIM-BF4 in water was fed into the gap between the anode and the cathode. At any one time the cell contained approximately 10 mg of silver nanoparticles and approximately 40 mg of EMIM-BF4 Helper Catalyst. A potential was applied to the cell, and the data in Table 6 were obtained. These results demonstrate that steady state production of useful products can be obtained with Catalytically Active Element-Helper Catalyst Mixtures. It is believed that choline salts or other Helper Catalysts that suppress hydrogen evolution could be readily substituted for the Helper Catalyst EMIM-BF4.

TABLE 6

(Products produced at various conditions)

| Cathode potential Volts vs. RHE | Hydrogen production rate, μg/min | Carbon monoxide production rate, μg/min |
|---|---|---|
| −0.358 | 0 | 0 |
| −0.862 | 1.1 | 2.6 |
| −1.098 | 1.4 | 50 |
| −1.434 | 1.1 | 250 |
| −1.788 | 0 | 560 |

Specific Example 7

Demonstration of Hydrogen Suppression with Other Choline Derivatives

The experiments were the same as in Specific Example 4, except that one of (a) choline acetate, (b) choline BF4, (c) (3-chloro-2-hydroxypropyl)trimethyl ammonium chloride, (d) butyrylcholine chloride, and (e) (2-chloroethyl)trimethylammonium chloride were used instead of choline chloride (which is also shown here for comparison.) FIGS. 25a, 25b, 26a, 26b, 27a and 27b show CV's taken as described in Specific Example 2 on platinum, palladium and platinum/ruthenium catalysts. In all cases hydrogen suppression is observed. This result shows that (a) choline acetate, (b) choline BF4, (c) (3-chloro-2-hydroxypropyl)trimethyl ammonium chloride, (d) butyrylcholine chloride, and (e) (2-chloroethyl)trimethylammonium chloride are all hydrogen suppressors.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

The disclosures of all references and publications cited above are expressly incorporated by reference in their entireties to the same extent as if each were incorporated by reference individually.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. An electrochemical cell having a fluid phase, the fluid phase comprising a hydrogen evolution suppressor comprising a cation having at least one positive group selected from ammoniums and phosphoniums, and the cation further having at least one polar group covalently bonded to said cation and selected from the group consisting of —OR, —COR, —COOR, —NR$_2$, —PR$_2$, —SR and —X, where each R independently can be H or a linear, branched, or cyclic C1-C4 aliphatic group, —COOR is not a carboxylic acid, and —X is a halide.

2. The electrochemical cell of claim 1, wherein the cation comprises a quaternary amine group and at least one halide or hydroxyl group, and the cation further contains no carboxylic acid or ionized carboxylic acid group.

3. The electrochemical cell of claim 1, wherein said cation is choline, or a choline derivative of the form $R_1R_2R_3N^+(CH_2)_nY$, wherein n=1-4, $R_1$, $R_2$, and $R_3$ are independently selected from the group consisting of aliphatic $C_1$-$C_4$ groups, —CH$_2$OH, —CH$_2$CH$_2$OH, —CH$_2$CH$_2$CH$_2$OH and —CH$_2$CHOHCH$_3$, and Y is selected from the group consisting of hydroxide and halides.

4. The electrochemical cell of claim 1, wherein at least one of the reactants or the products of the reaction comprise at least one of the following: CO$_2$, CO, CO$_3^{2-}$, HCO$_3^-$, HCO$^-$, H$_2$CO, (HCO$_2$)$^-$, H$_2$CO$_2$, CH$_3$OH, CH$_4$, C$_2$H$_4$, CH$_3$CH$_2$OH, CH$_3$COO$^-$, CH$_3$COOH, C$_2$H$_6$, (COOH)$_2$, (COO$^-$)$_2$.

5. The electrochemical cell of claim 1, wherein the electrochemical cell is a fuel cell.

6. The electrochemical cell of claim 1, wherein the electrochemical cell is a sensor.

7. The electrochemical cell of claim 1, wherein the electrochemical cell is a cell for conversion of carbon dioxide.

8. The electrochemical cell of claim 1, said cell further comprising at least one Catalytically Active Element, wherein the Catalytically Active Element comprises at least one of the following chemical elements: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd.

* * * * *